(12) United States Patent
Nordon et al.

(10) Patent No.: US 12,305,153 B2
(45) Date of Patent: May 20, 2025

(54) MICROFLUIDIC DEVICE AND METHOD OF USE FOR CELL CULTURE

(71) Applicant: NewSouth Innovations Pty Limited, Sydney (AU)

(72) Inventors: Robert Ernest Nordon, Sydney (AU); Osmond Tsun Yin Lao, Sydney (AU)

(73) Assignee: NewSouth Innovations Pty Limited, Sydney (AU)

( * ) Notice: Subject to any disclaimer, the term of this patent is extended or adjusted under 35 U.S.C. 154(b) by 692 days.

(21) Appl. No.: 17/595,236

(22) PCT Filed: May 13, 2020

(86) PCT No.: PCT/AU2020/050473
§ 371 (c)(1),
(2) Date: Nov. 11, 2021

(87) PCT Pub. No.: WO2020/227772
PCT Pub. Date: Nov. 19, 2020

(65) Prior Publication Data
US 2022/0204903 A1 Jun. 30, 2022

(30) Foreign Application Priority Data
May 13, 2019 (AU) .................... 2019901630

(51) Int. Cl.
*C12M 3/06* (2006.01)
*C12M 1/00* (2006.01)
(Continued)

(52) U.S. Cl.
CPC ............ *C12M 23/16* (2013.01); *C12M 23/24* (2013.01); *C12M 23/58* (2013.01); *C12M 29/10* (2013.01); *C12M 29/20* (2013.01); *C12M 41/48* (2013.01)

(58) Field of Classification Search
CPC ...... C12M 23/16; C12M 23/24; C12M 23/58; C12M 29/10; C12M 29/20; C12M 41/48;
(Continued)

(56) References Cited

U.S. PATENT DOCUMENTS

2002/0106311 A1 8/2002 Golbig et al.
2006/0275184 A1 12/2006 Furukawa et al.
(Continued)

FOREIGN PATENT DOCUMENTS

CN 104560713 A 4/2015
JP H09-501324 A 2/1997
(Continued)

OTHER PUBLICATIONS

Japanese Examination Report for Application No. 567975/2021 dated Apr. 18, 2024, in 5 pages.
(Continued)

*Primary Examiner* — John McGuirk
(74) *Attorney, Agent, or Firm* — Knobbe, Martens, Olson & Bear, LLP

(57) ABSTRACT

A multi-layer microfluidic bioreactor is used in methods for culturing cells. A grooved semipermeable substrate can capture and grow cells using perfusion culture methods. Microfluidic geometry directs flow over grooves for cell expansion and along grooves for cell harvesting. The bioreactor and methods can be optimized for high density and automated processing for growth of cells.

19 Claims, 20 Drawing Sheets

(51) Int. Cl.
*C12M 1/04* (2006.01)
*C12M 1/36* (2006.01)

(58) Field of Classification Search
CPC .......... C12M 3/04; C12M 3/06; C12M 33/04;
C12M 29/14; C12M 41/44; C12M 25/00;
C12M 29/24; B01L 2200/143; B01L
2300/0816; B01L 2400/0487; B01L
3/502761; B01L 3/502715; B01L
3/50273; B01L 3/502738; B01L
2300/0861; C12N 2740/16043; C12N
2740/16051; C12N 5/0068; C12N 15/64;
C12N 15/87; C12N 2521/00; C12N
2535/10
See application file for complete search history.

(56) References Cited

U.S. PATENT DOCUMENTS

| | | |
|---|---|---|
| 2010/0216244 A1 | 8/2010 | Wu et al. |
| 2012/0301867 A1* | 11/2012 | Kumo ............... B01L 3/502746 |
| | | 435/2 |
| 2014/0142000 A1 | 5/2014 | Tung et al. |
| 2015/0267160 A1 | 9/2015 | Matsumura et al. |
| 2016/0340631 A1 | 11/2016 | Wang et al. |
| 2017/0349871 A1 | 12/2017 | Ingber et al. |
| 2018/0017584 A1 | 1/2018 | Levner et al. |
| 2018/0057784 A1 | 3/2018 | Wang et al. |
| 2018/0179485 A1 | 6/2018 | Borenstein et al. |

FOREIGN PATENT DOCUMENTS

| | | |
|---|---|---|
| JP | 2011-528232 A | 11/2011 |
| WO | WO 95/24464 A1 | 9/1955 |
| WO | WO 2011/035185 A2 | 3/2011 |

OTHER PUBLICATIONS

Chinese Office Action and Search Report for Application No. 202080035626.X dated Feb. 5, 2024, in 11 pages.
Extended European Search Report in European Patent Application No. 20806539.1 issued Jul. 13, 2022.
Supplementary European Search in European Patent Application No. 20806539.1 issued Jul. 5, 2022.
Communication Rule 70(2) And 70A(2) in European Patent Application No. 20806539.1 issued Aug. 2, 2022.
International Search Report in PCT/AU2020/050473, issued Jul. 15, 2020.
International—Type Search for Provisional Patent Application in Australian Patent Application No. 2019901630 issued Jan. 16, 2020.

\* cited by examiner

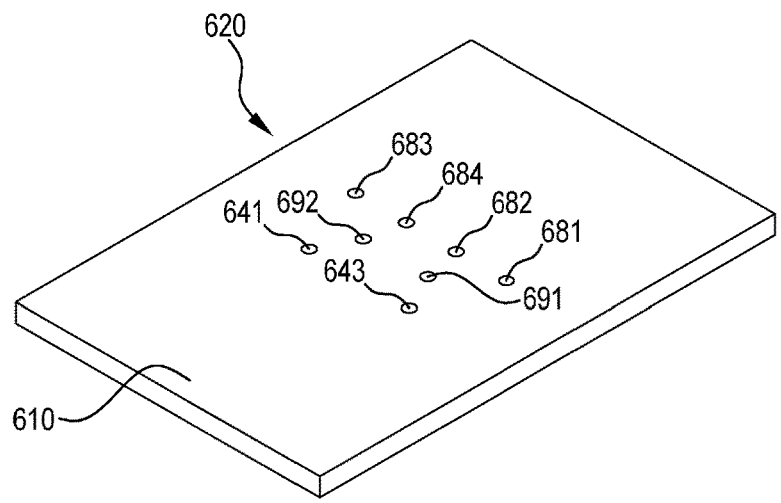
*Figure 12A*
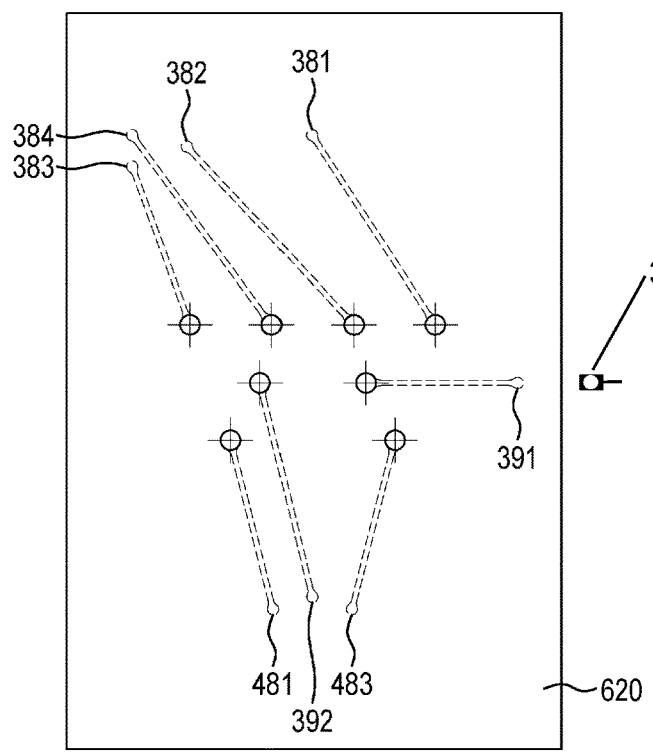
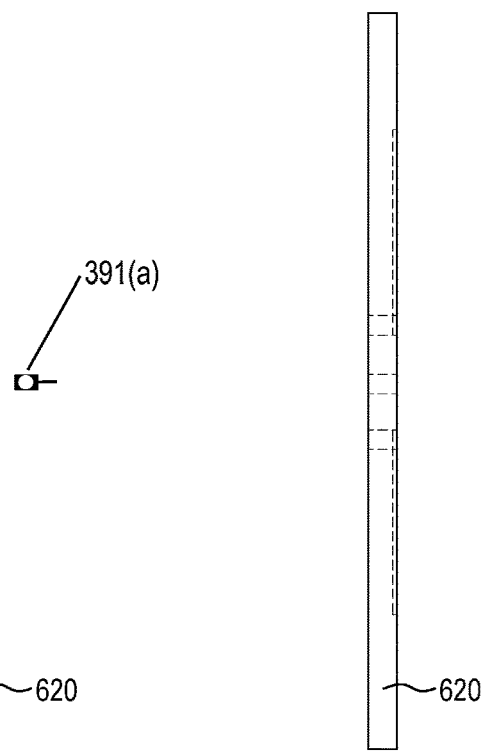
*Figure 12B* *Figure 12C*

Slice: Velocity magnitude (m/s)  Streamline: Velocity field

Slice: Velocity magnitude (m/s)  Streamline: Velocity field

Day 17 prior to cross-flow harvest  Day 17 following cross-flow harvest

Day 0 (after inoculation)

Day 3

Day 8

Day 12

Day 14 (after harvest)

Pluronic F127

MICROFLUIDIC DEVICE AND METHOD OF USE FOR CELL CULTURE

CROSS-REFERENCE TO RELATED APPLICATIONS

This application claims priority from Australian provisional patent application 2019901630 filed on 13 May 2019, the contents of which are to be taken as incorporated herein by this reference.

TECHNICAL FIELD

The present invention relates to a microfluidic bioreactor and method for use in cell culture. It relates particularly but not exclusively to a microfluidic bioreactor for high density cell culture which allows for integration of multiple cell culture processes into a single device.

BACKGROUND OF INVENTION

Cell and gene therapy involves modification of cells extracted from the patient's blood and can offer a cure for some cancers and genetic diseases in a single treatment. As cell and gene therapies progress from clinical proof-of-concept through to regulatory approval and product licensing, a major hurdle will be the scale-out of patient-specific treatments. It is estimated that the market for cell and gene therapy in the US and EU will grow beyond 200,000 patient-specific treatments per year. Current methods for modifying human cells with therapeutic genes include the following steps a) purification of blood stem or immune cells from human blood b) introduction of therapeutic DNA or RNA into target cells using viral or non-viral delivery systems c) mitotic activation of transduced cells by tissue culture for several days to facilitate viral entry and stable genomic integration. Lentiviral vectors are one of the more commonly used vectors for clinical trials because of their relative safety, minimal toxicity to cells and high rates of gene transfer. Traditional processes involve significant investment in large scale, centralised manufacturing facilities that utilise manual, flask based culture processes. Not only are these processes complex and labour-intensive they are prone to operator error and carry a contamination risk due to use of open flasks. Further, these processes are not easily scaled—for clinical therapies.

Current methods of culturing cells in tissue culture can be inefficient due to the lack of scale-up or limitations on the number of cells that can be grown due to unfavourable oxygen gradients, particularly for cell types which have a high oxygen demand such as hepatocytes. These scale-limited production processes are cumbersome and cost-prohibitive. In addition, known tissue culture apparatus can be inefficient through the loss of non-adherent cells in bulk media flow through fluidic shear stress, particularly for cell types which have a low endurance to shear stress such as human embryonic cells. This can limit the density at which cells can be grown through the limitation on maximum perfusion rates.

It would be desirable to overcome or ameliorate one or more of the above problems, or at least provide a useful alternative.

The discussion of the background to the invention included herein including reference to documents, acts, materials, devices, articles and the like is included to explain the context of the present invention. This is not to be taken as an admission or a suggestion that any of the material referred to was published, known or part of the common general knowledge as at the priority date of any of the claims.

SUMMARY OF INVENTION

Viewed from one aspect, the present disclosure provides a multi-layer microfluidic bioreactor for cell culture, comprising a header layer, a base layer and a fluid permeable flow layer between the header layer and the base layer. The flow layer comprises an upper surface and a lower surface, and the upper surface comprises one or more one grooves for retention of cells. The base layer provides a gas flow path for gas exchange across the flow layer. The header layer is configured to define a flow channel over the flow layer upper surface, and the header layer comprises: (i) a first inlet port; (ii) a first outlet port; (iii) one or more first fluid inlets providing fluid communication between the first inlet port and the flow channel; and (iv) one or more first fluid outlets providing fluid communication between the flow channel and the first outlet port. The one or more fluid inlets and the one or more fluid outlets are positioned in the header such that fluid entering the flow channel from the one or more fluid inlets moves in a first flow direction toward the one or more fluid outlets, the first flow direction being across the at least one groove to minimise disruption of cells received therein. In such arrangement, cells and media may enter the first inlet port and flow across the grooves, exiting at the first outlet port in the first flow direction being a cross flow direction.

In some embodiments, the header layer further comprises—a second outlet port and one or more second fluid outlets providing fluid communication between the flow channel and the second outlet port. The one or more second fluid outlets are positioned in the header such that fluid, which may contain cells retained in the one or more grooves, exiting the flow channel through the second outlet port flows in a second flow direction toward the one or more second fluid outlets, the second flow direction being along the one or more grooves. That is, the second fluid outlets are positioned along an edge of the flow channel running orthogonal to the grooves. Thus, the second fluid outlets may be arranged at the end of the grooves enabling cells and media to exit at the second outlet port in the second flow direction. Typically, the first flow direction and the second flow direction are substantially orthogonal.

In some embodiments, the one or more grooves are functionalised (FIG. 1, 312(a)) to limit non-specific binding of cells in the one or more grooves. In some embodiments, the one or more grooves are functionalised with polymers (312(b)) that limit non-specific binding of cells in the one or more grooves. These polymers may be physical adsorbed or bound covalently to the substrate. They include polyethylene glycol (PEG) or PEG copolymers such as Pluronic 127. Other polymers used for passivating surfaces include carbohydrate polymers (dextran), or zwitterion antifouling polymers.

In some embodiments, the header layer further comprises a second inlet port and one or more second fluid inlets providing fluid communication between the second inlet port and the flow channel. The one or more second fluid inlets are positioned along a dimension of the flow channel which is substantially orthogonal to a longitudinal dimension of the one or more grooves so that fluid entering the flow channel from the one or more second fluid inlets flows toward the one or more second outlets in the second flow direction. Such arrangement permits both cross flow in the first direction (e.g. for perfusion of media and seeding of cells) and longitudinal flow in the second direction (e.g. for extraction of cells).

In some embodiments, the second inlet port receives fluid from one or more media sources, and the header comprises one or more second fluid channels for receiving the fluid media into the second inlet port. Preferably, the second fluid channels extend colinearly, through the header layer, the flow layer and the base layer, to form a vertical channel through the multilayer microfluidic bioreactor.

In some embodiments, the first inlet port receives fluid (such as one or both of fresh cells and culture medium) from one or more media sources, and the header comprises one or more first fluid channels for receiving the fluid media into the first inlet port. Preferably the first fluid channels extend colinearly, through the header layer, the flow layer and the base layer, to form a vertical channel through the multilayer microfluidic bioreactor.

In some embodiments, the multi-layer microfluidic bioreactor further comprises a selectively permeable membrane separating the flow channel into a first flow channel and a second flow channel, wherein the selectively permeable membrane provides for exchange of low molecular weight metabolites. In such an arrangement, the multi-layer microfluidic bioreactor may further comprise a secondary header, wherein the fluid permeable membrane is between the header and the secondary header thereby forming the second flow channel therebetween. The secondary header comprises (i) a secondary inlet port in fluid communication with the second flow channel; and optionally, (ii) a secondary outlet port in fluid communication with the second flow channel. The selectively permeable membrane provides for exchange of low molecular weight fluid metabolites entering the second inlet port and optionally, for removal of low molecular weight fluid metabolites through the secondary outlet port.

In some embodiments, the header comprises a plurality of structural posts configured to rest in abutment with the flow layer upper surface.

Alternatively/additionally, the base layer may comprise one or both of: (i) a plurality of structural posts configured to rest in abutment with the flow layer lower surface; and (ii) a wall or plurality of wall sections.

In some embodiments the multi-layer microfluidic bioreactor comprises one or more flow resistors to regulate flow in the flow channel. Flow resistors may be provided in any convenient location of the bioreactor and may be arranged upstream or downstream of the flow they regulate. Typically, the one or more flow resistors are provided in the header layer in the form of a serpentine flow path whose length determines the amount of resistance.

In some embodiments, the multi-layer microfluidic bioreactor is configured for arrangement in a stack including at least one further multi-layer microfluidic bioreactor. Each multi-layer microfluidic bioreactor in the stack comprises one or more through ports extending colinearly, typically vertically in use through each of the header layer, the base layer and the flow layer and providing fluid communication with corresponding through ports of the at least one further multi-layer microfluidic bioreactor. In some such arrangements, one or more alignment features are provided for positioning of at least one further multi-layer microfluidic bioreactor in stacked arrangement.

Viewed from another aspect, the present disclosure provides a bioreactor cell culture system for use with a plurality of multi-layer microfluidic bioreactors as disclosed herein, arranged in at least one stack. The system comprises a controller (FIG. 27 (Controller)) configured to control individually operation of one or more fluid pumps (FIG. 27, (Pump)) according to a cell culture protocol stored in a memory of the controller, the one or more fluid pumps delivering fluid to one or more through ports provided colinearly through the at least one stack, the delivered fluid entering the flow chamber of each microfluidic bioreactor in the at least one stack according to the stored cell culture protocol.

In some embodiments, the controller comprises a processor communicatively coupled with the controller memory and a user interface, wherein the memory stores instructions for performing one or more cell culture protocols, and the instructions when executed by the processor cause the controller to operate the bioreactor cell culture system to perform the one or more cell culture protocols. The processor may be configurable to control multiple cell culture processes in parallel either directly, or remotely e.g. via a cloud based server.

In some embodiments, the bioreactor cell culture system comprising one or both of: (a) a substantially rigid base plate beneath the at least one stack; and (b) a substantially rigid cover plate arranged over the at least one stack. Ideally, each of the base plate and the cover plate impart structural support to the at least one stack.

In some embodiments, the substantially rigid cover plate comprises a plurality of openings providing fluid communication between through ports in the one or more stacks and one or more fluid sources and/or waste reservoirs. Through the cover plate, ports from multiple stacks may collect into common channels for connection to required fluid sources and/or a waste reservoir.

Typically, the bioreactor cell culture system comprises one or more pumps in fluid communication with the one or more fluid sources, wherein the one or more pumps are operated by the controller to deliver fluid to individual cover plate openings in accordance with the one or more cell culture protocols.

In some embodiments, the bioreactor cell culture system comprises one or more guide features for aligning the multi-layer microfluidic bioreactors in stacked arrangement.

In some embodiments, the controller is operable cause recovery of cells from the one or more grooves of the individual multi-layer microfluidic bioreactors arranged in a stack, through a cell extraction through port extending colinearly, typically vertically in use, through the stack of multi-layer microfluidic bioreactors, and in fluid communication with the second outlet port in the individual multi-layer microfluidic bioreactors. A coupling (FIG. 12B, 391 (a))for receiving a receptacle for uncontaminated collection of extracted cells from the one or more stacks of microfluidic bioreactors may also be provided.

Viewed from another aspect, the present disclosure provides a multi-layer bioreactor sheet comprising a plurality of multi-layer microfluidic bioreactors. Each of the multi-layer microfluidic bioreactors comprises a culture chamber containing one or more grooves and one or more through ports providing for flow of fluid across the one or more grooves, wherein the one or more through ports are provided colinearly through the layers of multi-layer the bioreactor sheet.

In some embodiments, each multi-layer bioreactor sheet is configured for arrangement into a sheet stack comprising at least one other multi-layer bioreactor sheet, wherein through ports in each multi-layer bioreactor sheet in the sheet stack extend colinearly, typically vertically in use, providing fluid communication with the culture chambers of individual multi-layer microfluidic bioreactors in each multi-layer bioreactor sheet.

Viewed from another aspect, the present disclosure provides a bioreactor cell culture system for use with one or more multi-layer bioreactor sheets arranged in a sheet stack as disclosed herein, the system comprising: (a) a controller to control individually operation of one or more fluid pumps according to a cell culture protocol stored in a memory of the controller; (b) a sheet stack header (e.g., FIG. 11A, 605) providing fluid coupling between at least one fluid or waste reservoir in the bioreactor cell culture system and multiple through ports in the sheet stack requiring flow to or from the at least one fluid or waste reservoir according to the stored cell culture protocol; and (c) one or more fluid pumps delivering fluid via the through ports to individual culture chambers of the multi-layer microfluidic bioreactors in accordance with the stored cell culture protocol.

Also disclosed herein is a bioreactor cell culture system for use with one more multi-layer microfluidic bioreactors, the system comprising: a controller to control individually operation of one or more fluid pumps according to a cell culture protocol stored in a memory of the controller; a coupling header providing fluid coupling between at least one fluid or waste reservoir in the bioreactor cell culture system and a fluid port of the one or more multi-layer microfluidic bioreactors requiring flow to or from the at least one fluid or waste reservoir according to the stored cell culture protocol; and one or more fluid pumps delivering fluid via the fluid ports of the one or more multi-layer microfluidic bioreactors in accordance with the stored cell culture protocol; wherein the system is configured for use with one or more multi-layer microfluidic bioreactors comprising one or more grooves and one or more through ports providing for flow of fluid across the one or more grooves.

It is to be understood each of the various aspects described herein may incorporate features, modifications and alternatives described in the context of one or more other aspects. For instance, processes of disclosed methods may incorporate features of embodiments of a bioreactor disclosed herein, and features of such bioreactors may provide for performance of processes of methods disclosed elsewhere. For efficiency, such features, modifications and alternatives have not been repetitiously disclosed for each and every aspect although one of skill in the art will appreciate that such combinations of features, modifications and alternatives disclosed for some aspects apply similarly for other aspects and are within the scope of and form part of the subject matter of this disclosure.

The present disclosure also provides a method of culturing cells, the method comprising:

providing a microfluidic device comprising a substrate having an array of grooves that are substantially parallel;

introducing cells into one or more of the grooves;

providing a flow of culture medium over the groove array in a first flow direction that is across the grooves; and culturing the cells under conditions to, for example, support cell viability, growth or differentiation.

Advantageously providing a flow of culture medium in a first flow direction that is across the grooves (cross flow) allows for retention of the cells in the one or more grooves whilst maintaining cell viability, supporting cell growth and or cell differentiation.

The flow of the culture medium depends on the number of cells and may be provided at a flow rate equivalent to 0.2-5 mL per million cells per day, for example, at least 0.3, at least 0.4 mL, at least 0.5 mL, at least 0.6 mL, at least 0.7 mL, at least 0.8 mL, at least 0.9 mL, at least 1 mL, at least 1.1 mL, at least 1.2 mL, at least 1.3 mL, at least 1.4 mL, at least 1.5 mL, at least 1.6 mL, at least 1.7 mL, at least 1.8 mL, at least 1.9 mL, at least 2 mL, at least 2.5 mL, at least 3 mL, at least 3.5 mL, at least 4 mL, at least 4.5 mL, at least 5 mL per million cells per day. In one example the flow rate is equivalent to 0.5-1.5 mL per million cells per day, for example, 1 mL, per million cells per day.

In one example, the device can be configured with culture medium inlet and outlet ports and the average inlet velocity is set at, for example, between 0.18-0.3 mm/min, or between 0.2-0.27 mm/min, for example at about 0.22 mm/min or 0.23 mm/min. As the cells divide and expand, the inlet velocity can be increased. In one example the inlet velocity is increased by at least 40-60%, for example, by 50%, at day 3 of cell culture.

In some embodiments, the cells are introduced into one or more grooves by flow over the groove array in the first flow direction. In another or further embodiment, the cells are introduced into one or more grooves by flow in a second flow direction that is along the one or more grooves.

In one example, the device can be configured with cell inlet and outlet ports. The cells may be introduced into the device by flow from the cell inlet port and allowed to deposit into the one or more grooves (by sedimentation) under static (e.g., where the outlet port is closed) or flow conditions (where the outlet port is open allowing medium to flow out of the device).

The skilled person will appreciate that the number of cells to be introduced or loaded into the device will vary depending on the device capacity. In one example, $1 \times 10^8$ to $1 \times 10^{10}$ cells may be loaded in, for example, 50-200 mL.

In some embodiments, the cells are cultured for 1-14 days, for example, 1-10 days, 1-7 days, 1-5 days, 1-3 days, or 1-2 days.

In some embodiments, the method further comprises harvesting the cultured cells by providing a flow of extraction medium to, for example, increase shear stress so as to displace cells from the grooves and facilitate cell recovery/harvest. Generally, increasing the flow rate will increase the performance of extraction due to an increase in shear force along the base of the groove. For example, the flow of extraction medium can be provided at a shear stress of at least 0.1 dyne/cm$^2$, at least 0.2 dyne/cm$^2$, at least 0.3 dyne/cm$^2$, at least 0.4 dyne/cm$^2$, at least 0.5 dyne/cm$^2$, at least 0.6 dyne/cm$^2$, at least 0.7 dyne/cm$^2$, at least 0.8 dyne/cm$^2$, at least 0.9 dyne/cm$^2$, at least 1 dyne/cm2, for example at about 0.8 dynes/cm$^2$.

In some embodiments, the cells are harvested by flow over the groove array in the first flow direction. In another or further embodiment, the cells are harvested by flow in the second flow direction that is along the one or more grooves. Advantageously, flow in the second flow direction may increase cell viability and/or yield.

In one example, the device can be configured with cell extraction medium inlet and outlet ports and the average extraction medium inlet velocity is set at, for example, at least 10 mm/min, at least 15 mm/min, at least 20 mm/min, at least 25 mm/min, at least 30 mm/min, at least 35 mm/min, at least 40 mm/min, at least 45 mm/min, at least 50 mm/min, at least 55 mm/min, at least 60 mm/min, at least 65 mm/min, at least 70 mm/min, at least 75 mm/min, at least 80 mm/min, at least 85 mm/min, at least 90 mm/min, at least 95 mm/min, at least 100 mm/min, at least 105 mm/min, at least 110 mm/min, at least 115 mm/min, at least 120 mm/min, at least 125 mm/min, at least 130 mm/min, at least 135 mm/min, at least 140 mm/min, at least at least 145 mm/min, or at least 150 mm/min. For example, between 10-200 mm/min, or between 10-150 mm/min, for example at about 70 mm/min, about 71 mm/min, about 72 mm/min, about 73 mm/min, about 74 mm/min, about 75 mm/min, about 76 mm/min, about 77 mm/min, about 78 mm/min, about 79 mm/min, or about 80 mm/min.

The present disclosure also provides a method of transfecting/transducing cells, the method comprising:

providing a microfluidic device comprising a substrate having an array of grooves that are substantially parallel;

introducing cells into one or more of the grooves;

providing a flow of at least one exogenous molecule over the groove array in a first flow direction that is across the grooves; and incubating the cells and the at least one exogenous molecule under conditions to transfect/transduce cells with the exogenous molecule.

Advantageously providing a flow of at least one exogenous molecule (for example, viral vector) in the first flow direction that is across the groove array (cross flow) allows for retention of the cells in the one or more grooves whilst delivering the exogenous molecule to the cells received therein. The methods can result in a significant reduction in exogenous molecule (e.g., viral vector) to be provided by overcoming diffusion limitations with current systems.

In some embodiments, the cells are introduced into one or more grooves by flow over the groove array in the first flow direction.

In some embodiments, the method further comprises providing a flow of medium to wash the excess exogenous molecule from the grooves. In another or further embodiments, the method comprises providing a flow of culture medium. In some embodiments the flow of culture medium is in the first flow direction.

In some embodiments, the method further comprises culturing the cells prior to providing the exogenous molecule to, for example, to expand the number of target cells and/or to activate the cells to express one or more antigens (e.g., cell surface receptors) to, for example, facilitate uptake of a viral vector.

In another or further embodiments, the method comprises culturing the transfected/transduced cells, for example, expanding the number of transfected/transduced cells.

In some embodiments, the method further comprises harvesting the transfected/transduced cells by providing a flow of extraction medium. In some embodiments, the extraction medium is provided by flow in the second flow direction, i.e. along the grooves.

Typically, the first flow direction and the second flow direction are substantially orthogonal although this need not be the case.

The present disclosure also provides a method of selecting cells from a sample, the method comprising:

providing a microfluidic device comprising a substrate having an array of grooves that are substantially parallel, wherein the grooves comprise a capture reagent immobilized thereon that selectively captures cells; and introducing cells into one or more grooves by flow along the one or more grooves under conditions to selectively capture cells with the immobilised capture reagent.

In one example, the device can be configured with cell inlet and outlet ports and the average inlet velocity is set at, for example, at least 5-110 mm/min, at least 5-50 mm/min, at least 5-25 mm/min, for example, at about 20 mm/min, about 21 mm/min, or about 22 mm/min.

In one or a further example, the flow of cells can be provided at a shear stress of about 0.2 dyne/cm$^2$. In one or a further example, the flow of cells can be provided at a shear stress set at, for example, at least 0.05-1.14 dynes/cm2, at least 0.05-0.52 dynes/cm2, at least 0.05-0.26 dynes/cm2, for example at about 0.21 dynes/cm2, 0.22 dynes/cm2, 0.23 dynes/cm2.

In some embodiments, the method further comprises immobilising the capture reagent to the grooves. For example, the method comprises:

providing the cell capture reagent (FIG. 1, 312(a); e.g., antibody) by flow to the grooves; and incubating the groove array with the cell capture reagent for a sufficient period of time to allow the capture reagent to bind to the surface of the grooves.

In some embodiments, the capture reagent is provided by flow over the groove array in a transverse direction which is across the grooves.

In one example, the device can be configured with capture reagent inlet and outlet ports and the average inlet velocity is set at, for example, at least 0.001-30 mm/min, at least 5-30 mm/min, at least 5-20 mm/min, at least 5-10 mm/min, for example, at about 5 mm/min, about 6 mm/min, about 7 mm/min or about 8 mm/min.

In some embodiments, the method further comprises blocking the reactive groups on the surface of the grooves. For example, the method comprises:

providing a blocking reagent (e.g., Pluronic F-127) by flow to the grooves; and incubating the groove array for a sufficient period of time with the blocking reagent to block the reactive groups to, for example, prevent cells from non-specifically being retained in the grooves.

In some embodiments, the blocking reagent is provided by flow across the grooves (cross flow).

In one example, the device can be configured with blocking reagent inlet and outlet ports and the average inlet velocity is set at, for example, at least 0.001-30 mm/min, at least 5-30 mm/min, at least 5-20 mm/min, at least 5-10 mm/min, for example, at about 3 mm/min, about 4 mm/min, or about 5 mm/min.

In some embodiments, the method further comprises harvesting the unbound cells by providing a flow of extraction fluid. In some embodiments, the extraction fluid is provided by flow which is along the grooves. The extraction fluid may be cell culture medium.

In one or a further embodiment, the method further comprises providing a flow of medium to wash unbound cells from the grooves. In some embodiments, the wash medium is provided by flow along the grooves. In an alternate or further embodiment, the wash medium is provided by flow over the groove array in a direction which is across the grooves.

In one or a further embodiment, the method further comprises providing a flow of culture medium, for example to maintain cell viability or grow cells. In some embodiments, the culture medium is provided by flow along the grooves. In an alternate or further embodiment, the culture medium is provided by flow over the groove array in a direction which is across the grooves. In one embodiment, the method further comprises harvesting the transfected/transduced cells by providing a flow of extraction medium. In some embodiments, the extraction medium is provided by flow along the grooves.

In some embodiments, the method further comprises releasing bound cells from the capture reagent, for example, using papain or neuraminidase, to release bound cells from an antibody capture reagent. Such reagents may be provided by flow along the grooves or across the grooves. In some embodiments, the method further comprises culturing the released cells.

In some embodiments, the method further comprises transfecting/transducing the cells with an exogenous molecule. In some embodiments, for example, following release of bound cells, the exogenous molecule is provided by flow in a flow direction which is across the grooves. It will be appreciated that if the cells are bound, the exogenous molecule can be provided by flow along the grooves.

In some embodiments, the first flow direction is substantially orthogonal to the longitudinal dimension of the one or more grooves.

Advantageously the methods of the disclosure allow for integration of cell selection (e.g., using an antibody), gene transduction and cell expansion.

In some embodiments, the substrate is gas permeable and the device comprises one or more gas flow paths for exchange of gas across the substrate. In one embodiment, the one or more gas flow paths are beneath the gas-permeable substrate. Advantageously, this configuration allows for high density cell culture, overcoming diffusion limitations with current systems.

In some embodiments, the one or more gas flow paths are connected to an external gas supply.

In some embodiments, methods of the disclosure further comprise filling the one or more gas paths with gas, for example, prior to introducing the cells into the device.

In some embodiments, methods of the disclosure further comprise priming the device with culture medium.

In some embodiments, methods of the disclosure further comprise pressurising the device to remove trapped air bubbles by diffusion. This is driven by a gas pressure difference between the fluid and gas path.

Also disclosed herein is a microfluidic bioreactor for cell culture comprising: a flow layer comprising at least one fluid flow membrane comprising at least one groove configured for retention of cultured cells and positioned perpendicular to an axial flow of fluid; a header configured to direct flow of fluid over a top layer of the at least one flow layer and comprising at least one fluid inlet in fluid communication with the at least one flow layer and at least one fluid outlet in fluid communication with the at least one flow layer; and a bottom layer sealed to the header and configured to direct flow of fluid over a bottom side of the culture cells.

In some embodiments, the at least one inlet comprises at least one cell media inlet for fresh cell media, at least one cell media outlet for used cell media, at least one gas inlet for fresh gas, and at least one gas outlet for waste gas.

In some embodiments, the microfluidic bioreactor for cell culture also comprises a cell extraction/injection port fluidly connected to the at least one fluid inlet and configured for injection or uptake of media and cells.

In some embodiments, the at least one fluid flow membrane comprises a hydrophobic membrane configured for gas exchange and a dialysis membrane for exchange of low molecular weight metabolites. In some embodiments, the term "low molecular weight" means molecules less than substantially 10,000 Daltons such as waste products (ammonia, lactate) or metabolic substrates (glucose, amino acids).

In some embodiments, the fluid flow rate in the header and bottom layer can be independently controlled. In this way, the consumption of media can be minimised to improve cost efficiency and maximise growth efficiency to improve cell yield.

In some embodiments, the fluid flow membrane comprises a semipermeable grooved substrate for capture of non-adherent cell-types and exchange of gas and metabolites during perfusion culture positioned perpendicular to an axial flow of fluid. The semipermeable grooved substrate may be sealed between a surface modified hydrophobic membrane (manufactured from polydimethylsiloxane (PDMS)) used for gas exchange. In some embodiments, a selectively permeable membrane, such as a dialysis membrane (e.g. regenerated cellulose, polysulfone or polymer blends that contain polyvinylpyrrolidone (PVP) may be provided to exchange low molecular weight metabolites such as waste products (ammonia, lactate) or metabolic nutrients (glucose, amino acids etc.) with the flow channel so that cells can be grown at high density (e.g. 100× higher than standard tissue flask culture).

Also disclosed herein a production plant comprising a plurality of the microfluidic bioreactors for cell culture as described above, fluidly connected in parallel.

Also, there is disclosed a method of production of cultured cells comprising the steps: introducing a suspension of cultured cells into the microfluidic bioreactor for cell culture as described above; and culturing the cells in cell media and oxygen passed through the bioreactor.

Any of the features described herein can be combined in any combination with any one or more of the other features described herein within the scope of the invention.

Embodiments of the present disclosure relate to a multi-layer microfluidic bioreactor design and process for scalable cell manufacturing processes, for use in for delivery of cell and gene therapy. Embodiments of the disclosure provide for automation of cell selection, gene transfer, and culture expansion within a closed system that can be cost-effectively scaled for clinical therapies. Grooved semipermeable substrates can capture and grow cells using perfusion culture methods; microfluidic geometry directs flow over grooves for cell expansion culture and typically, flow along grooves for cell harvesting or cell selection; and integration of cell selection (using monoclonal antibody), gene transduction and cell expansion processes is made possible using embodiments of the microfluidic design. Embodiments of the disclosure provide a multi-layer microfluidic bioreactor optimised for high density and automated growth of mammalian cells in cell culture media.

BRIEF DESCRIPTION OF DRAWINGS

The present invention will now be described in greater detail with reference to the accompanying drawings. It is to be understood that the embodiments shown are examples only and are not to be taken as limiting the scope of the invention as defined in the claims appended hereto.

FIGS. 12A to 12C are isometric, top and side views of a cover plate according to an embodiment of the disclosure.

FIG. 29A) Pluronic F127 preceding physical adsorption of antiCD3 moAb. FIG. 29B) AntiCD3 moAb without Pluronic F127 treatment. FIG. 29C) Pluronic F127 following physical adsorption of antiCD3 moAb.

DETAILED DESCRIPTION

Figure 1:
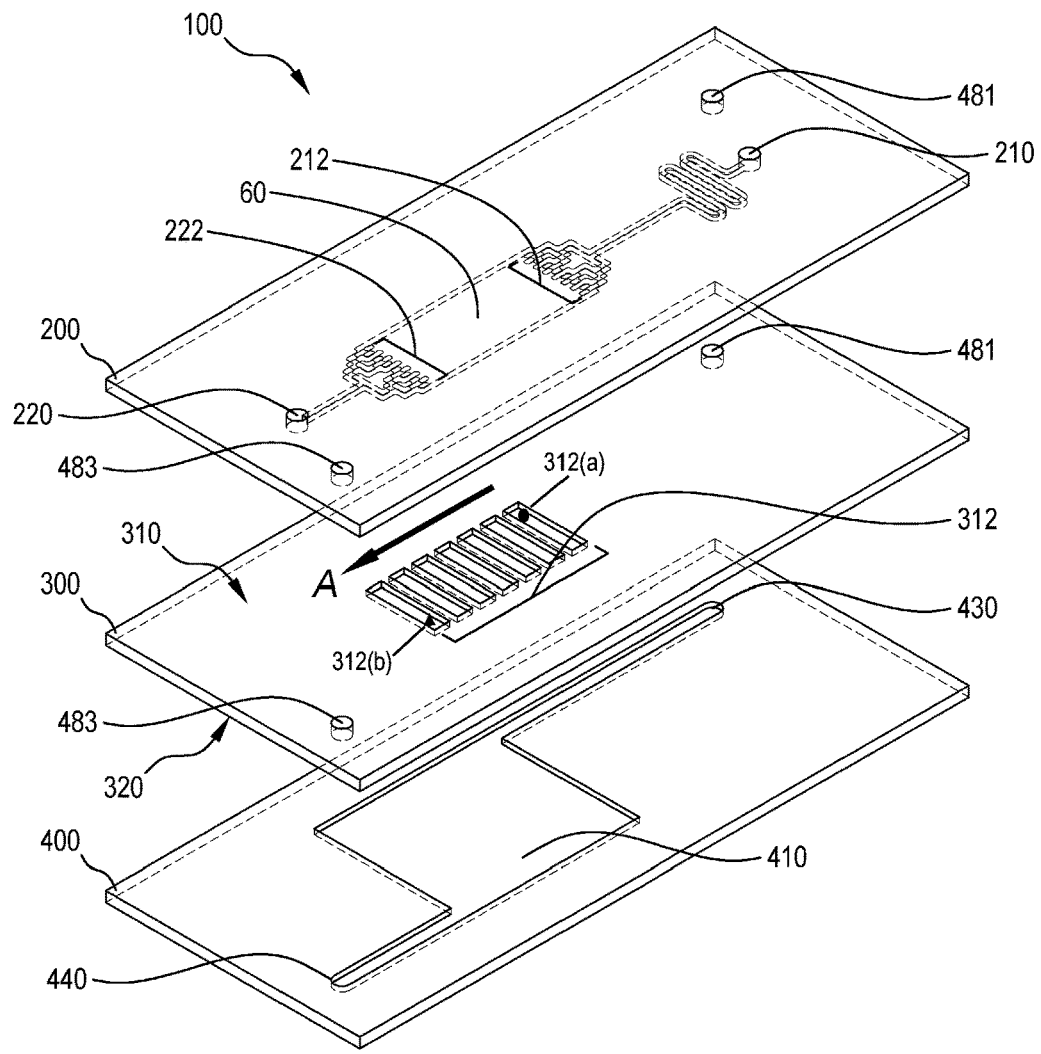
FIG. 1 is an exploded schematic view of a multi-layer microfluidic bioreactor according to one embodiment, showing cross flow of fluid in a first flow direction A (cross flow).

Referring firstly to FIG. 1, there is shown an exploded schematic view of a multi-layer microfluidic bioreactor ("bioreactor") 100 provided for cell culture according to an embodiment of the disclosure. Bioreactor 100 comprises a header layer 200, a base layer 400 and a fluid permeable flow layer 300 which is located between the header layer and the base layer.

Figure 2:
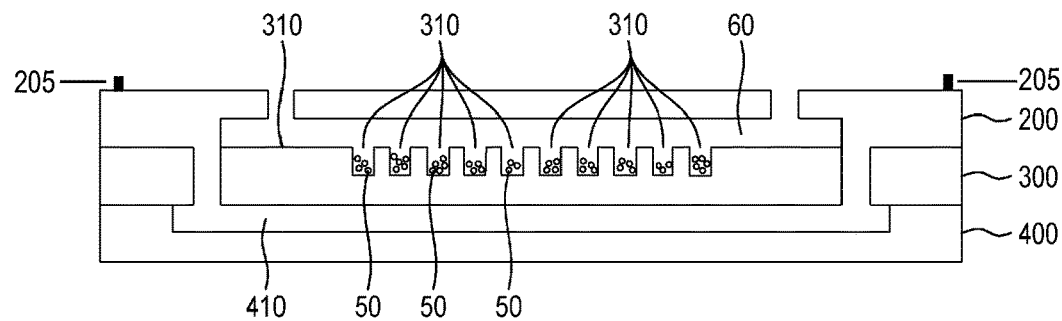
FIG. 2 is a sectional schematic representation of the bioreactor of FIG. 1.

Flow layer 300 comprises an upper surface 310 and lower surface 320, and the upper surface comprises at least one and typically several grooves 312 forming a groove array in the flow layer upper surface for retention of cells 50 (FIG. 2). Base layer 400 is sealed to header layer 200 either directly e.g. by bonding to a base layer flange surrounding flow layer 300, or indirectly by bonding together each of the three layers of the bioreactor. Base layer 400 provides a gas flow path 410 for gas exchange across gas permeable flow layer 300. Respiratory gases (air+10% $CO_2$) enter gas flow path 410 through gas inlet port 430 and expired gases escape through gas outlet port 440.

Since flow layer 300 is gas permeable, gases in gas flow path 410 perfuse through the grooved layer where they are exchanged with cells 50 retained in flow channel 60. Additionally, gases contained within the media circulated through flow channel 60 are also taken up by cells 50.

Header layer 200 has a first inlet port 210 which feeds one or more first fluid inlets 212 to flow channel 60 which is formed between the lower surface 320 of header 300 and the upper surface of the flow layer. Thus, grooves 312 form the floor of a media chamber in which cells 50 deposit and grow. Typically, first inlet port 210 facilitates delivery of cells and culture medium through first inlets 212. One or more first fluid outlets 222 located at the opposite side of flow channel 60 provide fluid communication with first outlet port 220 which is provided to facilitate removal of waste fluid. In some embodiments, cell harvesting may also occur via outlet port 220.

First fluid inlets 212 and first fluid outlets 222 are positioned in the header such that fluid entering the flow channel 60 moves in a first flow direction A from the fluid inlets toward the fluid outlets such that flow is directed across the grooves 312. This cross flow direction can be used to load cells into one or more of the grooves 312. Cells are introduced into flow channel 60 by flow, and deposit into one or more grooves by sedimentation due to the difference in density of the cell and surrounding fluid even under flowing conditions. Cells deposit in regions of low shear stress and are retained there by depositional and hydrodynamic forces even under flow conditions. Cell culture medium can be provided across the top of the grooves 312 to provide nutrients and growth factors for cell metabolism and remove the waste products generated by the cells retained therein without displacing the cells.

Flow rate modulates the transport and deposition of cells into the grooves 312. In one example, the cross flow rate is such that cells introduced by cross flow deposit into one or more grooves 312 near the fluid entrance. The skilled person will appreciate that cell deposition will also be a function of the cell size and cell density and properties of the fluid in which they are carried. Similarly cell retention within the grooves is controlled by cell concentration and flow rate. The Reynolds number and device geometry (e.g., groove depth) will also impact on cell retention. The Reynolds number is directly proportional to the cross flow velocity and inversely related to the plate separation. During cross flow, the retention of cells in the device will depend on the volume of flow recirculation in the base of grooves, which can be determined by fluid dynamic simulation. As the cells expand to fill the groove, they will be displaced from the groove, flow across the flow channel 60 and deposit by sedimentation into an adjacent groove until the groove array is filled.

In the arrangement shown in FIGS. 1 and 2, flow is in direction A, or "cross flow" which is across the longitudinal dimension of grooves 312 in flow layer 300. Typically, this cross flow is orthogonal (90°) to the longitudinal dimension of grooves 312 although it is also contemplated that cross flow need not be precisely orthogonal to achieve the beneficial effects of delivering cells and culture medium using cross flow. In an embodiment, the angle of cross flow is in the range of approximately 75° to 90° relative to the longitudinal dimension of the grooves, preferably approximately 80° to 90°, more preferably approximately 85° to 90°. In an embodiment, the cross flow is approximately 90° relative to the longitudinal dimension of the grooves.

Figure 3:
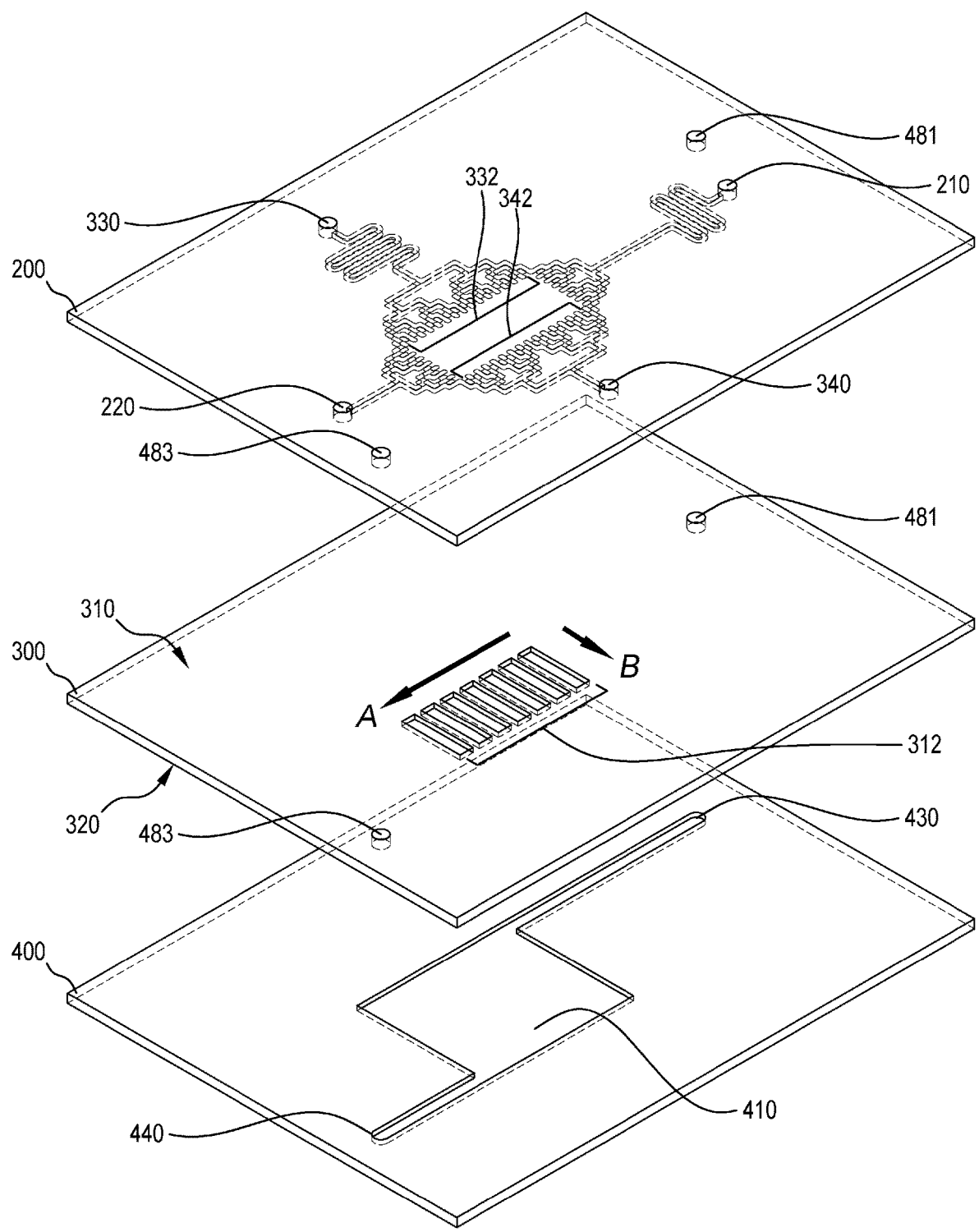
FIG. 3 is an exploded schematic view of a bioreactor which provides for flow in first flow direction A and in a second flow direction B (longitudinal flow).

FIG. 3 is an exploded schematic view of a bioreactor 100 according to another embodiment of the disclosure which provides for flow in first flow direction A (cross flow), and flow in a second flow direction B which corresponds to the longitudinal dimension of grooves 312 (longitudinal flow). Here, header layer 200 additionally comprises a second inlet port 330 which feeds one or more second fluid inlets 332 to flow channel 60. The one or more second fluid outlets 342 are located at the opposite side of flow channel 60 to second fluid inlets 332 and provide fluid communication with second outlet port 340 which is provided for removal of cells from the flow channel. In the embodiment illustrated in FIG. 3, first inlet port 210 delivers fluid containing cells and culture medium into flow channel 60, waste is removed via first outlet port 220 and a cell extraction fluid (also referred to herein as "extraction medium") is delivered via second fluid inlet port 330 to wash cultured cells along grooves 312 for removal through second fluid outlets 342 and second fluid outlet port 340. It is to be understood however, that second inlet 330 port need not be provided, and first fluid inlet port 210 may additionally deliver a cell extraction fluid for washing cultured cells along grooves 312 for removal through second fluid outlets 342 and second fluid outlet port 340. In both arrangements, removal of cells via second fluid outlet port 340 is along grooves 312 in a longitudinal flow direction B, enabling the cells to be displaced from the grooves efficiently, for removal through second fluid outlets 342.

Figure 4:
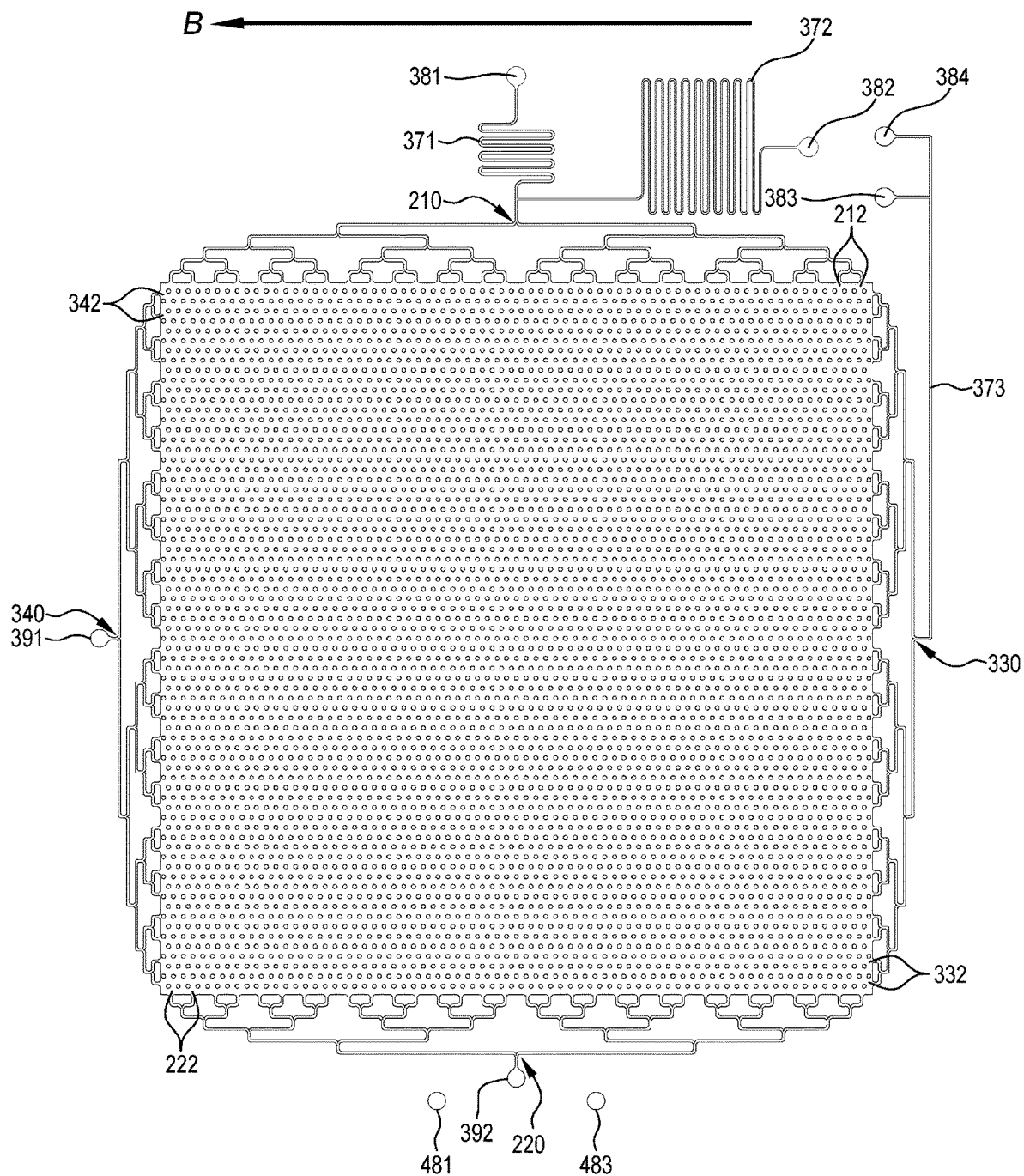
FIG. 4 illustrates the lower surface (underside) of a bioreactor header layer according to an embodiment of the disclosure.

For clarity, a further embodiment showing both cross flow and longitudinal flow is presented in FIG. 4, which illustrates the lower surface, or underside, of header layer 200. Second outlet port 340 is in fluid communication with flow channel 60 via one or more second fluid outlets 342. In the embodiment shown, pairs of second fluid outlets 342 join to form a fluid flow path which in turn joins a fluid flow path from an adjacent pair of fluid outlets in a branched arrangement which ultimately connects all fluid outlets 342 with second outlet port 340. In this arrangement, it is possible to achieve removal of cells 50 by flow along grooves 312 in a second flow direction B (longitudinal flow). In a manner similar to the embodiment shown in FIG. 3, fluid including cells and culture media may enter via first inlet port 210, with cells propagating across and into grooves 312 with culture media in the flow channel flowed in direction A. At the conclusion of the cell culture process, cells may be removed through second outlet port 340 such that cultured cells are displaced along the grooves 312 to second outlet port 340. Laminar flow along the grooves 312 displaces the retained cells 50 toward second outlet port 340 so they can be collected in a sealed receptacle for removal from the bioreactor.

As would be understood by one of skill in the art, the term "port" as it is used herein in the context of "inlet ports" and "outlet ports" is to be broadly to construed as part of a flow path that provides for the flowing in our flowing out of fluid relative to the flow channel 60. For example, first fluid inlet port 210 may be provided as an aperture (FIG. 1) that provides for flowing in of fluid by direct fluid coupling with a first fluid source by a tube or the like (not shown). Alternatively, first fluid inlet port 210 may be provided as a junction (FIG. 4) in a fluid flow path that provides for flowing in of fluid by a more indirect fluid pathway in fluid communication with first through bores 381, 382.

Also shown in FIG. 3 is a second inlet port 330 in fluid communication with one or more second fluid inlets 332 providing fluid communication with flow channel 60. The one or more second fluid inlets 332 are positioned along a dimension of the header which is orthogonal to the longitudinal dimension of the one or more grooves 312 so that fluid entering flow channel 60 from the one or more second fluid inlets 332 flows toward the one or more second fluid outlets 342 in the second fluid direction B. A zoomed in isometric view of the lower right corner of the header layer underside (FIG. 4) is presented in FIG. 5 which shows 6 layers of bifurcation of the fluid flow channel from second inlet port 330, finally opening via second fluid inlets 332 into flow channel 60. Similarly, FIG. 5 shows first fluid outlets 222 in fluid communication connected by layered junctions, forming a tree structure ultimately providing a common fluid pathway to the first outlet port 220.

Figure 5:
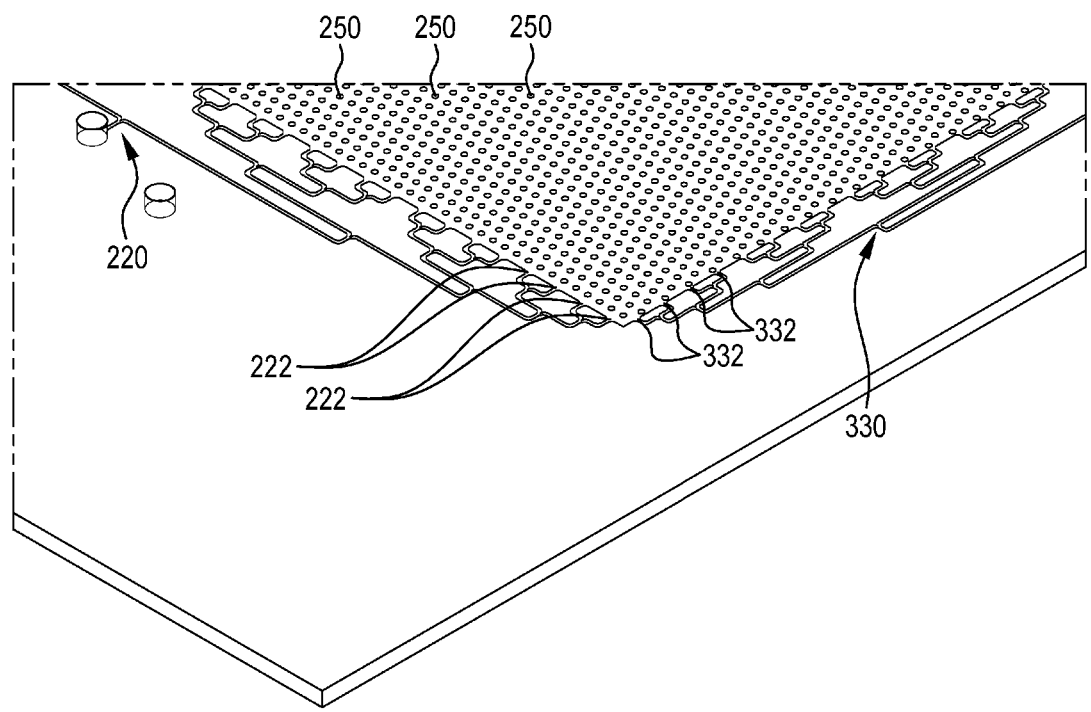
FIG. 5 is a zoomed in isometric view of the lower right corner of the header layer in FIG. 4.

Also shown in FIGS. 4 and 5 are structural posts 250 which, in some embodiments, are provided in the underside of header 200. Structural posts 250 are configured to rest in abutment with the flow layer upper surface 310, on the substrate surrounding and spanning between grooves 312. In certain embodiments, one or more of the header layer 200, flow layer 300 and base layer 400 may be manufactured from an elastomeric material such as silicone rubber (PDMS). Structural posts 250 may be incorporated into the design of header 200 to impart structural support to ensure patency of flow channel 60 and grooves 312 during use. In some embodiments, header layer 200 and/or base layer 400 may be manufactured from a thermo-plastic material which provides greater rigidity and may therefore require fewer structural posts to ensure patency of flow channel 60 and grooves 312 during use. Suitable thermo-plastic materials may include but are not limited to Cyclic olefin copolymer (e.g., Zeonor® 1060R), polytetrafluoroethylene (PTFE), polyhetheretherketone (PEEK), polystyrene, and polycarbonate to name a few.

Figure 6:
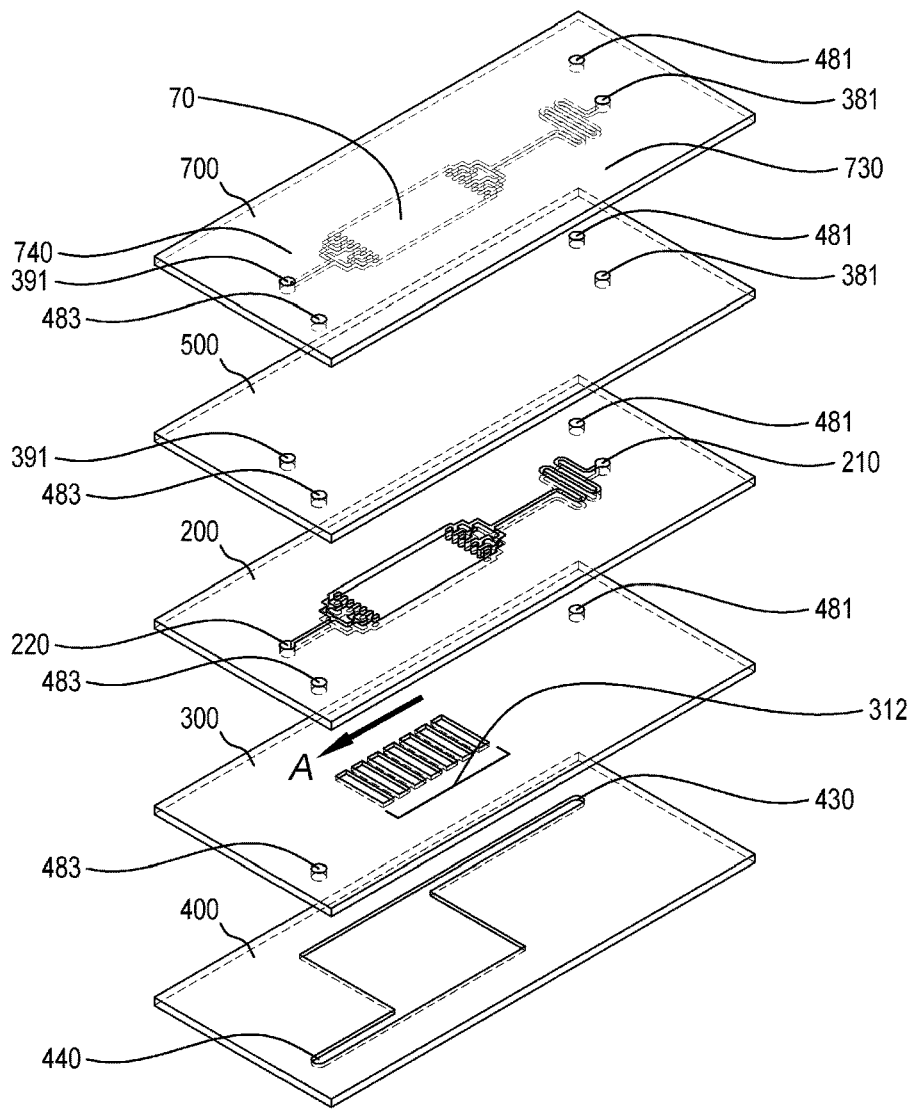
FIG. 6 is an exploded schematic view of a bioreactor comprising a selectively permeable membrane and in which there is cross flow.
Figure 7:
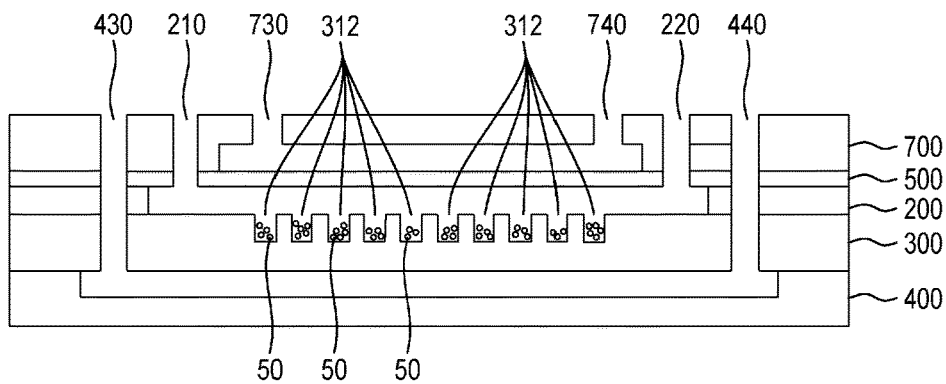
FIG. 7 is a sectional schematic representation of the device in FIG. 6.

Another embodiment of the disclosure is presented in the schematic illustration of FIG. 6 which further comprises a selectively permeable membrane 500 which functionally separates flow channel 60 into two parallel flow channels across which low molecular weight metabolites can exchange. In some embodiments, selectively permeable membrane 500 may be manufactured from a dialysis membrane or similar membrane material. Suitable membrane materials include but are not limited to regenerated cellulose, polysulfone and polymer blends including polyvinylpyrrolidone (PVP). In one embodiment, selectively permeable membrane 500 comprises a dialysis membrane having pore size suitable for exchanging molecules having a molecular weight of less than 20 kD, more preferably less than 15 kD and more preferably still, less than 10 kD. In this arrangement, the selectively permeable membrane 500 separates secondary header 700 and header 200, forming a second flow channel 70. Cells enter flow channel 60 via first inlet port 210 and deposit into grooves 312. Fluid, typically base medium containing nutrients with molecular weight less than 10 kD, enters second flow channel 70 via secondary inlet port 730 and exits via secondary outlet port 740, where molecules less than 10 kD diffuse across membrane 500 entering flow channel 60 for nutrient delivery to cells in grooves 312. Metabolic waste molecules generated by cells in grooves 312 diffuse across membrane 500, enter flow channel 70 and exit via secondary outlet port 740. Meanwhile, growth medium enters flow channel 60 via first inlet port 210. Waste product is removed from flow channel 60 via first outlet port 220. In some embodiments, secondary outlet 740, need not be provided since all waste product may exit through first outlet port 220. However this may lead to cell damage and thus may not be desirable. As in the embodiment of FIG. 1, FIG. 6 provides for cross flow of cells and media in direction A. Through bore 381 provides a vertical channel for delivery of cells; through bore 391 provides a vertical channel for removal of cells. Through bores 481, 483 provide vertical channels for delivery and removal of gas. FIG. 7 provides a sectional view of the device in FIG. 6.

A benefit associated with provision of selectively permeable membrane 500 is that delivery of fluid into second flow channel 70 can be controlled separately from delivery of fluid into flow channel 60 allowing for differential flow rates in channel 70 and channel 60 e.g. higher flow rates for base medium than growth medium. This can reduce quantities of growth media required, resulting in cost savings.

Figure 8:
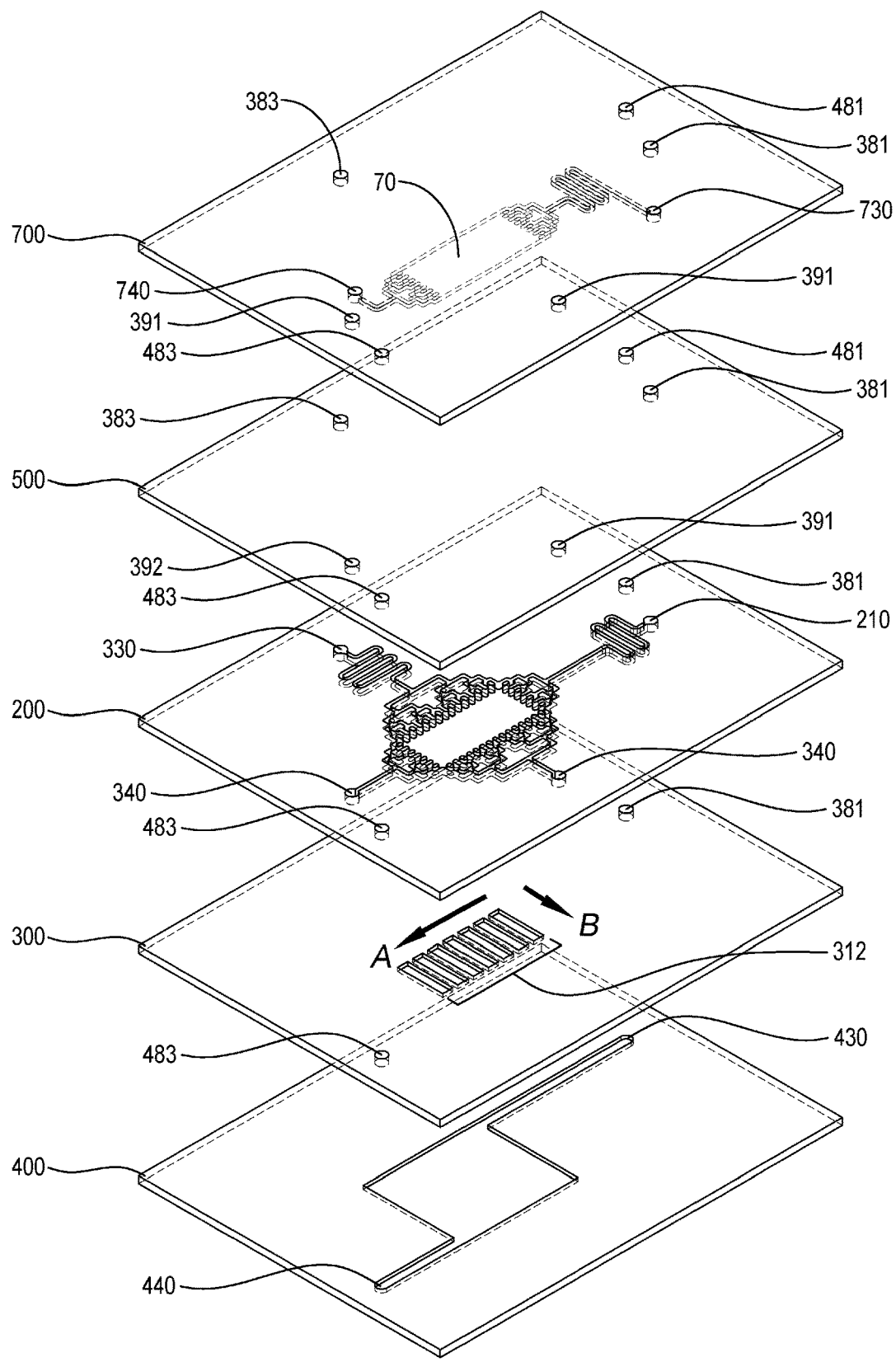
FIG. 8 is an exploded view of a bioreactor comprising a selectively permeable membrane and in which there is cross flow and longitudinal flow.

FIG. 8 illustrates yet another embodiment, comprising a selectively permeable membrane 500 in which there is both delivery of cells and media in cross flow direction A, as well as removal of cells in longitudinal flow direction B, since header 200 comprises second outlet port 340 which provides for longitudinal flow of cells along grooves 312 in flow direction B. In the embodiment shown, second inlet port 330 is also provided for delivery of cells, and other reagents required for cell culture protocols using bioreactor 100, examples of which are provided herein. It is to be noted that in the embodiments in FIGS. 6 to 8, there is a void formed through the full thickness of header layer 200 which together with the upper surface 310 of flow layer 200 and lower surface of the permeable layer 500, defines the flow channel 60. Through bore 381 provides a vertical channel for delivery of cells, through bore 383 provides a vertical channel for removal of cells, and through bores 481, 483 provide vertical channels for delivery and removal of gas.

Notably, FIGS. 1, 3, 6 and 8 show gas input channel 481 and gas output channel 483 as through bores forming a vertical channel through header layer 200 and flow layer 300 for delivery of respiration gases to gas flow path 410 and removal of expired gases. In some embodiments, through bores are provided forming vertical channels for delivery of fluid to each of the inlet ports, and removal of fluids from each of the outlet ports in the bioreactor, each of the through bores extending colinearly through all three layers of the bioreactor 100, and each fluid outlet is in fluid communicating with a corresponding channel.

Figure 9:
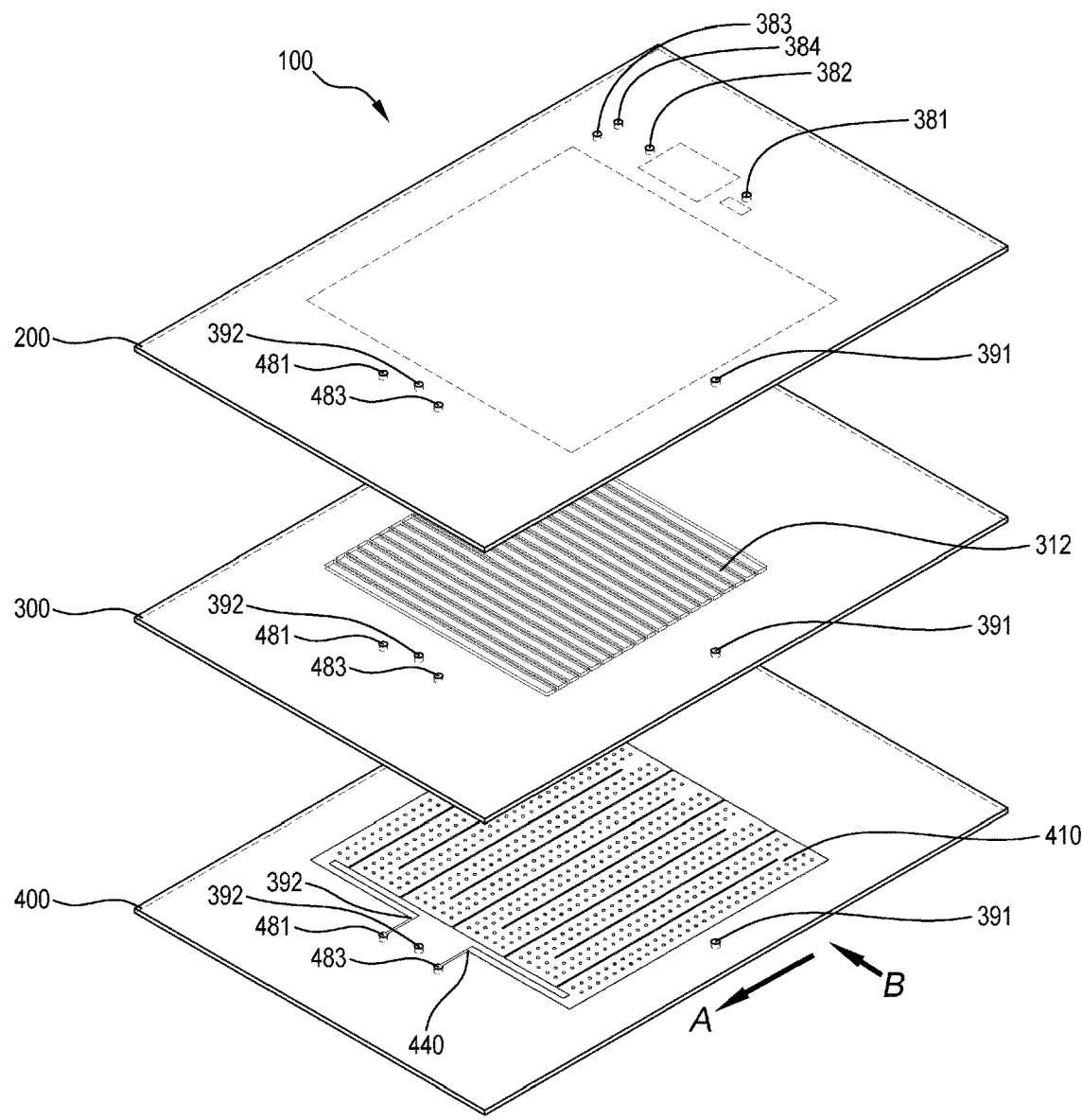
FIG. 9 is an exploded view of a bioreactor according to another embodiment of the disclosure.

FIG. 9 is an exploded view of a bioreactor 100 according to another embodiment, incorporating header layer 200, flow layer 300 and base layer 400. Although not visible, the features of header 200 correspond to the features described in relation to FIG. 4. Block 312 in flow layer 300 represents the elongate parallel grooves extending in direction B. Base layer 400 includes gas inlet 430 and gas outlet 440 which feed gas flow path 410. Additionally, a number of through bores are shown. In the embodiment shown, through bores 381, 382 provide a vertical channel for delivery of cells and culture media, respectively, to first inlet port 210 (although they may alternatively be delivered via separate inlet ports, as in FIGS. 6 to 8). Through bores 383 and 384 provide a vertical channel for delivery of cells and extraction fluid, respectively, to second inlet port 340 (although they too, may be delivered via separate inlet ports). Through bores 391 and 392 provide a vertical channel for extraction of cells and removal of expired media, respectively.

Figure 10:
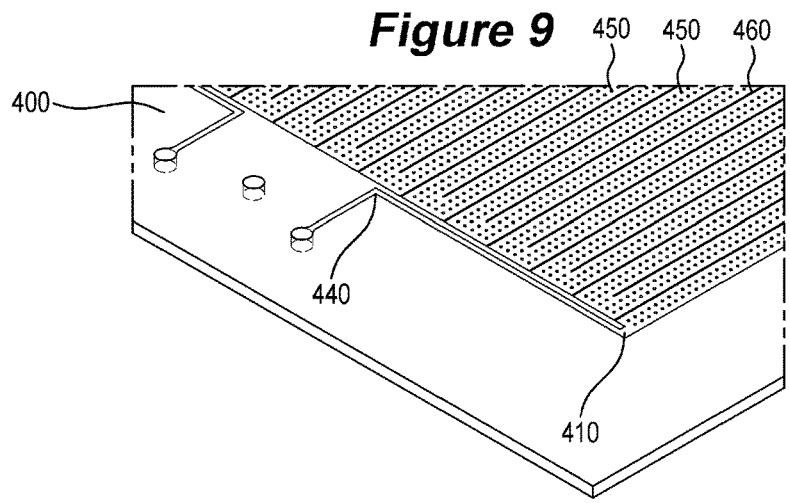
FIG. 10 is a zoomed isometric view of the lower right corner of the base layer in FIG. 9.

FIG. 10 is a zoomed isometric view of the lower right corner of the base layer 400 from FIG. 9. This view shows structural posts 450 in base layer 400 which are configured to rest in abutment with the lower surface 320 of flow layer 300 to impart structural support and ensure patency of the gas flow path 410 during use. Additionally, a serpentine wall 460 directs gas flow in a serpentine path from gas inlet port 430 to gas outlet port 440. However, it is to be understood that wall 460 may be provided in wall portions or sections, or need not be provided at all with the gas simply flowing from gas inlet port 430 to gas outlet port 440. In some embodiments the structural posts 450 may alternatively/additionally be omitted where the bioreactor dimensions and/or materials are such that collapse of fluid flow pathways is low.

In some embodiments, the bioreactor further comprises one or more alignment features such as a tongue or protrusion (FIG. 2, 205) on the top layer of the bioreactor (header 200 or secondary header 700) which cooperates with a corresponding groove or notch in the bottom surface of the base layer 400 (or vice versa).

Microfluidic devices require very precise control of flow, particularly for cell deposition and cell separation processes. Pneumatically controlled flow is preferable to syringe pumps or roller pumps since flow rate depends on the hydraulic resistance of flow resistors rather than the compressibility of the fluid. Thus, in some embodiments flow resistors are incorporated into the fluid pathways to govern rate of perfusion. Best shown in FIG. 4, flow resistor 371 regulates the rate of flow of fluid typically containing cells, from vertical channel 381 into first inlet port 210 and further, into flow channel 60 via first fluid inlets 212. Flow resistor 372 regulates the rate of flow of fluid, typically containing culture medium, from vertical channel 382 into first inlet port 210 and further, into flow channel 60 via first fluid inlets 212. Flow resistor 373 (providing approximately equivalent resistance to flow resistor 371 owing to its length) regulates the rate of flow from vertical channels 383 and 384, delivering fluid typically containing cells and extraction fluid respectively, into second inlet port 330 and further, into flow channel 60 via second fluid inlets 332.

It is to be understood that the nature and location of flow resistors shown in the embodiments herein are examples only. While the flow resistors are typically incorporated into header layer 200, their location may be upstream or downstream of flow channel 60, and their arrangement may be serpentine or elongate as shown, or coiled, directed along or around the header substrate or in other arrangements as would be understood by one of skill in the art. In some instances, the nature and location of the one or more flow resistors may be determined, at least in part, by the size and dimensions of the footprint of the substrate layers from which the bioreactor 100 is constructed and/or limitations of manufacture.

Figure 11A:
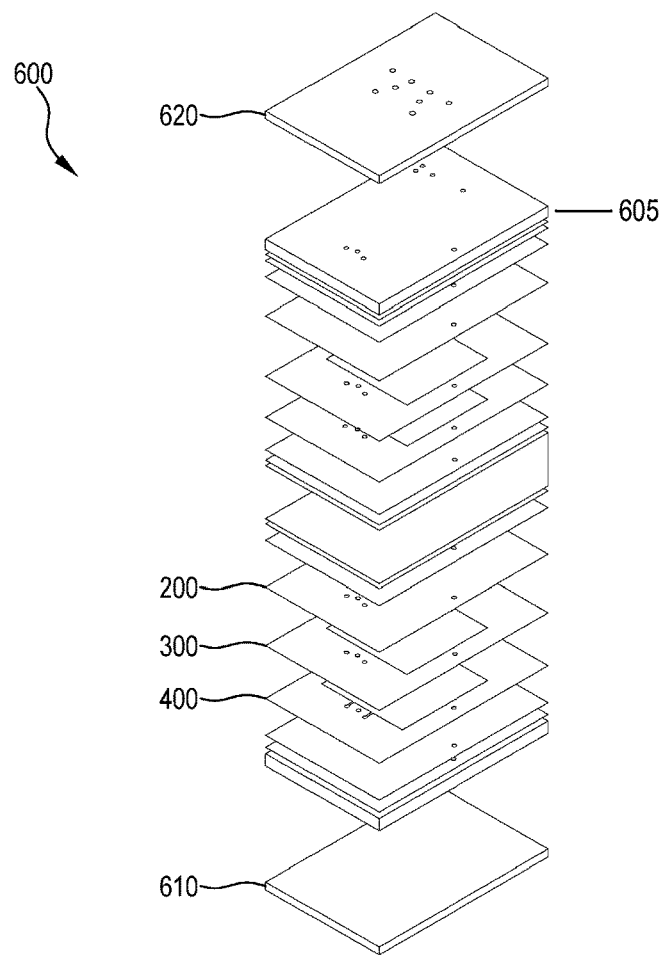
FIGS. 11A and 11B show a plurality of bioreactors arranged in a stack in exploded and assembled views respectively.
Figure 11B:
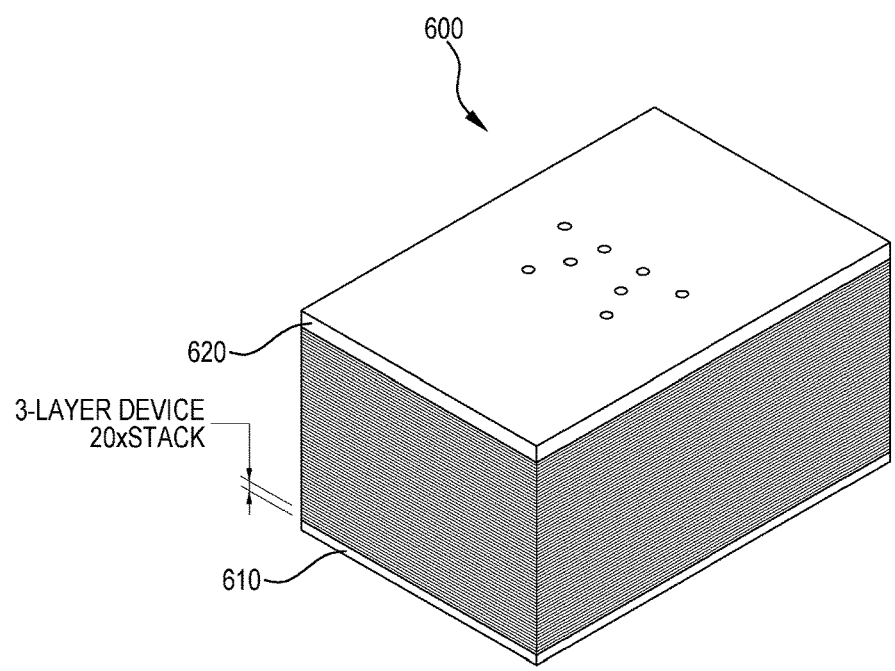

FIGS. 11*a* and 11*b* show a plurality of bioreactors 100 arranged in a stack 600 in exploded and assembled views respectively. The stack includes a substantially rigid base plate 610 and a substantially rigid cover plate 620 to impart structural support to the stack. In preferred embodiments, guide features such as posts (not shown) extend through colinear post channels (not shown) provided through the plurality of bioreactors to ensure alignment and flow patency in through bores forming fluid input channels 381, 382, 383, 384, fluid output channels 391, 392, gas input channel 481 and gas output channel 483 of the individual bioreactors. FIGS. 11*a* and 11*b* illustrate a stack of twenty multi-layer microfluidic bioreactors 100 with the 3-layered design shown in FIG. 9. Layers 200, 300 and 400 from a single multi-layer microfluidic bioreactor are shown on the exploded view (FIG. 11*a*). Advantageously, all twenty bioreactors are supplied by a common fluid source for each fluid required for the cell culture process. It is to be understood, however, that a stack of bioreactors could comprise a single bioreactor, or e.g. 5, 10, 20, 30, 50, 60, 70, 80, 90, 100 or 100's of bioreactors.

The embodiment illustrated in FIGS. 11*a* and 11*b* may be used to select for CD34+ cells which typically occur with a 1% frequency in mobilized peripheral blood mononuclear cells. For example, $2 \times 10^9$ cells could be deposited into the grooves and grow in grooves at a density around $3.5 \times 10^8$ cells/ml, with 200 grooves per layer. In one example, 4 stacks each with 25×3 layers could be utilised to purify $10^{10}$ cells and expand $10^{10}$ cells from a 1% CD34+ cell fraction (×100 expansion).

In some embodiments, bioreactors 100 are manufactured in multi-layer sheets, each containing a plurality of bioreactors. In the embodiment shown in FIG. 18, the flow layer of four bioreactors 100 has been formed a single A5 size PDMS sheet. The flow layer sheet may be assembled with a corresponding header layer sheet and base layer sheet and bonded to form a multi-layer sheet comprising 4 individual bioreactors. Multiple bioreactors may be arranged on sheets according to layouts and sheet sizes as may be determined by manufacturers or for optimised design or consumption of materials. The sheet may be cut to form individual multi-layer bioreactors, or the multi-layer sheets themselves may be stacked to form a sheet stack. Each bioreactor in each sheet in the stack has through ports provided colinearly which, when the stacks are assembled, extend vertically to deliver fluid to individual ones of the bioreactors in the manner discussed in relation to the stack 600.

Advantageously, because the bioreactors are connected in parallel through vertical bores forming fluid input and fluid output channels, each individual bioreactor in the stack can be supplied by a single source of each of the required fluids, and waste can be collected from all bioreactors in the stack into a single waste receptacle. Corresponding fluid inlets and outlets in adjacent bioreactors in a sheet stack may be fluidly coupled by a suitably arranged manifold, still requiring only a single source of each of the required fluids, and a single waste receptacle.

FIGS. 12*a* to 12*c* illustrate in further detail an example of a cover plate 620 having a plurality of openings in a top surface 610 for receiving tubing for coupling the stack 600 to fluid sources and/or waste reservoirs. In the embodiment shown, cells may be delivered from a single bag, container, flask or other receptacle to all bioreactors in the stack by connecting a tube (not shown) with opening 681 which in turn supplies each of the bioreactors through fluid input channel 381. Culture medium may be delivered from a single bag, container flask or other receptacle to all bioreactors in the stack by connecting a tube (not shown) with opening 682 which in turn supplies each of the bioreactors through fluid input channel 382. In a protocol requiring cell separation, cells may be delivered to all bioreactors in the stack by connecting a tube (not shown) with opening 683 which supplies each of the bioreactors through fluid input channel 383. An extraction fluid may be delivered to all bioreactors in the stack from a supply (bag, container, flask or the like) by connecting a tube (not shown) with opening 684 which in turn supplies each of the bioreactors through fluid input channel 384. Respiratory gases such as oxygen may be supplied through opening 641 either by an open connection to atmosphere, or using a pump to drive atmospheric air or gas from a canister, under pressure through gas input channel 481 for supply to the gas flow path 410 in each of the bioreactors.

In a preferred embodiment, one or more stacks 600 of the type illustrated in FIGS. 11*a* and 11*b* are incorporated into a bioreactor cell culture system. Ideally, the cell culture system has a housing containing the stack(s) and fluid sources, in the form of plurality of reagent bags or containers containing the reagents necessary to perform cell culture protocols and which are fluidly coupled to the stacks through a manifold such as cover plate 620. The system includes a controller which comprises a processor communicatively coupled with the controller memory and a user interface which is ideally incorporated into the housing and may comprise a touch screen, and/or display and keypad accessible to an operator of the system. The memory stores instructions for performing one or more cell culture protocols, and the instructions, when executed by the processor, cause the controller to operate the bioreactor cell culture system to perform the one or more cell culture protocols.

Inside the housing is one or more fluid pumps in communication with the one or more fluid sources. The pumps are operated by the controller to deliver fluid to individual cover plate openings in accordance with cell culture protocols stored the controller memory by controlling opening and closing of valves in the fluid lines. In some embodiments, the processor comprises a microcontroller configured to independently regulate pressure sources coupled to the bioreactor inputs.

The user interface receives one or more inputs from an operator to select from the memory, or to input to the memory, one or more cell culture protocols. Each culture protocol has a corresponding set of instructions stored in memory which, when executed by the processor, cause the controller to operate the pumps and other components of the system according to the selected/entered protocol.

For example, the controller is operable to cause extraction of cells from the grooves of individual bioreactors through a cell extraction channel extending colinearly through the stack and in fluid communication with the second outlet port in the individual bioreactors. Ideally, the housing includes a platform or area for receiving a receptacle such as a bag, flask or vial which is coupled to the extraction channel for uncontaminated collection of extracted cells.

In some embodiments, the controller has internet connectivity via Wi-Fi or Ethernet connection enabling remote access to the processor for access to data, modification and control of protocols, and remote software updates. Additionally, the controller may be operatively coupled with a scanner or other device to automatically read or receive from a sample an identifier such as a barcode or electronic tag for secure tracking of patient material and customisation of protocols for each patient.

Cell Deposition into One or More Grooves of a Groove Array

The present disclosure provides methods that comprise introducing cells into one or more grooves of a groove array. Cells can be introduced by flow across the grooves (cross flow orthogonal to the longitudinal dimension of grooves) or flow along the grooves (longitudinal flow). Cells are deposited by sedimentation due to the difference in density of the cell and surrounding fluid under flowing or static conditions. Before introducing the cells into the groove array, the device may first be primed by flowing culture medium (cross flow and/or longitudinal flow) into the device until it is filled. The cells may be present in bodily fluids (e.g. blood), processed or partially processed bodily fluids (e.g., blood processed to remove platelets and/or serum), or resuspended in an appropriate fluid medium (e.g., culture medium) before being introduced into the device.

The device can be configured with cell inlet and outlet ports. If depositing the cells into one or more grooves under static conditions the outlet port will be closed following inoculation of the cells by flow from the inlet port.

The cells may be prokaryotic cells or eukaryotic cells. The cells may be from a single-celled organism or a multi-celled organism. In some cases, the cells are genetically engineered, e.g., the cells may be chimeric cells. The cells may be bacterial, fungi, plant, or animal cells, etc. The cells may be from a human or a non-human animal or mammal. For instance, if the cell is from an animal, the cell may be a cardiac cell, a fibroblast, a keratinocyte, a hepatocyte, a chondrocyte, a neural cell, an osteocyte, an osteoblast, a muscle cell, a blood cell, an endothelial cell, a stem cell, an immune cell (e.g., a T-cell, a B-cell, a macrophage, a neutrophil, a basophil, a mast cell, an eosinophil), etc. In some cases, the cell is a cancer cell. The cells may be non-adherent cell lines (e.g. L1.2, mouse immune B; Jurkat, human $CD4^+$ T; Ramos, human immune B) or adherent cell lines (GPE86, mouse embryonic fibroblast), as well as primary cells. In a preferred embodiment, the cell is a primary cell such as a primary immune cell or stem cell. In one embodiment, the cell is a primary immune cell, for example, a T cell. In one embodiment, the cell is non-adherent and the culture methods are for culture of cells in suspension. In another embodiment, the cell is adherent and culture methods are for culture of adherent cells in suspension.

As used herein, the term "immune cells" refer to cells of the immune system, which defend the body against disease and foreign materials. Non-limiting examples of immune cells include dendritic cells, such as bone marrow-derived dendritic cells; lymphocytes, such as B cells, T cells, and natural killer cells; and macrophages. The immune cells may, in some embodiments, be derived from bone marrow, spleen, or blood from a suitable subject. For example, the immune cells may arise from a human or a non-human mammal, such as a monkey, ape, cow, sheep, goat, horse, donkey, llama, rabbit, pig, mouse, rat, guinea pig, hamster, dog, cat, etc. In a preferred embodiment, the immune cell is a T-cell, preferably a human T-cell.

As used herein, the term "stem cells" refers to clonogenic cells capable of both self-renewal and multilineage differentiation. Based on their origin, stem cells are categorised either as embryonic stem cells (ESCs) or as postnatal stem cells/somatic stem cells/adult stem cells (ASCs).

Embryonic stem cells (ESCs) can be derived from embryos that are 2-11 days old called blastocysts. They are totipotent—capable of differentiating into any type of cell including germ cells. ESCs are considered immortal as they can be propagated and maintained in an undifferentiated state indefinitely.

Adult stem cells (ASCs) are found in most adult tissues. They are multipotent—capable of differentiating into more than one cell type but not all cell types. Depending on their origin, AASCs can be further classified as hemopoetic stem cells (HSCs) and mesenchymal stem cells (MSCs). HSCs can be obtained either from cord blood or peripheral blood. MSCs are those that originate from the mesoderm layer of the fetus and in the adult reside in a variety of tissues such as the bone marrow stem cells (BMSCc), limbal stem cells, hepatic stem cells, dermal stem cells, etc.

Stem cells have also been isolated from orofacial tissues which include adult tooth pulp tissue, pulp tissue of deciduous teeth, periodontal ligament, apical papilla, and buccal mucosa.

HSCs can be divided into a long-term subset, capable of indefinite self-renewal, and a short-term subset that self-renew for a defined interval. HSCs give rise to nonself-renewing oligolineage progenitors, which in turn give rise to progeny that are more restricted in their differentiation potential, and finally to functionally mature cells including myeloid (monocytes and macrophages, neutrophils, basophils, eosinophils, dendritic cells), erythroid (erythrocytes), megakaryocytic (platelets) and lymphoid lineages (T-cells, B-cells, NK-cells).

Cell Culture

The cells may be cultured, for example, for 1-14 days, under conditions that maintain viability and/or cell growth. The growth can be characterized by cell division (mitosis) or by other processes, such as differentiation, during which the cells can change into specific types that are capable of functions analogous to tissues or organs in the whole organism.

During culture, cell culture medium is provided across the top of the groove array to provide nutrients and growth factors to cells retained in one or more grooves for cell metabolism and to remove the waste products generated by the cells.

In one example, the culture medium continually flows across the groove array. This type of flow is referred to herein as "continuous flow". Continuous flow is just that—continuous. The medium is continuously pumped with no breaks, resulting in a continuous stream of nutrients and growth factors. Alternatively, the culture medium may be provided by oscillatory flow or pulsatile flow. Oscillatory flow refers to an oscillating flow with zero mean velocity. Pulsatile flow is an oscillating flow superimposed on a steady flow with a non-zero mean velocity.

When a fluid is flowing through the flow channel of the multi-layer microfluidic bioreactor disclosed herein, either of two types of flow may occur depending on the velocity and viscosity of the fluid: laminar flow or turbulent flow. In one example, the cell culture medium perfused across the groove array in a laminar flow. Laminar flow tends to occur at lower velocities, below a threshold at which it becomes turbulent. Turbulent flow is an unsteady flow regime that is characterized by eddies or small packets of fluid particles, which result in lateral mixing. In non-scientific terms, laminar flow is smooth, while turbulent flow is rough. Typically, the flow in devices useful in methods of the invention is laminar because of the low Reynolds number (typically less than 10).

The device can be configured with cell culture medium inlet and outlet ports. Media can be perfused across the grooves from the inlet port(s) by syringe pumps, peristaltic pumps, hydraulic pressure, or on-chip micropumps. Media perfusion provides controlled supply of growth factors and proteins as well as regulated exposure of fluid-induced forces to cells.

There are two perfusion modes: single-pass perfusion and recirculating perfusion. In single-pass perfusion, cell culture medium is perfused across the groove array to flow waste container(s) connected to an outlet port(s), during which the perfused growth factors, cell metabolites, and secreted factors are exposed to cells for short periods of time. While in recirculating perfusion, medium, cell metabolites and secreted factors are recirculated across the groove array and exposed to cells for longer periods of time.

As used herein "culture medium" refers to a medium designed to support the growth of cells. Cell culture media generally comprise an appropriate source of energy and compounds which regulate the cell cycle (often referred to as base or basal medium). A typical culture medium is composed of a complement of amino acids, vitamins, inorganic salts, glucose, and optionally, growth factors, hormones, and/or attachment factors. Cultures can be supplemented one or more times with critical nutrients (e.g., glucose). In some embodiments, the culture medium is supplemented with, for example, growth factors, transduction enhancers to, for example, modify the cells. In some embodiments, there are two flows of culture medium, one which typically contains base media components and the other which typically contains growth media components comprising high value nutrients/supplements. In addition to nutrients, the medium also helps maintain pH and osmolality. In some embodiments, the skilled person will appreciate that the cells to be cultured will determine the culture medium and conditions for cell culture. Selection of suitable cell culture medium and culture conditions (aerobic, anaerobic, temperature, pH) is within the routine skill of the skilled person.

$O_2$ can be supplied to the culture by sparging, membrane diffusion and medium perfusion. In the latter method, the medium may be perfused through an oxygenation chamber before it enters the culture system, ensuring constant supplementation of $O_2$. Typically, a continuous replenishment of oxygen is required to avoid hypoxic conditions adjacent to the culture. This is of particular concern in high cell-density culture.

In one example, the substrate comprising the array of grooves is gas permeable and the device comprises one or more gas flow paths beneath the gas-permeable substrate that are in fluid communication with a gas. The inclusion of one or more gas flow paths, for example, immediately beneath the gas-permeable substrate that the cells are already cultured on (in one or more grooves) may provide better gas exchange between the cells and the desired atmosphere. It also eliminates the need for a gas-liquid interface.

In one example, the bioreactor is placed in a purpose built $CO_2$ incubator. Usually for mammalian cell culture, the level of $CO_2$ in the incubator defines the level of oxygen. Controlling temperature and levels of $CO_2$ and humidity in the incubator is important to the health and growth of cultured cells. For the majority of mammalian cell lines and primary cells, the optimal growth temperature is 37° C. A humidified atmosphere of approximately 95% avoids desiccation of the cultures. $CO_2$ is typically needed as part of the medium buffer system to regulate the pH. The most commonly used $CO_2$– bicarbonate buffering system depends on a chamber atmosphere of 5-10% $CO_2$, providing a pH of 7.2 to 7.4.

In another example, the device is configured with inlet and outlet ports connected to a gas supply. A continuous flow of $O_2$ may be advantageous over traditional monolayer culture systems, in which gas exchange occurs only through the medium.

In microfluidic cell culture systems, air bubbles may form during system priming, cell suspension loading and medium perfusion processes due to gas-permeability of the substrate and dissolution of gas at pressures below their solubility. Bubbles may be detrimental for microscale cell culture leading to blockage of microchannels or shear damage to cells.

In one example, a pressure difference is applied across the gas permeable substrate that drives gas to permeate from the flow channel into the gas channel.

Cell Transfection/Transduction

The present disclosure also provides methods of introducing exogenous molecules into cells. As used herein, "exogenous" molecule refers to a molecule that is not normally present in the cell, but may be introduced into the cell. Being "normally present in the cell" is determined by a certain developmental stage of the cell and environmental conditions. For instance, a molecule that is present only during embryonic development of a tissue/organ is an exogenous molecule with respect to an adult cell of said tissue/organ. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule, or an endogenous molecule expressed in a different cellular compartment or at levels higher than endogenous levels.

An exogenous molecule may be a small molecule generated by chemical synthesis, or a macromolecule such as a protein, nucleic acid, carbohydrates, lipids, glycoproteins, lipoproteins, polysaccharides, any modified derivatives thereof, or any complex comprising one or more of the above molecules.

The deliberate delivery or introduction of nucleic acids into eukaryotic cells is typically referred to as "transfection". Transfection may also refer to other methods and cell types, although other terms are often preferred. Transformation is typically used to describe non-viral DNA transfer in bacteria and non-animal eukaryotic cells, including plant cells. Genetic material (such as supercoiled plasmid DNA or siRNA constructs), or even proteins such as antibodies, may be "transfected". As used herein, "transfection" relates generally to non-viral delivery of a molecule into a cell including bacterial and non-animal eukaryotic cells.

Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

The present invention includes use of vectors for manipulation or transfer of genetic constructs. A vector is a nucleic acid molecule, preferably a DNA molecule, that can be used to artificially carry foreign genetic material; into another cell, where it can be replicated or expressed. A vector containing foreign DNA is referred to as a "recombinant vector". Examples of vectors include, but are not limited to, plasmids, viral vectors, cosmids, extrachromosomal elements, minichromosomes.

The vector is generally a DNA sequence that consists of an insert (transgene) and a larger sequence that serves as the "backbone" of the vector. The purpose of a vector which transfers genetic information to another cell is typically to isolate, multiply, or express the insert in the target cell. Vectors designed specifically for the expression of a transgene in a target cell are called "expression vectors", and generally have a promoter sequence that drives expression of the transgene. Selection of appropriate vectors is within the knowledge of those having skill in the art.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, for example, in response to a developmental and/or external stimulus, or in a tissue-specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter. A promoter can be operably linked to numerous nucleic acids, for example, through an internal ribosome entry site.

As used herein, "virus," refers to any of a large group of infectious entities that cannot grow or replicate without a host cell. Viruses typically contain a protein coat surrounding an RNA or DNA core of genetic material, but no semipermeable membrane, and are capable of growth and multiplication only in living cells. Viruses include those that are formed when, such as when a vector containing all or a part of a viral genome, is transduced into an appropriate cell or cell line for the generation of such particles. The resulting viral particles have a variety of uses, including, but not limited to, transferring nucleic acids into cells. Thus, a virus is a packaged viral genome. A virus can refer to a single particle, a stock of particles or a viral genome.

As used herein, viral vector refers to a nucleic acid vector construct that includes at least one element of viral origin and can be packaged into a viral vector particle or virus. Reference to viral vector herein is used interchangeably with virus when it is packaged inside a protein coat. The viral vector particles or virus can be used for the purpose of transferring DNA, RNA or other nucleic acids into cells. Viral vectors include, but are not limited to, retroviral vectors, vaccinia vectors, lentiviral vectors, herpes virus vectors (e.g., HSV), baculoviral vectors, cytomegalovirus (CMV) vectors, papillomavirus vectors, simian virus (SV40) vectors, Sindbis vectors, Semliki Forest virus vectors, phage vectors, adenoviral vectors, and adeno-associated viral (AAV) vectors. Viral vectors typically include engineered viruses that are operatively linked to exogenous genes to transfer (as vehicles or shuttles) the exogenous genes into cells.

When a viral vector or viral particle is used to transfer genetic material of interest into a cell, the technique is referred to as "transduction". Thus generally, to "transduce" a cell is to use a viral vector or viral particle to transfer genetic material into a cell.

As used herein, nucleic acid molecule includes deoxyribonucleic acid (DNA) and ribonucleic acid (RNA), can be single- or double-stranded; can be linear, branched or circular; and can be of any length. Nucleic acids include those capable of forming duplexes, as well as triplex-forming nucleic acids. Nucleic acids also include analogs or derivatives of DNA or RNA. Analogs may comprise one or more of an altered backbone (e.g., phosphate-sugar backbone analogs), pentose sugar(s) or nucleobase(s) (e.g., universal bases, xeno nucleic acids). Examples include peptide nucleic acid (PNA), morpholino oligomers, locked nucleic acid (LNA), as well as glycol nucleic acid (GNA) and threose nucleic acid (TNA). Nucleic acids can encode gene products, such as, for example, polypeptides, regulatory RNAs (e.g., microRNAs, small interfering RNAs (siRNAs), guide RNAs (gRNA), and antisense), ribozymes, and small hairpins.

The exogenous molecule (e.g., vector) may be introduced into the device, simultaneously with or subsequent to introduction of the cells by cross flow and/or longitudinal flow. The exogenous molecule (e.g., vector) may be introduced into the device subsequent to cell expansion by culture methods described herein. The exogenous molecule can be supplied in a medium that promotes transfection/transduction, for example, assist, promote, or facilitate entry into the cell, including liposome formulations, lipofectin or a culture medium that supports viral transduction. In some methods, the cells are activated prior to addition of a viral vector, for example, T cells may be activated by stimulation of the TCR activation pathway via CD3- and CD28-specific antibodies in combination with cytokines such as IL-7 and IL-15.

The methods may include static (e.g., single loading) or flow transfection/transduction, or a combination thereof. Flow transduction methods may include but are not limited to continuous perfusion where the exogenous molecule (e.g., vector) is continuously perfused through the device for the entire transfection/transduction duration, or recirculating perfusion where the viral vectors may be recirculated through the device, for example, using a peristaltic pump. In another example, consecutive perfusion is used where the exogenous molecule is loaded and allowed to incubate under static conditions. After a shortened transfection/transduction period, a fresh stock of the exogenous molecule can be loaded into the device to add more exogenous molecules and replenish the cells culture medium nutrients/growth factors.

Following transfection/transduction, the cells may be expanded by culture methods described herein. Expansion of transfected/transduced cells may be accomplished by drug selection when an appropriate drug-resistance marker is included in the transfected/transduced DNA. In such embodiments, a selective medium containing the drug is used to expand the transfected/transduced cells.

Cell Selection

The present disclosure also provides methods of selecting cells using capture or binding reagents immobilised on the grooves. Antibodies may be used as capture reagents. Antibodies can be used to positively or negatively select cells as they flow along the grooves based on the expression of certain surface antigens, or the lack of expression of lineage-specific antigens, respectively. For example, the methods can be used to select or enrich CD34+ hematopoietic stem/progenitors by positive selection using an anti-CD34 antibody. In another example, the methods can be used to select or enrich T cells using anti-T-cell antibodies (e.g., CD2, CD3, CD4/CD8, T-cell receptor $\alpha/\beta$). The captured cells can be released from the antibody using for example, the proteolytic enzyme chymopapain, or neuraminidase. The cells may be subsequently expanded by culture methods disclosed herein and/or transduced/transfected by methods disclosed herein.

The antibodies can be polyclonal or monoclonal antibodies. Preferably, the antibody preparation is affinity-purified. Particularly useful antibodies remain reactive after being adsorbed to a solid surface, and further, retain structural integrity when completely dried, and are reactive when rehydrated.

Antibodies can be immobilized to the groove array using routine methods known to those skilled in the art. An "immobilized" binding partner refers to a binding partner that is adsorbed, embedded or affixed, either permanently or semi-permanently, to the grooves.

In some embodiments, the methods comprise immobilising the antibody on the grooves prior to introducing the cells into the device. For example, the antibody may be provided to the groves by cross flow and/or longitudinal flow and left to incubate to adsorb thereto under static or flow conditions. In some embodiments, the reactive groups on the surface of the grooves are blocked following capture reagent immobilisation. Any coating that prevents non-specific adsorption of biomolecules can be used. These coatings are generally polymers that bind water e.g., polyethylene glycol (PEG) or PEG copolymers such as Pluronic 127. Other polymers that can be used include carbohydrate polymers (dextran), or zwitterion antifouling polymers.

As used herein, the term "specifically binds" refers to a specific capture reagents preferential interaction with a given ligand over other ligands on the cell or components present in the sample. For example, a specific binding agent that specifically binds a given ligand, binds the given ligand, under suitable conditions, in an amount or a degree that is observable over that of any nonspecific interaction with other components in the sample. Suitable conditions are those that allow interaction between a given specific binding agent and a given ligand. These conditions include pH, temperature, concentration, solvent, time of incubation, and the like, and may differ among given specific binding agent and ligand pairs, but may be readily determined by those skilled in the art.

The term "antibody", as used herein, refers to intact immunoglobulin molecules as well as fragments of immunoglobulin molecules that are capable of binding to an epitope of an antigen.

Antibodies can be of any class (e.g., IgG, IgE, IgM, IgD, IgA, and IgY), or subclass (e.g., IgG1, IgG2, IgG3, IgG4, IgA1 and IgA2). The classes are distinguished by the type of heavy chain they contain. IgG molecules comprise heavy chains known as γ-chains; IgMs have μ-chains; IgAs have α-chains; IgEs have ε-chains; and IgDs have δ-chains.

Antibodies can be formed by the association of one heavy chain type (e.g., μ, δ, γ, α, or ε) with one light chain type (e.g., λ or κ). The basic (monomer) unit of a conventional antibody is a four polypeptide unit consisting of two identical heavy chains and two identical light chains connected together by disulfide bonds. and light chains (HC and LC) also contain intramolecular disulfide bonds for stabilization. The light chains are shorter, with lower molecular weights than the heavy chains. The general shape of an antibody is a Y, with a flexible hinge (interdomain) region at the centre of the Y. Each polypeptide chain has a constant region and a variable region.

The common notation for the light chain variable region is VL and for the light chain constant region is CL. The notation is similar for the heavy chain variable (VH) and constant regions (CH) with CH1, CH2, and CH3 denoting the different constant region domains of the heavy chain. The fragment crystallizable (Fc) region contains only constant regions from the heavy chains (CH), but the fragment antigen-binding region (Fab) includes both a constant domain and the variable domains of both the heavy and light chains (VH and CL). The fragment variable region FV region contains only the two variable domains.

As used herein, "variable region" refers to the portions of the light and/or heavy chains of an antibody that specifically binds to an antigen and, for example, includes amino acid sequences of CDRs; i.e., CDR1, CDR2, and CDR3, and framework regions (FRs). For example, the variable region comprises three or four FRs (e.g., FR1, FR2, FR3 and optionally FR4) together with three CDRs. VH refers to the variable region of the heavy chain. VL refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region typically has three CDR regions identified as CDR1, CDR2 and CDR3. In one example, the amino acid positions assigned to CDRs and FRs are defined according to Kabat Sequences of Proteins of Immunological Interest, National Institutes of Health, Bethesda, Md., 1987 and 1991 (also referred to herein as "the Kabat numbering system". According to the numbering system of Kabat, VH FRs and CDRs are positioned as follows: residues 1-30 (FR1), 31-35 (CDR1), 36-49 (FR2), 50-65 (CDR2), 66-94 (FR3), 95-102 (CDR3) and 103-113 (FR4). According to the numbering system of Kabat, VL FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4).

"Framework regions" (FR) are those variable domain residues other than the CDR residues.

The term "intact antibody" as used herein refers to whole or full-length antibodies that comprise heavy and light chains including a Fc region. The constant domains may be wild-type sequence constant domains (e.g., human wild-type sequence constant domains) or amino acid sequence variants thereof.

Antibodies can differ in valency. Some immunoglobulins can form multimers through linkage of their Fc domains via a J chain.

Antibodies can be polyclonal, monoclonal, recombinant.

The term "polyclonal antibody" as used herein refers to a mixed population of antibodies directed against different determinants (epitopes). The modifier "polyclonal" indicates the character of the antibody population and is not to be construed as requiring production of the antibody by any particular method. For example, polyclonal antibodies to be used in accordance with the present invention may be made introducing the whole pathogen or an isolated antigen by inoculation or infection into a host (e.g., goat) to induce the host to make antibodies against the pathogen or antigen.

The term "monoclonal antibody" (mAb) as used herein refers to an antibody obtained from a population of substantially homogeneous antibodies, or to said population of antibodies. The individual antibodies comprising the population are essentially identical, except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by the hybridoma method first described by Kohler et al., Nature (1975) 256:495, or may be made by recombinant DNA methods. The "monoclonal antibodies" may also be isolated from phage antibody libraries using the techniques described in Clackson et al., Nature (1991) 352:624-628 and Marks et al., J. Mol. Biol. (1991) 222:581-597, for example, or by other methods known in the art.

An "antigen binding fragment" of an antibody comprises one or more variable regions of an intact antibody. Fragments of immunoglobulin molecules such as F(ab')2, Fab, Fab' and Fv can be selectively cleaved from an immunoglobulin molecule using reducing agents and proteases to digest or cleave certain portions of the immunoglobulin protein structure. Fragments of immunoglobulin molecules can also be made recombinantly.

These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows.

A Fab fragment consists of a monovalent antigen-binding fragment of an antibody molecule and can be produced by digestion of a whole antibody molecule with the enzyme papain, to yield a fragment consisting of an intact light chain and a portion of a heavy chain.

A Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

A (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

A Fv fragment is defined as a genetically engineered fragment containing the variable region of a light chain and the variable region of a heavy chain expressed as two chains.

As used herein "recombinant antibody" refers to antibodies that are prepared, expressed, created or isolated by recombinant means, such as (a) antibodies isolated from an animal (e.g., mouse) that is transgenic for immunoglobulin genes (e.g., human immunoglobulin genes) or hybridoma prepared therefrom; (b) antibodies isolated from a host cell transformed to express the antibody; (c) antibodies isolated from a recombinant antibody library; and (d) antibodies prepared, expressed, created or isolated by any other means that involve splicing of immunoglobulin gene sequences to other DNA sequences.

Recombinant antibodies can be produced in any format. The smallest antigen binding fragment that retains its complete antigen binding site is the Fv fragment, which consists entirely of variable (V) regions. A soluble and flexible amino acid peptide linker is used to connect the V regions to a scFv (single chain fragment variable) fragment for stabilization of the molecule, or the constant (C) domains are added to the V regions to generate a Fab fragment (fragment, antigen-binding). scFv and Fab are widely used fragments that can be easily produced in prokaryotic hosts. Other antibody formats include disulfide-bond stabilized scFv (ds-scFv), single chain Fab (scFab), as well as di- and multimeric antibody formats like dia-, tria- and tetra-bodies, or minibodies (miniAbs) that comprise different formats consisting of scFvs linked to oligomerization domains. The smallest fragments are $V_{HH}/V_H$ of camelid heavy chain antibodies and single domain antibodies (sdAb).

The term "antibody" as used herein also encompasses humanized antibodies, primatized antibodies, human antibodies, synhumanized antibodies and chimeric antibodies.

Following selection, the cells may be expanded by culture methods described herein. Expansion of transfected/transduced cells may be accomplished by drug selection when an appropriate drug-resistance marker is included in the transfected/transduced DNA. In such embodiments, a selective medium containing the drug is used to expand the transfected/transduced cells.

Cell Harvesting

The methods of the disclosure may comprise a harvesting step that comprises providing a cross flow and/or longitudinal flow of extraction medium to displace the cells from the grooves into the flow stream and out of the device for collection and use.

While cross flow of extraction medium may have utility particularly in laboratory applications where a continual supply of cells is required, longitudinal flow extraction is more efficient and is therefore preferable in larger scale cell culture systems.

Numerical simulation was used to guide the design of microfluidic bioreactors 100 according to embodiments of the disclosure. COMSOL Multiphysics, commonly used in computation fluid dynamics, mass transfer, and chemical reactions, was used to model a) cell transport and deposition into microgrooves; b) uptake of glucose and oxygen and c) transport of lentiviral vector into cells.

Example 1: Simulation of Flow, Oxygen and Glucose Concentration for High Density Growth COMSOL Multiphysics was used to simulate fluid dynamics and mass transfer to test whether cells have adequate nutrition for high density cell growth given device geometry, properties of the semipermeable membrane, and flow rates. The flow layer was manufacture from polydimethylsiloxane (PDMS) which is permeable to oxygen. The parameters for the simulation of oxygen and glucose mass transfer are shown in Table 1.

TABLE 1

| Symbol | Parameter | Description |
|---|---|---|
| rho | 1000 [kg/m^3] | Fluid density |
| eta | 1e-3 [Pa * s] | Fluid viscosity |
| v0 | 0.005 [cm/s] | Inlet velocity |
| Dglu | 1e-9 [m^2/s] | Glucose diffusion coefficient in water |
| Doxy | 4e-9 [m^2/s] | Oxygen diffusion coefficient in water |
| Coxy | 0.25 [mol/m^3] | Oxygen concentration at boundary |
| Cglu | 10 [mol/m^3] | Glucose concentration at inlet |
| Vfrac | 0.8 | Cell volume fraction |
| etacell | 10 * eta | Packed cell viscosity |
| rhocell | 1.06 * rho | Packed cell density |

TABLE 1-continued

| Symbol | Parameter | Description |
|---|---|---|
| tPDMS | 0.1 [mm] | PDMS thickness |
| PC | 6.7 | Partition coeffient for oxygen (Cwater/CPDMS |
| DoxyPDMS | 3.4e−9 [m^2/s] | Diffusion coefficient of oxygen in PDMS |
| Soxy_water | 0.96 [mM/atm] | Solubility of oxygen in water |
| Soxy_PDMS | PC * Soxy_water | Solubility of oxygen in PDMS |
| PO2 | 0.2 [atm] | Partial pressure of oxygen |
| Groove_Pitch | 50e−6 [m] | Groove pitch |
| Groove_Width | 150e−6 [m] | Groove width |
| Groove_Height | 200e−6 [m] | Groove height |
| Plate_Separation | 100e−6 [m] | Plate separation |
| Cell_Concentration | 1e9 [1/ml] | Cell concentration |
| Specific_Glu_U | 0.73e−17 [mol/s] | Glucose specific uptake per cell |
| Specific_O2_U | 2.6e−17 [mol/s] | Oxygen specific uptake per cell |

Figure 13:
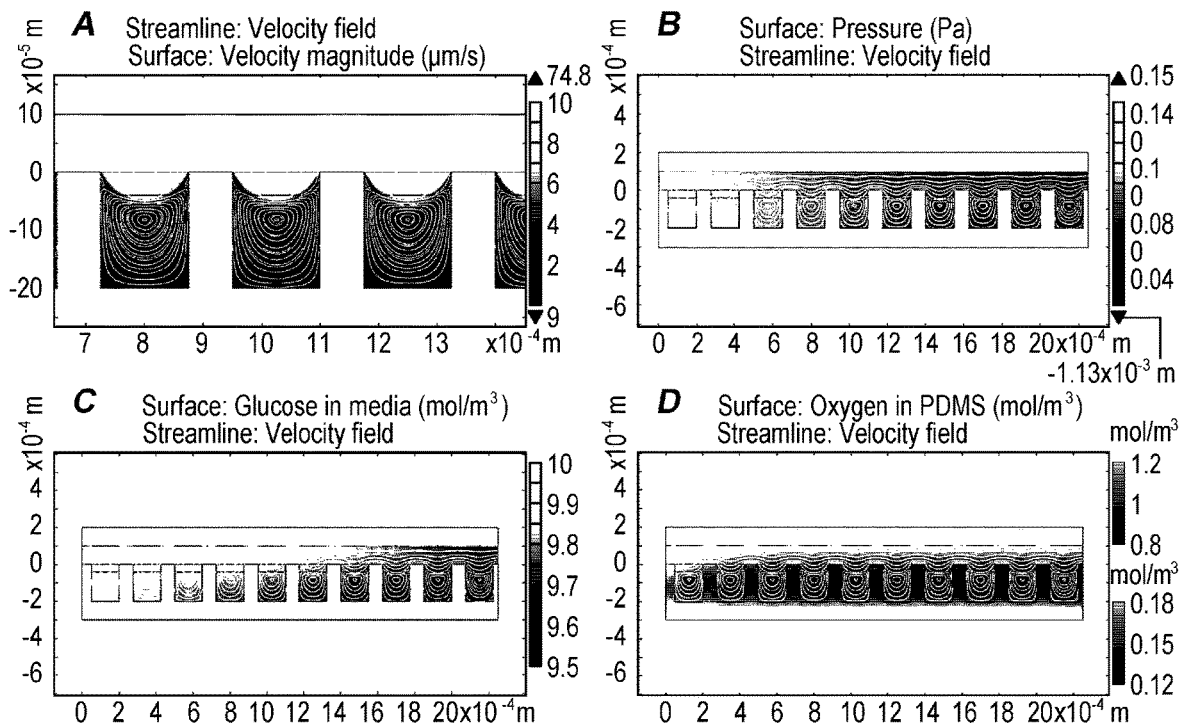
FIG. 13 is a simulation output modelling flow, oxygen and glucose according to one example.

Oxygen and glucose concentration were simulated to establish that cells could be grown at tissue density ($10^8$-$10^9$ cells/ml) inside microgrooves. The 2D simulation geometry shown in FIG. 13 is a cross-section through a PDMS multi-layer bioreactor where there is cross flow over a grooved substrate. The simulation assumes that oxygen is at 0.2 bar on the underside of the gas permeable grooved membrane and top of the device. The plate separation was 100 μm. The groove depth, width and pitch were 200 μm, 150 μm and 200 μm respectively. The cell concentration in the base of grooves was $10^9$ cells/ml, and it was assumed that cells filled the bottom 80% of each groove. The inlet media flow velocity was 0.05 mm/s from left to right (streamlines shown as white lines) (FIG. 13A).

Flow separation occurred at the boundary between the packed cell mass and media as shown by the streamlines demonstrating laminar flow across the grooves. Very little media penetrated the biomass. The hydrostatic pressure decreased linearly along the channel, as was expected.

The concentration of glucose and oxygen is shown in FIGS. 13C and 13D. The specific uptake of glucose and oxygen by the biomass in the lower 80% volume of each groove was based on cell line measurements (glucose specific uptake=0.73e−17 [molls/cell], oxygen specific uptake=2.6e−17[mol/s/cell]). The glucose feed concentration was 10 mM. Cells would remain viable as long as glucose concentration remained above 4 mM. Glucose was depleted downstream across the flow channel (0.15 mM/mm). There was also a glucose gradient within each groove. The glucose concentration was depleted by about 0.2 mM at the base of each groove.

Oxygen (20% volume fraction in air) was supplied to cells from the upper and low boundary of the parallel plate groove boundary (FIG. 13D). Oxygen is the most scarce metabolite because of its relatively low solubility in water (0.25 mM at 37 C). The simulation showed that oxygen transport to cells was enhanced by using an oxygen permeable material such as PDMS for the flow layer which has an oxygen solubility 6.7× higher than water. A stable oxygen concentration profile was established downstream by the 3-4th groove. It was lowest in the middle of the biomass (0.11 mM). Bone marrow cells typically grow at 5% atm (around 5 mM) therefore it is unlikely that low oxygen would limit cell growth in this model.

This simulation demonstrates that the device can supply the oxygen and glucose requirements of the cells grown at $10^8$-$10^9$ cells/ml which is around 1000 times higher than standard flask or bag culture.

Figure 17A:
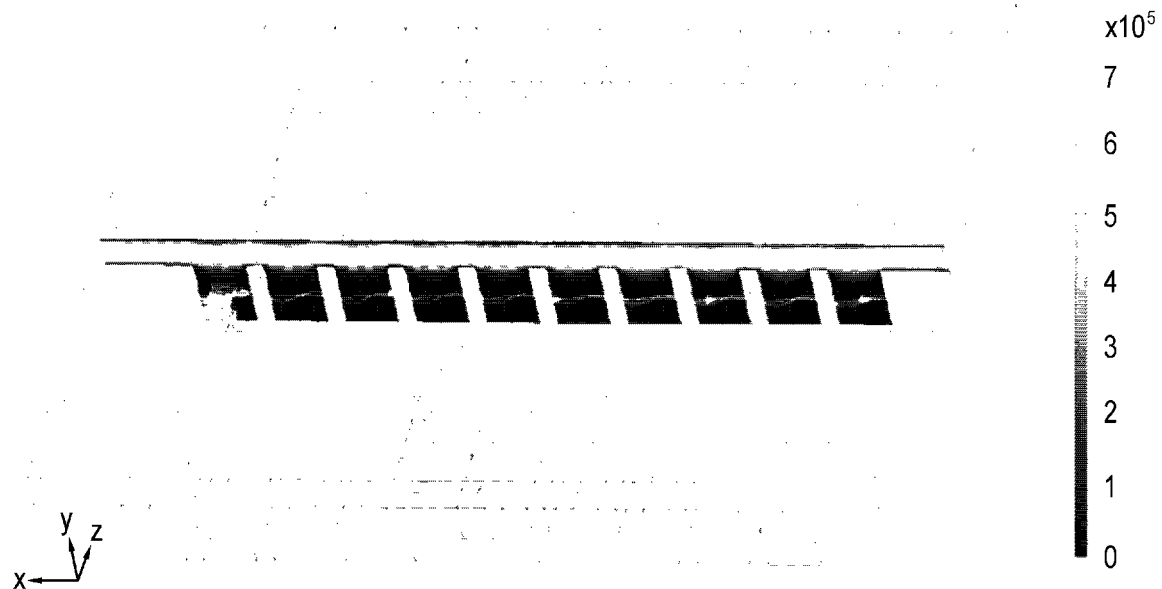
FIG. 17 shows three-dimensional flow simulated when flow enters from the left inlet and travels over groves (FIG. 17A) or when flow enters from the upper inlet and travels along grooves (FIG. 17B).
Figure 17B:
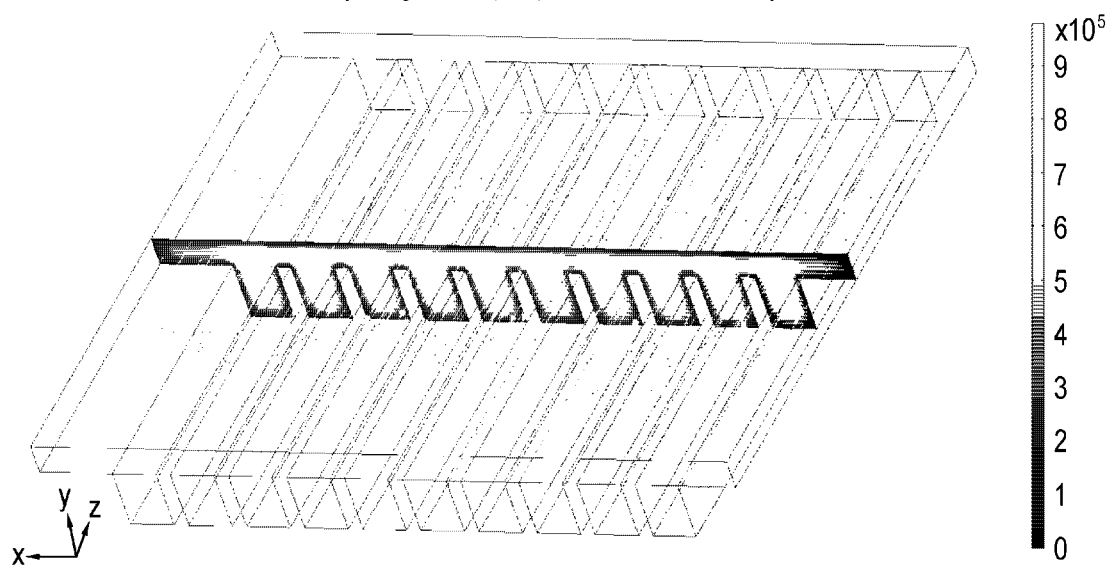

FIG. 17 shows three-dimensional flow simulated when flow enters from the left inlet and travels over groves (FIG. 17a) or when flow enters from the upper inlet and travels along grooves (FIG. 17b). When the flow is across grooves (FIG. 17a) particles will be trapped by eddy flow because they follow streamlines with a circular path orthogonal to the longitudinal dimension of grooves. When flow is directed in the same direction as grooves, particles inside grooves will follow streamlines that are parallel with the walls of the groove (FIG. 17b) exiting via the lower outlet. FIG. 17 also shows that for the same inlet fluid velocity, flow entering from the upper inlet generates higher fluid velocities inside the grooves compared to flow entering from the left inlet. The wall shear stress at the base of grooves was also estimated using this simulation method. It is shown below that cells were selectively capture by antibody at an average upper inlet flow velocity of 22 mm/min. This flow generated 0.0218 Pa wall shear stress at the base of grooves.

Example 2: Simulation of Cell Deposition into Grooves

Figure 14:
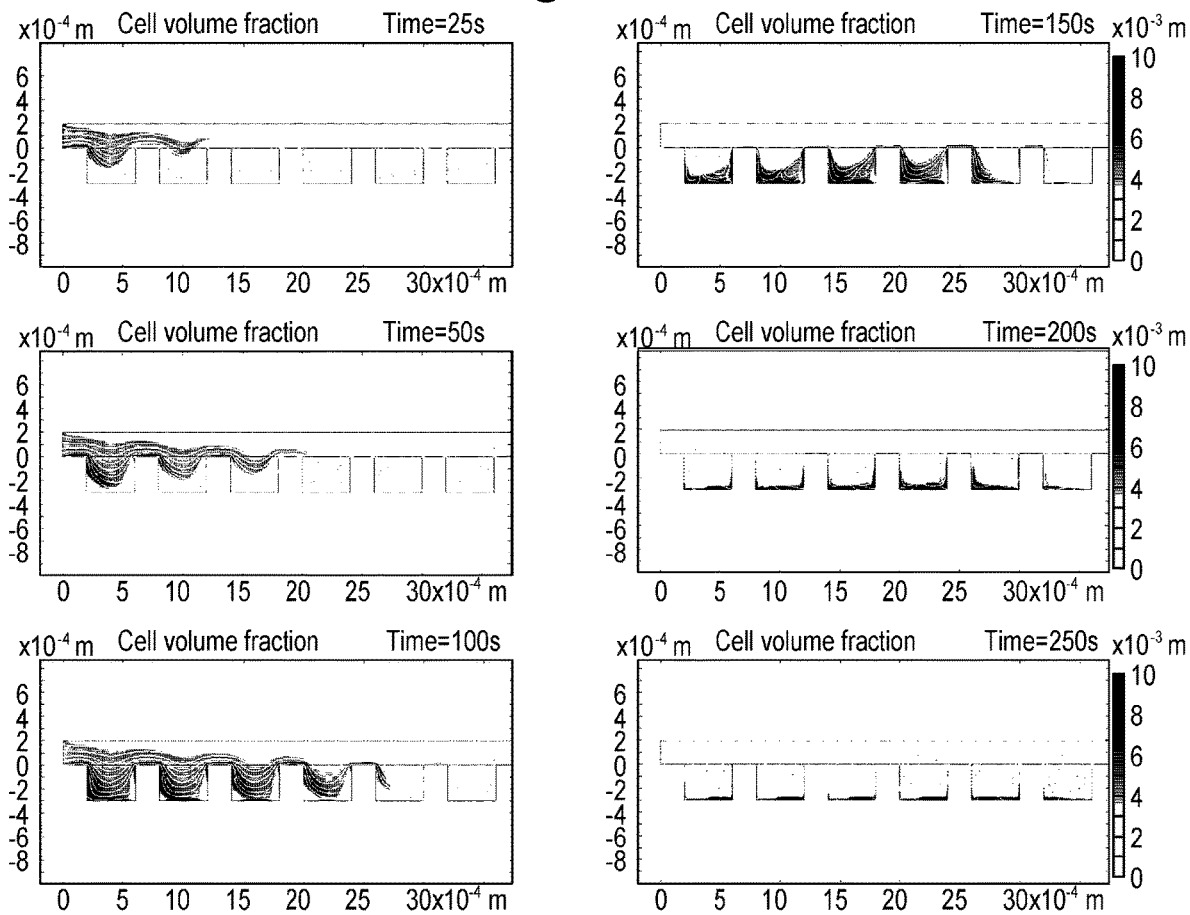
FIG. 14 is a simulation output modelling cell deposition into grooves over 24 to 250 seconds) according to one example.

Cells have a specific gravity of 1.05-1.1, and sediment in culture media. Sedimentation of cells into grooves was modelled using a laminar flow mixture model with an inlet fluid velocity of 4.8 μm/min and a cell sedimentation velocity of 4.2 μm/s. FIG. 14 shows that most of the cells deposited in the first 5 grooves in a short time (around 200 seconds) using sedimentation because the sedimentation distance is only 200 microns. Once cells deposit in the groove substrate they are held there during the culture process, allowing exchange of media without cells flowing out of the device. The typical perfusion rate of culture media to maintain cells at high viability is around 1 ml/million cells/day. The simulation parameters for cell deposition into grooved substrate are shown below in Table 2.

TABLE 2

| Symbol | Parameter | Description |
|---|---|---|
| rho_s | 1060 [kg/m^3] | Density of solid particles |
| rho_f | 1000 [kg/m^3] | Density of pure fluid |
| eta_f | 1e−3 [Pa * s] | Viscosity of pure fluid |
| phi_max | CC_max * CV | Maximum packing |
| phi0 | CC*CV | Average concentration |
| R | 5e−6 [m] | Particle radius |
| u_st | (2/9)*(−g_const) * R^2 * (rho_s−rho_f)/eta_f | Settling velocity |
| H | 200e−6 [m] | Channel Height |
| W | 6 [mm] | Channel Length |
| Vi | 0.05 [mm/s] | Inlet velocity |
| D1 | 0.41 * R^2 | Model parameter D_phi |
| D2 | 0.62* R^2 | Model parameter D_mu |
| Dg | 300e−6 [m] | Groove depth |

TABLE 2-continued

| Symbol | Parameter | Description |
|---|---|---|
| Wg | 400e-6 [m] | Groove width |
| T1 | 100 [s] | Cell input pulse width |
| CC | 1e7 [1/ml] | Inlet cell concentration |
| CV | 4 * pi * R^3/3 | Cell volume |
| CC_max | (2 * R)^(-3) | Max cell concentration |
| CW | 8 [mm] | Channel width |
| N_cells | FR * CC * T1 | Number of cells loaded |
| FR | CW * H * Vi | Flow rate |

Simulation also showed that in the geometry used by the model, it was not possible to recover cells from grooves by flow directed across channels (cross flow) because of flow separation at the entry to grooves (FIG. 17A).

Figure 15:
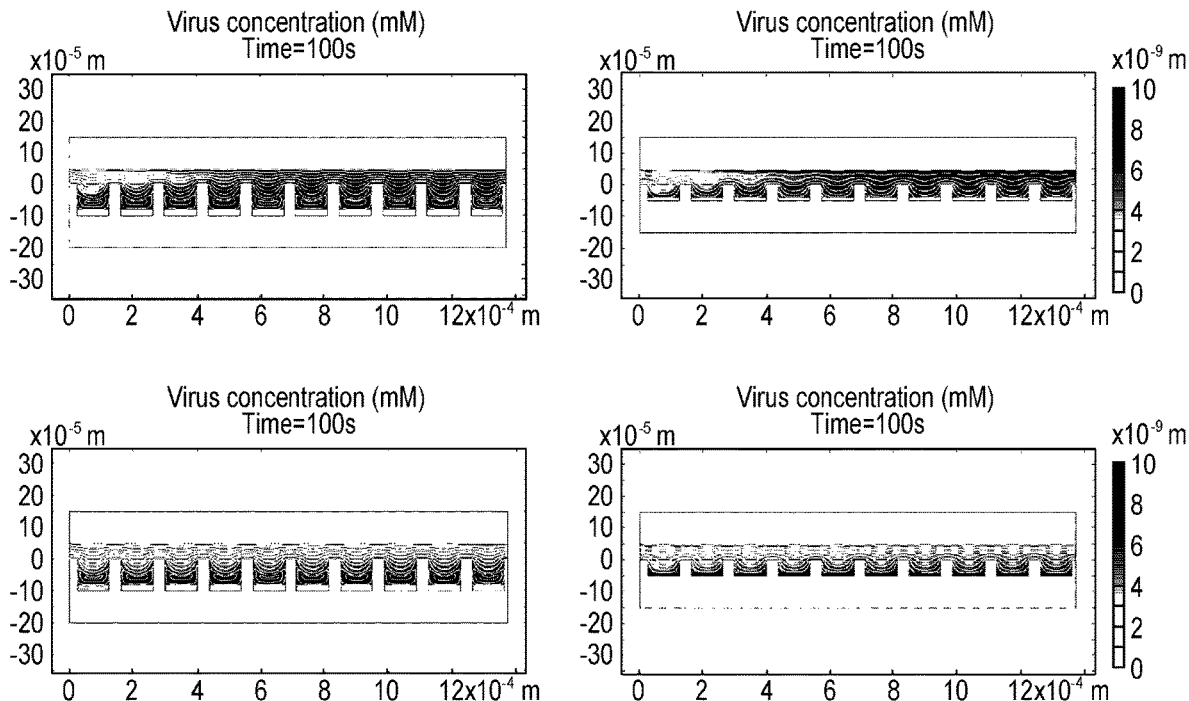
FIG. 15 is a simulation output modelling transport of lentivirus according to one example.

Example 3: Simulation of Microfluidic Transport of Virus Uptake by Cells Deposited in the Grooved Substrate Another problem sought to be addressed that is addressed by the present disclosure is the slow rate of transport of gene vectors to the surface of cells. The rate of diffusion of viral vectors is around $2 \times 10^{-8}$ cm$^2$/sec. Diffusion times scale with the square of the distance, so it would take a virus particle 140 hr to diffuse 1 mm, but only 30 minutes to diffuse 50 microns. Current methods to increase transport of virus into cells utilise centrifugation (Spinoculation) which is difficult to automate at clinical scale. However, in microfluidic systems diffusion distances are dramatically reduced. COMSOL Multiphysics was used to simulate the rate of transport of Lentivirus into a cell monolayer at the bottom of grooves (FIG. 15). The simulation parameters for simulation of virus transport into cells on a grooved substrate are shown in Table 3. Transport of virus into cells was enhanced using shallow 50 μm deep grooves in comparison to 100 μm deep grooves because flow separation occurred when the groove depth was 100 μm (FIG. 15 left graphs) which impeded transport of virus into the monolayer. The eddy at the base of the microgroove introduced a diffusion barrier, because its flow is approximately 10-fold lower than the flow rate in the main flow channel. This simulation demonstrates the need to select groove depths that are optimal for transfer of virus into cells.

Example 4: Fabrication of PDMS (Silicon Rubber) Microgroove Bioreactors

Standard photolithography was used to manufacture negative moulds. Flow layer designs were printed on high resolution (2400 dpi, 50 μm features) A4 positive lithographic film (Rose Graphics) or quartz photographic masks (1 μm features, Bandwidth Foundry, Sydney University) with designs contact printed onto negative photoresist (KMPR 1050, MMRC Pty Ltd) spin-coated onto silicon wafers. A mask aligner was used to align and expose photomasks with UV light.

The negative silicon wafer mould was replicated by soft embossing to create a secondary ZEONOR® 1060R thermoplastic (Zeon Asia Pty Ltd, Singapore) negative mould which had greater durability compared to the silicon master, and could be reused to make multiple devices with identical geometry. A PDMS (SYLGARD™ 184, The Dow Chemical Company) mould of the silicon master was used for hot embossing the ZEONOR® 1060R thermoplastic mould.

In the laboratory prototype, the three-layered PDMS device was aligned with a 3D printed tool with alignment posts and bonded together with air plasma in cleanrooms. This was then bonded to a glass plate for structural support, ease of handling and autoclavability.

Example 5: Design

A generic design corresponding to FIG. 1 has separate ports for cell inoculation and harvesting, as well as a port to supply media. The media port is connected to a flow resister to reduce flow rate, because media flow rates are much lower than flow rates required for cell inoculation and harvesting. Dimensions for a small scale design (4×106 cells) are shown in Table 4.

TABLE 4

| Dimension | Value |
|---|---|
| Flow layer channel height | 50 μm |
| Flow layer thickness | 3 mm |
| Groove layer depth | 75 μm |
| Groove layer thickness | 0.6 mm |
| Gas layer channel height | 50 μm |
| Gas layer thickness | 1 mm |

TABLE 3

| Symbol | Parameter | Description |
|---|---|---|
| Cvirus | (1e10/6.02e23) [mol/cm^3] | Inlet concentration of virus |
| Dvirus | 2e-8 [cm^2/s] | Virus diffusion coefficient |
| EntryRatio | 10 | Entry length ratio |
| epsilon | 0.4 | Porosity |
| eta | 1e-3 [Pa * s] | Viscosity |
| etacell | 10 * eta | Packed cell viscosity |
| Groove_Height | 50e-6 [m] or 100e-6 [m] | Groove height |
| Groove_Pitch | 25e-6 [m] | Groove pitch |
| Groove_Width | 100e-6 [m] | Groove width |
| Kvirus | 1e-7 [m/s] | Mass transfer coefficient for transfer of virus across wall of cell |
| Plate_Separation | 50e-6 [m] | Plate separation |
| rho | 1000 [kg/m^3] | Density |
| rhocell | 1.06 * rho | Packed cell density |
| Specific_Virus_U | (0.01/6.02e23) [mol/s] | Specific Uptake of virus |
| tPDMS | 0.1 [mm] | PDMS thickness |
| UVirus | Cell_Concentration * Specific_Virus_U | Virus uptake |
| v0 | 0.001 [cm/s] | Inlet velocity |
| Vfrac | 0.2 | Cell volume fraction |

TABLE 4-continued

| Dimension | Value |
|---|---|
| Cell culture chamber volume | 28 µL |
| Cell capacity | 4 million cells |

Dimensions for a large-scale design which increases the growth volume by a factor of 25 ($10^8$ cells) are shown in Table 5. The device is very compact considering that one would require a 50-100 ml tissue culture flask to grow this number of cells.

TABLE 5

| Dimension | Value |
|---|---|
| Flow layer channel height | 50 µm |
| Flow layer thickness | 3 mm |
| Groove layer depth | 75 µm |
| Groove layer thickness | 0.6 mm |
| Gas layer channel height | 50 µm |
| Gas layer thickness | 1 mm |
| Cell culture chamber volume | 336 µL |
| Cell capacity | $10^8$ cells |

Figure 19A:
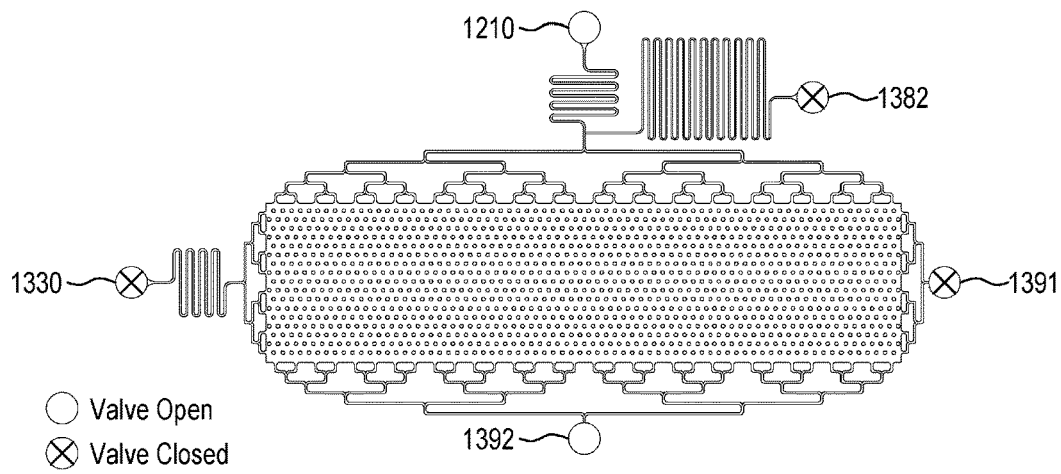
FIG. 19 is a schematic illustration of a bioreactor showing valve control for cell loading, media perfusion for expansion and cell extraction respectively, according to an embodiment.
Figure 19B:
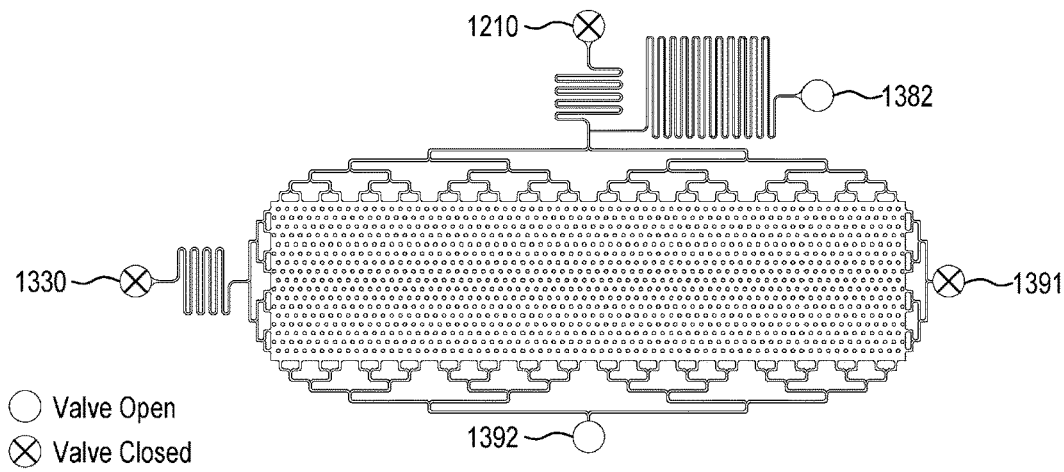
Figure 19C:
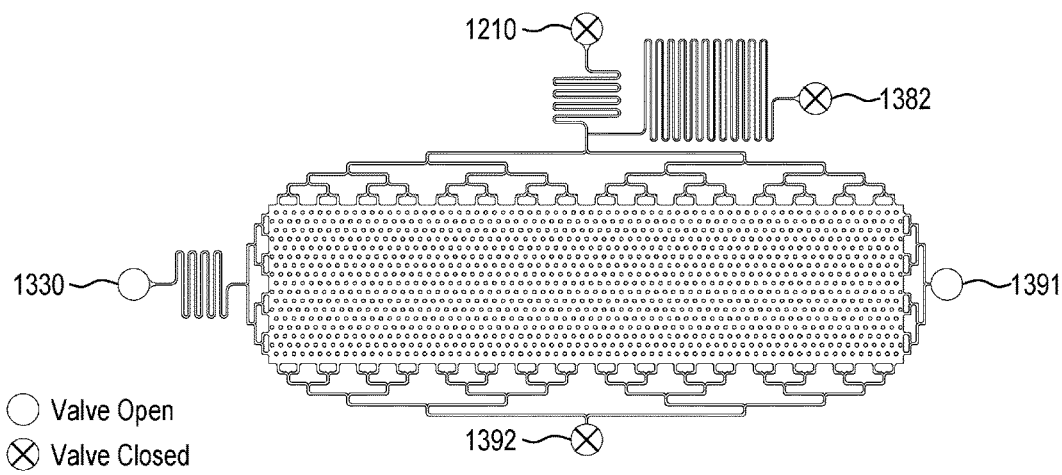

Referring to the embodiment in FIG. 19, the bioreactor provides for both cross flow and longitudinal flow, providing a number of valves and media reservoirs to achieve the states of cell loading, cell expansion and cell extraction. For cell loading (FIG. 19A) the cell inlet 1381 and the media perfusion outlet 1392 is opened but the cell extraction inlet 1330, cell extraction outlet 1391 and media perfusion inlet 1382 is closed. For cell expansion (FIG. 19B) growth media is perfused into the media reservoirs via a media perfusion inlet 1382 and media perfusion outlet 1392 being open and a cell inlet 1381, cell extraction inlet 1330 and cell extraction outlet 1391 being closed. For cell extraction (FIG. 19C), a cell extraction inlet 1330 and cell extraction outlet 1391 are opened and the cell inlet 1381, media perfusion inlet 1382 and media perfusion outlet 1392 are closed.

Figure 18:
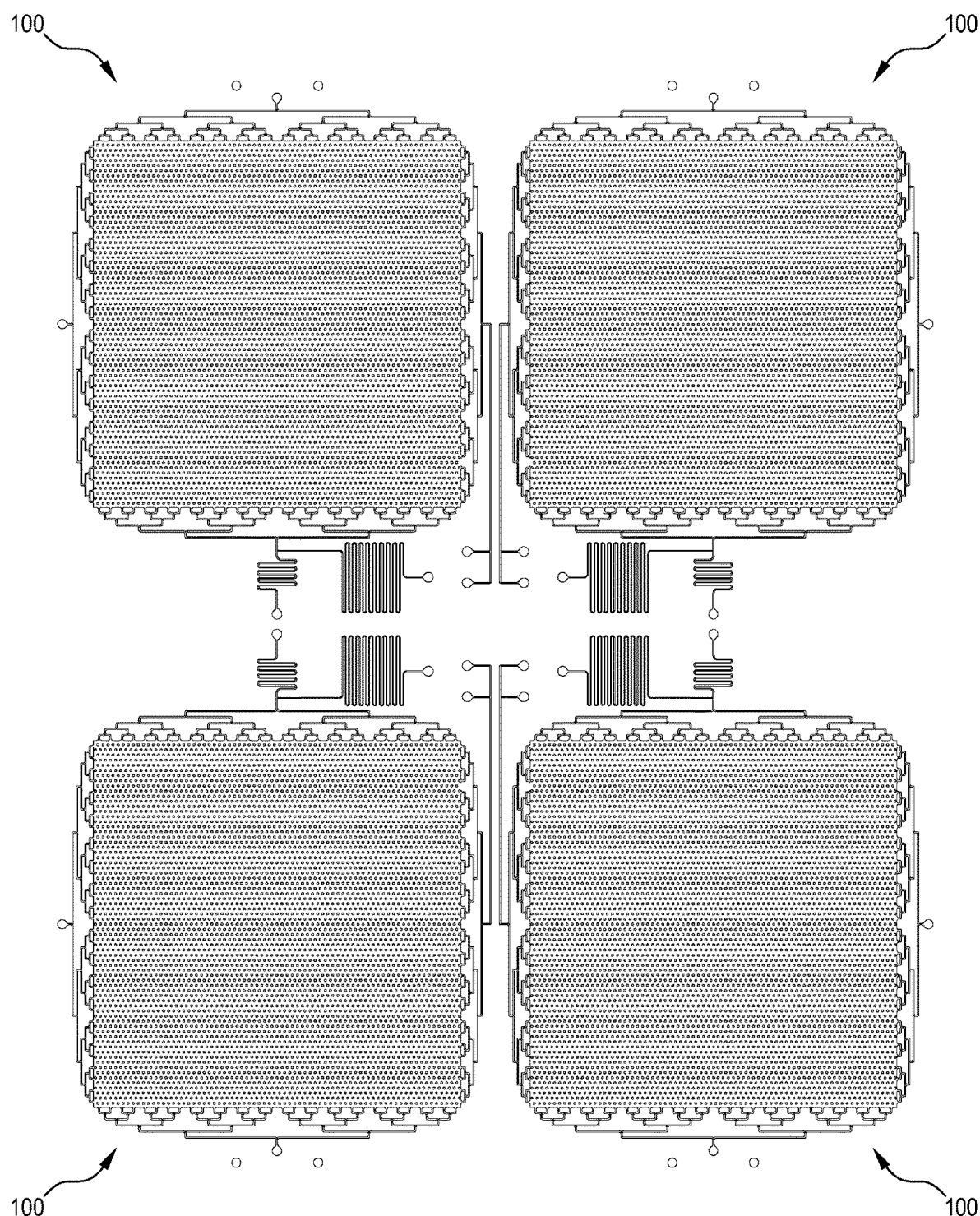
FIG. 18 is a plan view of a multilayer sheet containing a plurality of bioreactors according to an embodiment of the disclosure.

Table 6 provides parameters for another multi-layer bioreactor according to an embodiment of the disclosure in which four bioreactors are provided on a single A5 sheet, as shown in FIG. 18.

TABLE 6

| Parameter | Value |
|---|---|
| Cell density at confluence (cells/ml) | 3.50E+08 |
| Groove width (microns) | 250 |
| Groove pitch (microns) | 300 |
| Groove depth (microns) | 100 |
| Groove length (mm) | 60 |
| Flow cell length (mm) | 60 |
| Number of grooves per flow cell | 200 |
| Number of cells per flow cell | 1.05E+08 |

Table 7 provides parameters for yet another multi-layer bioreactor for use in a stack of 24 bioreactor sheets (FIG. 18) forming a disposable large scale unit that may be utilised by an automated bioreactor cell culture system according to embodiments of the disclosure.

TABLE 7

| Parameter | Value |
|---|---|
| Number of flow cells per layer | 4 |
| Number of cells per layer | $4 \times 10^8$ |

TABLE 7-continued

| Parameter | Value |
|---|---|
| Layer width (mm) | 148 |
| Layer length (mm) | 210 |
| Layer depth (mm) | 3 |
| Number of layers to grow $10^{10}$ cells | 24 |
| Height of stack (mm) | 71 |
| Area per stack (cm$^2$) | 3000 |
| Area per cell (µm) ($10^8$ CD34+ cells) | 4000 |

Example 6: Calibration of Flow Resistors

Figure 16:
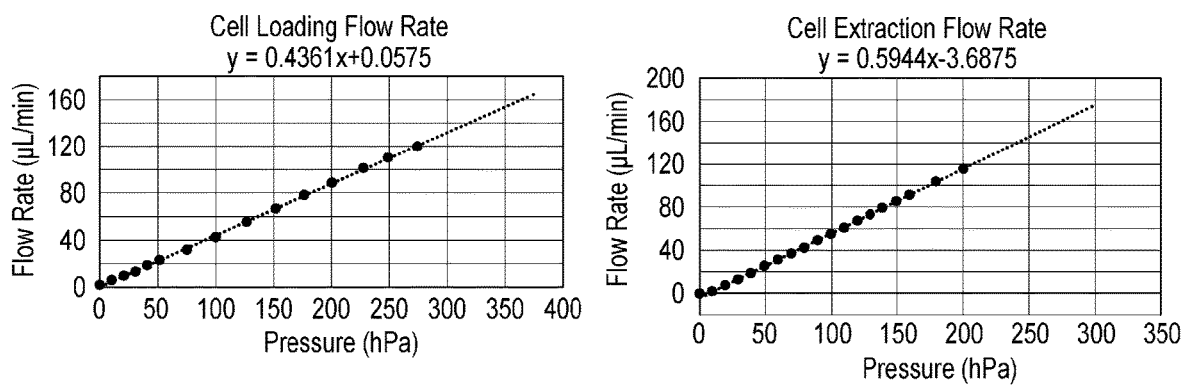
FIG. 16 shows data from calibration of flow resistors according to one example.
Figure 16:
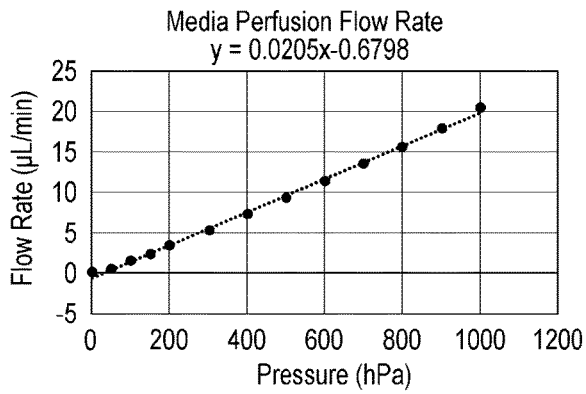

Calibrated hydraulic resistors were used to verify that flow control using flow resistors on the header 200 was accurate and reproducible for cell loading from a cell source through first inlet port 210, cell extraction fluid delivery through second inlet port 330, and culture medium delivered into first inlet port 210 from a source of culture medium as shown in FIG. 16. The pressure source and flow sensor were XenoWorks® Digital Microinjector (Sutter Instrument) and FM-ECO-Micro-1X, 1-80 µL per minute (CorSolutions, Ithica, NY), respectively. The flow rate was controlled by setting a digital pressure source. Flow paths were closed using 3 way manually operated valves, or tubing clamps.

Figure 20:
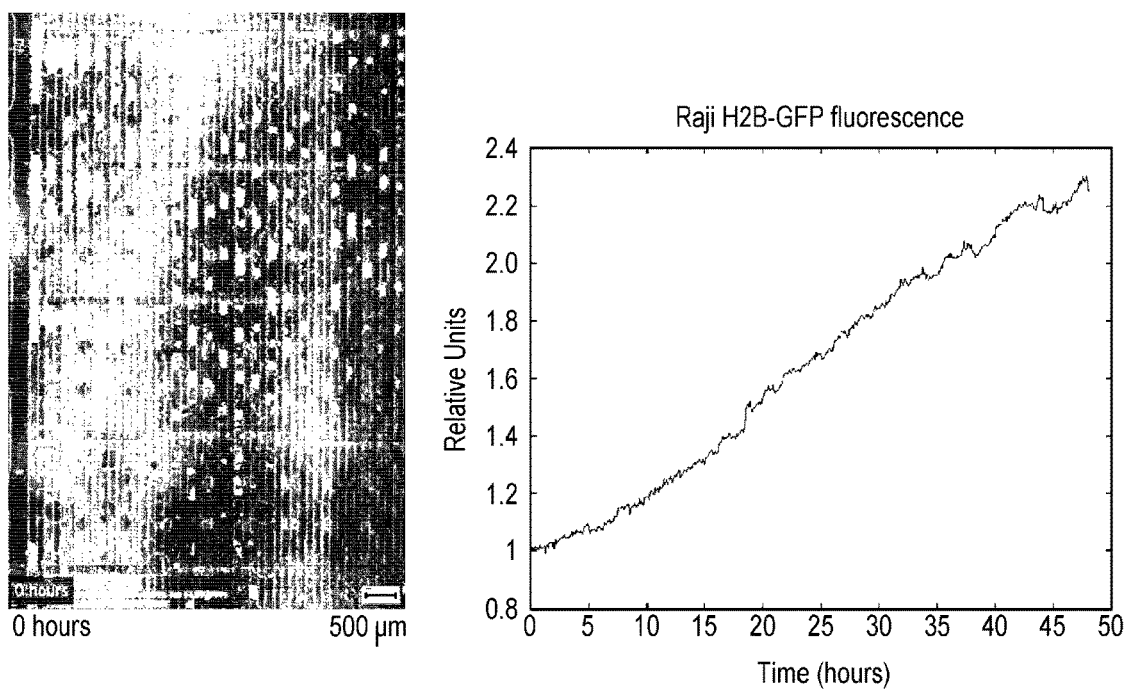
FIG. 20 shows the growth of Raji H2B-GFP cells in the grooves of a bioreactor of the present disclosure.
Figure 21:
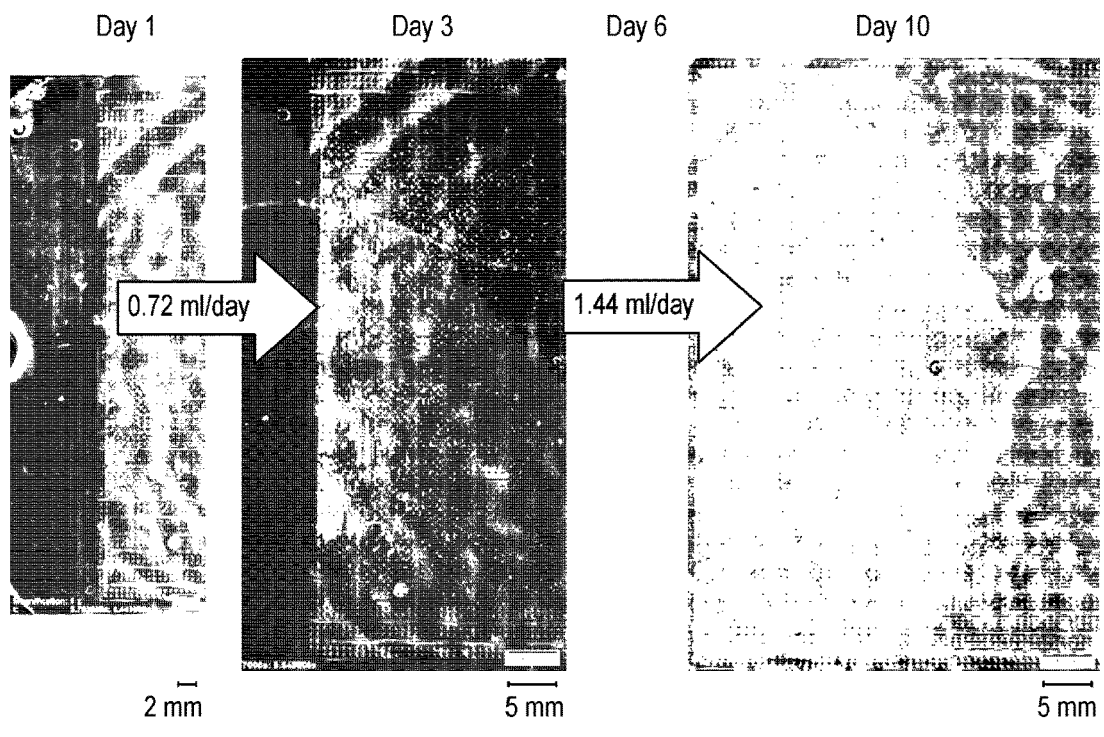
FIG. 21 shows expansion of Raji H2B-GFP with groove crossflow perfusion

Example 7: Demonstration of Cell Deposition, Expansion and Recovery Using Microgroove Bioreactors A bioreactor design (having a capacity of $10^8$ cells) was used to grow a non-adherent B cell line Raji-H2B-GFP. Approximately, $8 \times 10^6$ Raji H2B-GFP cells were loaded by cross flow deposition into the bioreactor and expanded to fill the bioreactor over a 17 day period. A similar flow regime simulated in FIG. 21 was used to deposit cells into the first 5-10 grooves (see day 1, FIG. 21. Time lapse fluorescence microscopy was used to track the rate of growth from integrated GFP fluorescence FIG. 20. As cells proliferate, they overflow into downstream grooves. This pattern of growth is illustrated in FIG. 20. Flow rate was incremented as the number of cells increased. The media perfusion flow rates were set at approximately 1 ml/million cells/day, low enough for cell retention by microgrooves, but high enough to support cell growth and proliferation.

Figure 22:
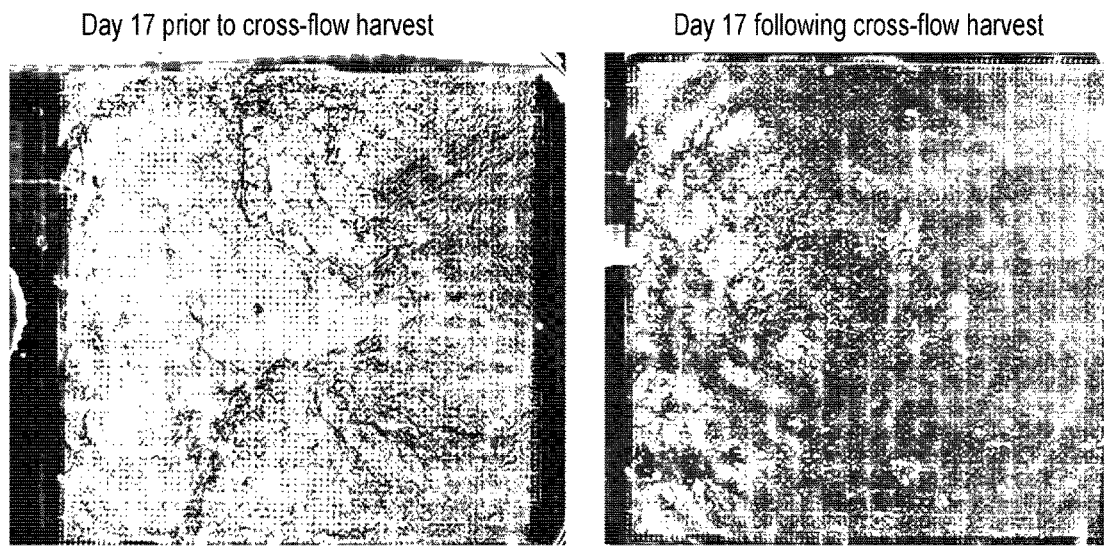
FIG. 22 shows incomplete recovery of Raji H2B GFP cells by crossflow

Cells grew to confluence at day 17, filling the entire grooved substrate, with cells passing out of the outlet of the device. It was not possible to fully harvest expanded cells at day 17 ($30.9 \times 10^6$ cells recovered at outlet with 67.5% viability, FIG. 22). The maximum flow rate was 7.2 ml/day so viability was reduced because the perfusion rate was not able to keep up with cell expansion (i.e., should have been 50-100 ml/day, see FIG. 22).

From this experiment it is estimated that the confluent cell density of the grooved substrate (groove depth 80 µm, width 150 µm, spacing 100 µm) was 1.7 million cells/cm$^2$. Cells grow inside grooves at a density of around 350 million cells/ml. Therefore a (60 mm×15 mm) device is predicted to grow up to 15 million cells.

The present inventors developed the bidirectional groove bioreactor to increase cell recovery and viability. Cells could be loaded by deposition into grooves using cross flow or longitudinal flow. The present inventors also reduced the length of the culture area by a factor of 4 so that the microfluidic culture perfusion flow rates could keep up with the number of cells supported by the device.

Figure 23:
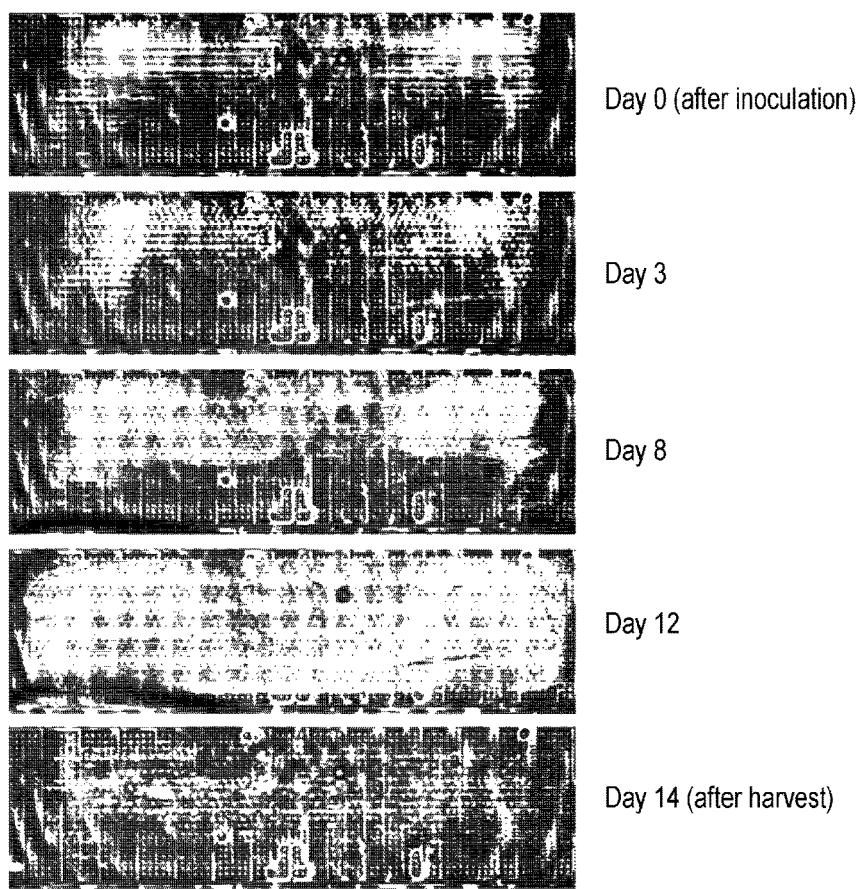
FIG. 23 shows expansion of TF1a-H2B-GFP in a bioreactor according to an embodiment of the present disclosure. Fluorescent images of TF1a-H2B-GFP cells show expansion over 14 days.

Jurkat, Raji, Nalm6, TF1a cell lines were grown in the bidirectional flow device (FIG. 23). Approximately $1 \times 10^6$ cells were loaded in 200 μL (5 million cells/mL) using cross flow. The loading efficiency was around 80%. Cells were harvested at day 14 by longitudinal flow ($12.2 \times 10^6$ with 87% viability, see FIG. 23). A summary of the expansion protocol is shown in Table 8.

inlet from a cell wash reservoir fluidly connected to the bioreactor via a hydraulic line together with input of cell wash from a cell wash reservoir via a hydraulic line connected to a flow recorder and opening of a spent cell wash outlet reservoir.

Gene transfer is achieved via input of vector into the bioreactor from a vector reservoir via a hydraulic line with vector flow via a pneumatic line and pressure source connected to the vector reservoir; in addition, a vector flow hydraulic line is opened to allow excess vector flow through from the bioreactor.

Cell culture expansion is achieved via supply of fresh culture media to the culturing cells in the bioreactor via

TABLE 8

Cell expansion protocol

| Process | Duration (minutes) | Cell Inlet | Media Perfusion Inlet | Cell Extraction Inlet | Media Perfusion Outlet | Cell Extraction Outlet | Description |
|---|---|---|---|---|---|---|---|
| Device priming with cell culture media | 30 | ○ | 0.9 μL/min | 25.3 μL/min | ○ | ○ | Pre-filled device and tubing with cell culture media (specific to the cell line) to ensure all surfaces are wetted |
| Device degassing | 60 | X | X | 200 hPa | X | X | Pressurised the gas permeable device to remove trapped air bubbles by diffusion |
| Cell loading | 20 | 19.5 μL/min | X | X | ○ | X | Loaded 200 μL of cells at a concentration of 5 million per mL (total of 1 million cells) via the cell loading port |
| Culture media perfusion | 5-14 days | X | 0.07 μL/min (1 mL/day), increasing by 0.035 μL/min every day from the 3rd day | X | ○ | X | Flowed cell culture media at a rate equivalent to 1 mL per million cells per day to recover and expand the loaded cells |
| Cell extraction | 15 | X | X | 114.9 μL/min | X | ○ | Extracted the cells for processing |

Valve state
○ Open
X Closed

Example 8: Microfluidic Integration of Cell Selection, Gene Transfer and Cell Expansion Using Permeable Groove Bioreactors A groove microbioreactor may be used to perform a) selection of target cells using monoclonal antibody bound to grooves b) gene transduction of captured target cells and (c) culture expansion of transduced cells within a single cartridge containing a large number of microfluidic devices connected in parallel. The sequence of these process is can be automated by pneumatic control of valves and pressures sources as follows:

Cell inoculation is achieved via cell input from an external cell storage reservoir via a hydraulic line connected to the bioreactor wherein cell transfer is achieved with pneumatic pressure from a pneumatic line connected to the external cell reservoir via a pressure source along with an open cell waste outlet to receive spent cell solution.

Target cell enrichment is achieved via the open cell input from the external cell reservoir and opening of a cell wash hydraulic supply lines to the top and bottom of the bioreactor together with input of air and carbon dioxide and output of waste growth media via a media waste line and reservoir connected to a biomass sensor to monitor flow of loose cells with a cell output line for cell harvest.

Cell harvest is achieved input of cell wash to the bioreactor from an external source via a flow reader and output of harvested cells via the cell output line.

Example 9: Viral Transduction of Jurkat Cells

This experiment describes the transduction of Jurkat cells using a lentiviral vector for delivery of Green Fluorescent Protein (GFP) as a marker into cells. Jurkat cells were transduced with hrSIN lentiviral vectors expressing GFP. The vector produced from the Phoenix ECO packaging cell line was used for viral transduction following the protocol shown in Table 9.

TABLE 9

| Process | Duration (minutes) | Cell Inlet | Media Perfusion Inlet | Cell Extraction Inlet | Media Perfusion Outlet | Cell Extraction Outlet | Description |
|---|---|---|---|---|---|---|---|
| Device priming with cell culture media | 30 | ○ | 0.9 µL/min | 25.3 µL/min | ○ | ○ | Pre-filled device and tubing with cell culture media (specific to the cell line) to ensure all surfaces are wetted |
| Device degassing | 60 | X | X | 200 hPa | X | X | Pressurised the gas permeable device to remove trapped air bubbles by diffusion |
| Cell loading | 20 | 19.5 µL/min | X | X | ○ | X | Loaded 200 µL of cells at a concentration of 5 million per mL (total of 1 million cells) via the cell loading port |
| Viral culture media loading | 120 | X | 5 µL/min | X | ○ | X | Replaced the cell culture media contained in the device with media containing viral vectors |
| Viral culture media perfusion | 24 hours | X | 0.07 µL/min | X | ○ | X | Reduced the flow rate of viral culture media to allow for infection of the loaded cells |
| Culture media perfusion | 4 days | X | 0.07 µL/min (1 mL/day), increasing by 0.035 µL/min every day from the 3rd day | X | ○ | X | Replaced the viral culture media with cell culture media to recover and expand the transduced cells |
| Cell extraction | 15 | X | X | 114.9 µL/min | X | ○ | Extracted the cells for processing |

Figure 24:
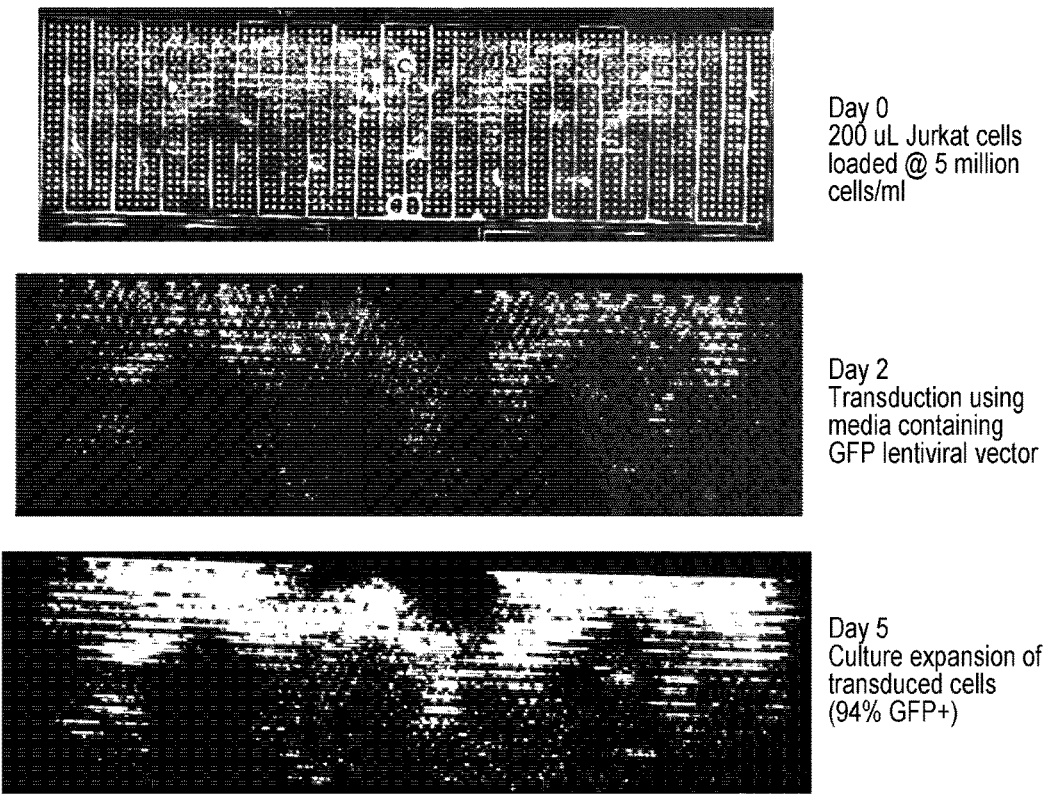
FIG. 24 shows the use of a bioreactor of the present disclosure for transduction of Jurkat cells with GFP and subsequent expansion.
Figure 25:
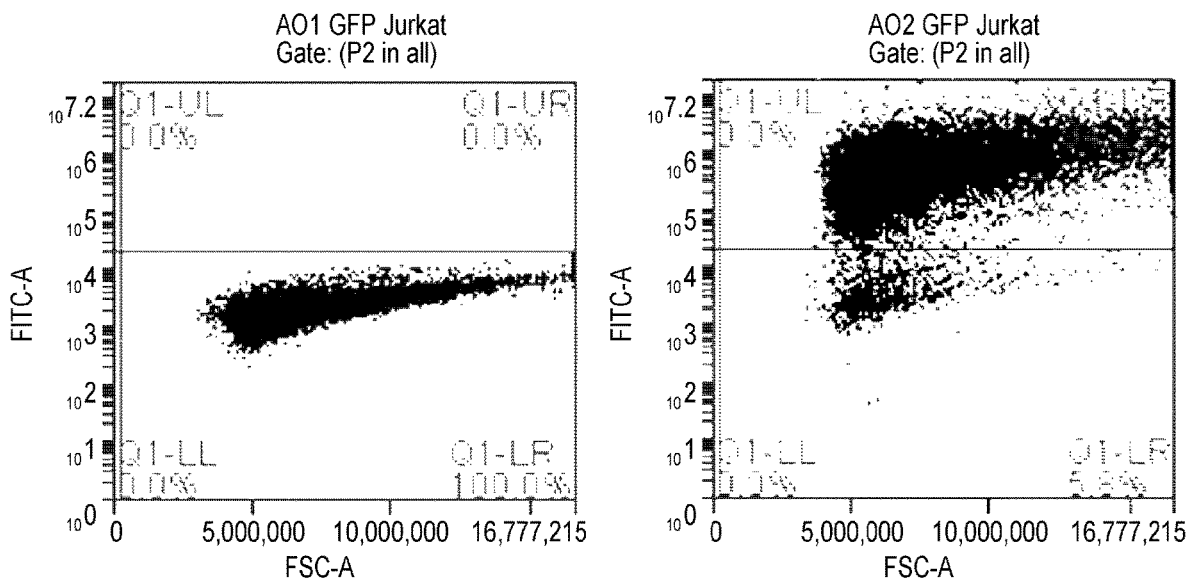
FIG. 25 shows flow cytometry showing the expression of GFP in Jurkat cells; control (left), following transduction and expansion (right).

Viral culture media (VCM) was flushed into the system to replace the cell culture medium with flow rate reduced for continued transduction over the next 24 hours. Transduced cells were then expanded over the following days by perfusion culture. Following expansion cells were harvested and analysed by flow cytometry. FIG. 24 shows widefield photomicrographs of the bidirectional flow bioreactor at inoculation, day 2 following transduction and day 5 following 3 days of transduction. At harvest 94% of Jurkat cells expressed GFP (FIG. 25, Table 10). Retronectin, an agent used to enhance transduction efficiency, can be introduced into the device prior to transduction by, for example, by flow along the grooves.

Figure 26:
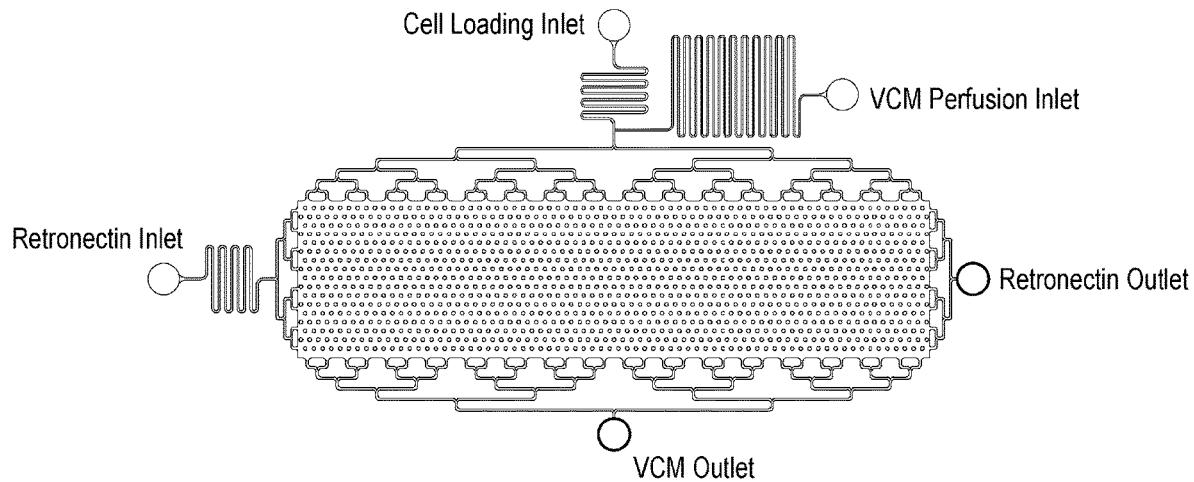
FIG. 26 shows the bioreactor as shown in FIG. 19 including valves and media reservoirs for viral transduction of Jurkat cells.

FIG. 26 shows the bioreactor device used in this experiment. The cell loading inlet and virus-containing medium (VCM) inlet directs the flow of cells and VCM perpendicular to the orientation of the microgrooves. Flow passes out of the device at the VCM outlet. Retronectin, an agent used to enhance transduction efficiency, can be introduced into the device prior to transduction by, for example, by flow parallel to the orientation of microgrooves using the retronectin inlet and outlet ports. However, retronectin was not required for efficient transduction. The retronectin inlet and outlet ports were also used for cell harvesting by flow parallel to the orientation of microgrooves.

TABLE 10

Transduction performance

| Day 0 input | Day 5 Harvested | Day 5 Transduction efficiency (GFP+) | Day 5 viability |
|---|---|---|---|
| 1 million | 2.25 million | 95.4% | 82.1% |

Figure 27:
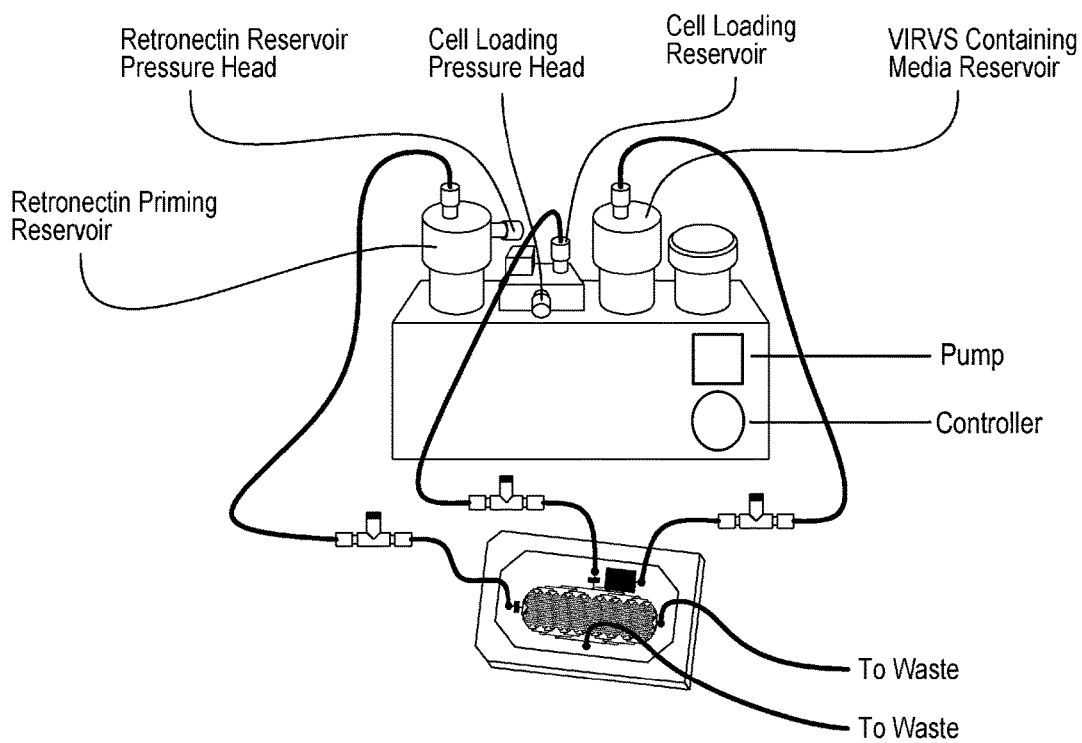
FIG. 27 shows the microfluidic circuit used with the bioreactor as shown in FIG. 26.

FIG. 27 shows how the microfluidic bioreactor device was connected to pressurising sealed vessels for loading retronectin, cells and VCM. A XenoWorks® Digital Microinjector was used to control the flow rate by regulating the pressure head inside each vessel. The following method steps were used to perform viral transduction:

1. Approximately 1 million cells were loaded into the microfluidic device; 200 µL of cell suspension (@ $5 \times 10^6$ Jurkat cells/ml) was loaded into the device without fibronectin using a pressure head of +125 hPa over 20 minutes.
2. 1 ml of thawed VCM (lentivirus delivering GFP) was then injected into the microfluidic device at +500 hPa over 1 hour.
3. The microfluidic device and reservoirs were then moved into a tissue culture incubator overnight. VCM flow rate was reduced overnight using a pressure head of +40 hPa.
4. Microfluidic device was imaged the next day using fluorescence microscopy to quantify the expression of GFP inside cells.

This experiment demonstrates lentiviral transduction of Jurkat cells in a closed system without the use of centrifugation and retronectin to concentrate virus.

Example 10: Cell Separation

Physically adsorbed monoclonal antibody was used to capture target cells as they roll along the groove base with flow directed in the same direction as grooves (longitudinal flow). Pluronic F127 was used to reduce non-specific adsorption of antigen negative cells. A mixture of fluorescent cell lines at a ratio of 1:1 was used to assess the performance of cell separation.

Figure 28:
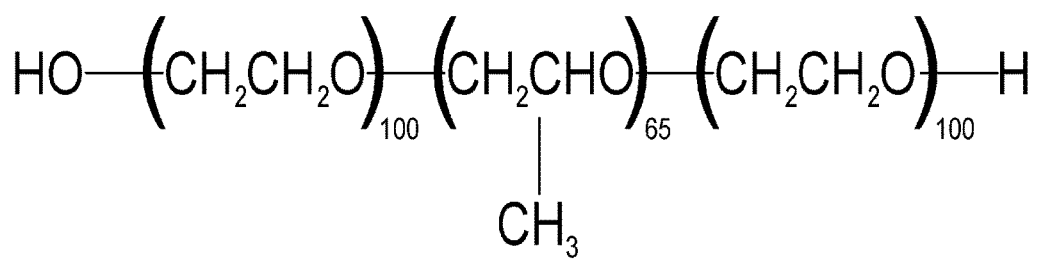
FIG. 28 shows the structure of Pluronic F127 surfactant.

Pluronic F127 is a surfactant that reduces non-specific protein binding and has been particularly effective for microfluidic protein assays. It is a polyethylene glycol macromolecule modified with —$CH_3$ groups that bind strongly to hydrophobic PDMS (FIG. 28). The present inventors assessed the effect of Pluronic F127 on non-specific binding of antigen negative cells. The cell mixture was Jurkat-H2B mCherry (CD3 positive, CD34 negative) and TF1a-H2B-GFP (CD3 negative, CD34 positive) at a 1:1 ratio (50000 cells per ml).

CD3 cells were selected by physically adsorbing antiCD3 moAb (4D3, 50 μg/ml) inside microfluidic bioreactors by overnight adsorption at 4° C. The capture of cells was observed by continuous flow of a 1:1 ratio of CD3+:CD3− cell mixture along grooves for 2 hours. To determine cell viability following cell capture, cells were cultured in situ by cross flow perfusion culture. A more detailed protocol is described in Table 11.

Figure 30:
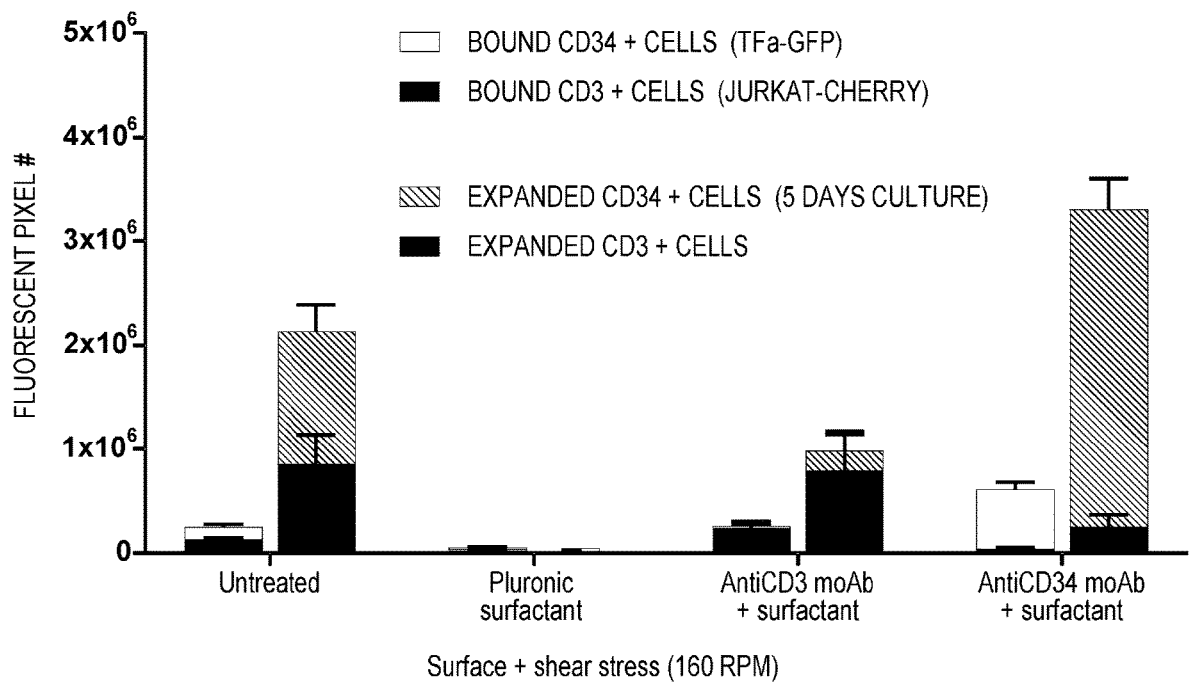
FIG. 30 shows specific capture of CD3+ or CD34+ cells.

Hydrophobic polystyrene tissue culture dishes were physically adsorbed with monoclonal antibody (moAb) binding CD3 or CD34 antigens, followed by treatment with the surfactant Pluronic F127. A 1:1 mix of CD34+(TF1a-GFP) and CD3+(Jurkat Cherry) were incubated on dishes on an orbital shaker @ 160 RMP for 30 minutes before harvesting of unbound cells. FIG. 30 shows that antiCD3 MoAb or antiCD34 MoAb enriched bound CD3+(black bars) or

TABLE 11

Cell separation

| Process | Duration (minutes) | Cell Inlet | Media Perfusion Inlet | Cell Extraction Inlet | Media Perfusion Outlet | Cell Extraction Outlet | Description |
|---|---|---|---|---|---|---|---|
| Device priming with cell culture media | 30 | ○ | 0.9 μL/min | 25.3 μL/min | ○ | ○ | Pre-filled device and tubing with cell culture media (specific to the cell line) to ensure all surfaces are wetted |
| Device degassing | 60 | X | X | 200 hPa | X | X | Pressurised the gas permeable device to remove trapped air bubbles by diffusion |
| Antibody loading | 30 | 35.2 μL/min | X | X | ○ | X | Replaced the cell culture media contained in the device with antibody |
| Antibody physisorption @ 4° C. | Overnight | 50 hPa | X | X | X | X | Coated the microfluidic chamber with antibody overnight to create a cell-specific binding surface |
| Pluronic F-127 loading | 60 | 31.6 μL/min | X | X | X | ○ | Replaced the antibody contained in the device with an anti-fouling solution (1% Pluronic F-127) |
| Pluronic F-127 coating | 60 | 50 hPa | X | X | X | X | Coated the microfluidic chamber with 1% Pluronic F-127 to eliminate non-specific cell binding |
| Continuous cell loading and separation | 120 | X | X | 31.6 μL/min | X | ○ | Loaded the cells parallel to the grooves to capture the positive cells (specific to the adsorbed antibody) and remove the negative cells |
| Culture media perfusion | 5-14 days | X | 0.07 μL/min (1 mL/day), increasing by 0.035 μL/min every day from the 3rd day | X | ○ | X | Flowed cell culture media at a rate equivalent to 1 mL per million cells per day to recover and expand the loaded cells |
| Cell extraction | 15 | X | X | 114.9 μL/min | X | ○ | Extracted the cells for processing |

Figure 29:
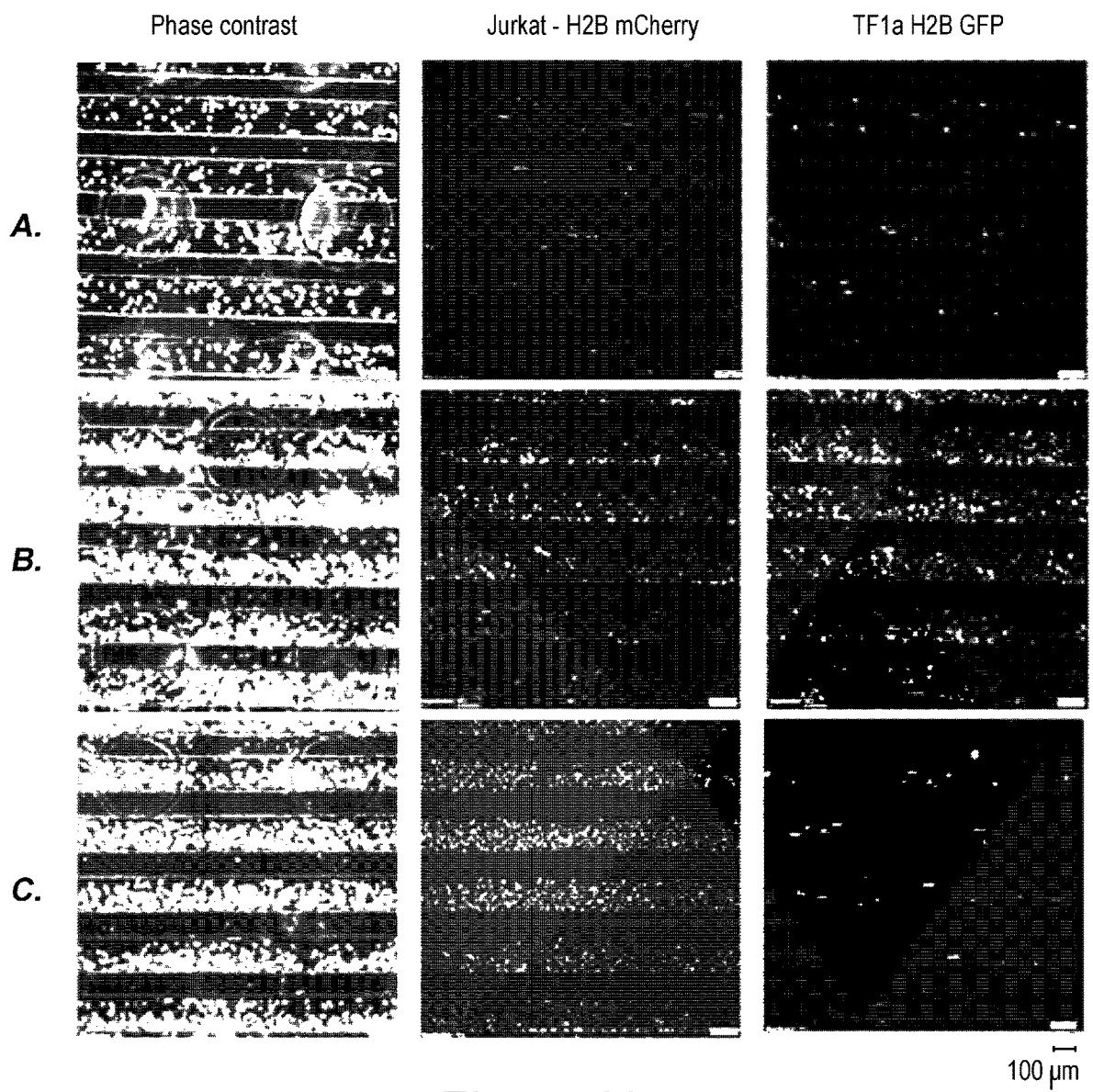
FIG. 29 shows the effect of substrate chemistry on selective binding of CD3+ cells in grooves during longitudinal flow.

Devices that were coated with Pluronic 127 prior to antiCD3 moAb adsorption did not bind Jurkat-H2B-mCherry (CD3+) nor TF1a H2B GFP (CD3-) (FIG. 29A). There was stronger binding of CD3+ cells (Jurkat-H2B-mCherry) using a module that had been coated with antiCD3 moAb alone (FIG. 29B). The selectivity of adsorbed antiCD3 moAb was enhanced by blocking non-specific cell binding with Pluronic following antibody binding (FIG. 29C). We have also shown that bound cells detach over 24 hours and are able to expand in perfusion culture.

The present inventors have demonstrated small-scale feasibility of integrating gene transfer and culture expansion using a bidirectional-flow, microfluidic bioreactor.

Example 11

The present inventors have shown that cells are captured by monoclonal Ab binding to their surface antigens when there is flow along at the base of grooves. The average flow velocity along grooves was 21.5 mm/min. Comsol simulations have shown that the fluid shear stress at the base of grooves was 0.2 dynes/cm².

The present inventors have demonstrated release of captured cells and subsequent expansion of target cells using the enzyme neuraminidase.

CD34+ cells (white bars), respectively. Non-specific binding of cells to untreated polystyrene dishes was blocked by Pluronic F127.

Bound CD3+ cells and CD34+ cells expanded in tissue culture (black with white diagonal lines or white with black diagonal lines, respectively), though we show that expansion and yield is increase by releasing cells from the substrate.

The enzyme neuraminidase cleaved bound CD3+ or CD34+ cells with an increase in the level of expansion after 5 days of culture (FIG. 30).

Figure 31:
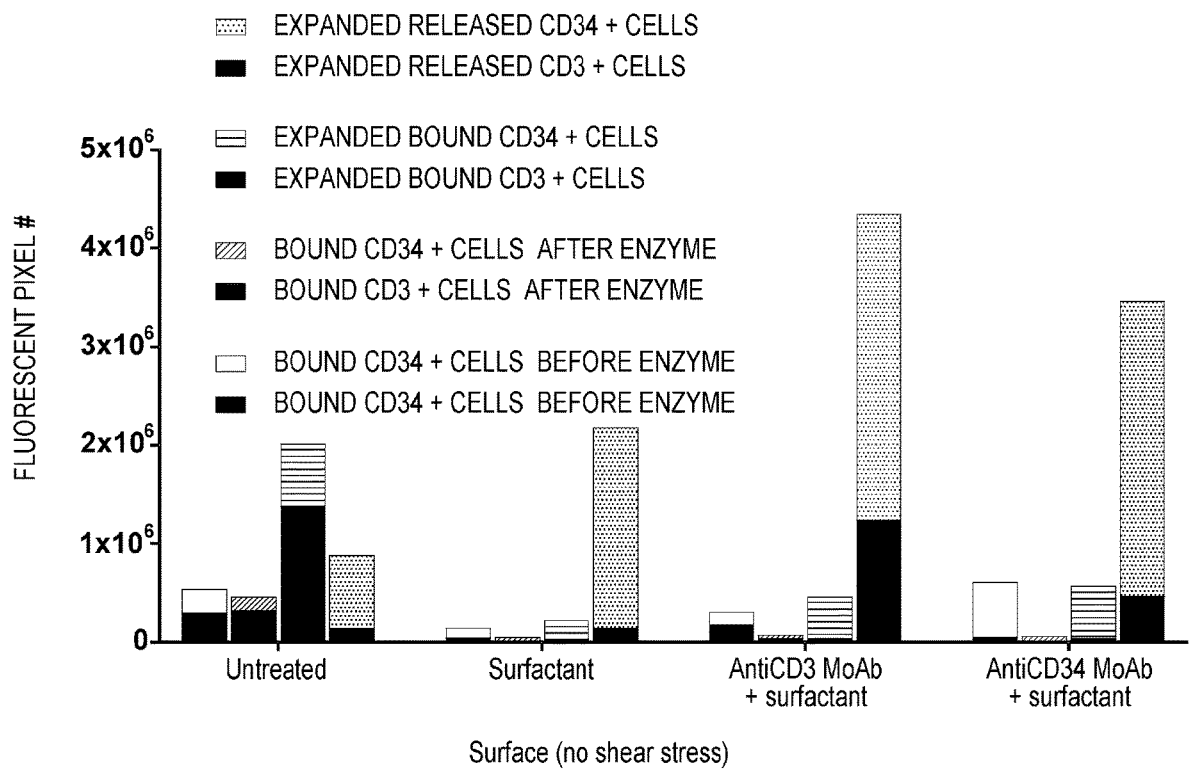
FIG. 31 shows effect of cell releasing enzyme (neuraminidase) on cell detachment and culture.

In these experiments, cells were incubated onto treated polystyrene without orbital shear. Generally the level of enrichment of bound CD3+(black bars) and CD34+ cells (white bars) was lower without orbital shaking (see FIG. 30 versus FIG. 31). The enzyme neuraminidase detached antibody-bound cells, leaving relatively few bound cells (bars with diagonal lines). The cells released by enzyme (white stippled bars, CD34+ cells; black stippled bars, CD3+ cells) grew better than bound cells (white with black horizontal lines, CD34+ cells, black with horizon white lines, CD3+ cells). Therefore, fluid shear and enzyme release increase the purity and the yield of viable cells.

Embodiments of the disclosure provide a multi-layer microfluidic bioreactor to manufacture cells, including genetically modified cells, for use in human cell and gene therapy. Embodiments of the present disclosure provide a viable and economical alternative to existing large-footprint machines, that are often flask or bag based and require skilled staff and complicated multi-step procedures resulting in prohibitively expensive treatment costs and limiting accessibility and take up of life changing and disease-curing therapies.

In some embodiments, the individual bioreactors are connected in parallel, e.g. utilising multilayered sheets typically in a stack which are laminated, to form a microfluidic processor for larger scale manufacture of cells. Typically, microfluidic processor stacks are disposable (single use per patient). Large scale cell manufacture can be automated in some embodiments, by loading one or more microfluidic bioreactors or bioreactor stacks into a bioreactor cell culture system, wherein the system has a controller that is operable to regulate parameters such as gas and fluid flows, temperature, humidity, timing and sample handling in a closed system eliminating risk of contamination and human error which accompanies flask-based cell culture systems.

While laboratory applications may require single or small numbers of multi-layer microfluidic bioreactors to generate the required number of cells, large scale production utilising processor controlled components enable automation of protocols for large scale production of cells, where protocols may be variable between patients and determined according to clinical needs. The geometry of the grooved flow layer in conjunction with ability to provide cross flow and, in many embodiments, longitudinal flow, provides control over cell retention inside the grooves during various cell culture processes and efficient removal of cultured cells.

The geometry can be modified and scaled according to the required cell culture objective, the number of cells to be processed, frequency of cells in inoculum and number of cells to be manufactured. Simulations using software packages such as COMSOL Multiphysics enable fast and reliable simulation of such geometries. Advantageously, models simulated using products such as COMSOL Multiphysics can be modified to simulate the effect of design and boundary conditions and can be used to guide groove geometry for different cell culture processes. In this way, bioreactors according to embodiments of the disclosure can be "tuned" to different processes such as cell separation, selection, transduction, transfection, expansion, or a combination of these. Once the geometry is determined for the desired process, individual bioreactors can be connected in parallel, typically in stacks and a single fluid line connected to the required media sources provide a common feed to each individual inlet via through bores providing vertical fluid flow channels supplying each input, and providing an exit path for waste output and extracted cells respectively.

Previous approaches for scale-up and scale-out of cell production have involved increasing the volume and number of bioreactor systems, respectively. This is expensive and complex because physical (heat and mass transfer such as oxygen transfer and mixing time), biochemical (medium composition and rheology) and process steps (including cell isolation, gene transfer and culture expansion) will vary depending on the clinical dose. Further complexities arise because the cell product and process are specific for each patient; it is the cells of the patient or a tissue-match donor that are modified. The logistics of manufacturing thousands of customised cell products using previous laboratory methods and supply chain presents a challenge which has previously been insurmountable. Embodiments of the present disclosure address these needs by incorporating unique microfluidic geometry into a semipermeable substrate in such a way that multiple process steps can be performed. This unique arrangement also provides for better cell manipulation, high cell density and vastly reduces consumption of media and cell production time frames.

The present disclosure provides for automation of reagent and media exchange steps, replacing cumbersome manual methods such as cell passaging (pipetting) and centrifugation, or filtration devices, which tend to get clogged. The methods, devices and systems disclosed replace a complex 'production line' process (cell selection/gene transfer/expansion) with a single (yet scalable) microfluidic bioreactor device and a programmable controller which directs flows of reagents and cells. The invention also addresses the expense of tissue-matched (autologous or allogeneic) 'scale-out' of cell manufacture for cell and gene therapies.

In embodiments providing large scale cell production, a parallel flow resistive network ensures that flow to each microfluidic subunit is identical and not affected by e.g. supply channel geometry or flow channel geometry. Advantageously, the same operational and production parameters, including flow rates and media constituents, are deployed for small scale (single microfluidic bioreactor) and large scale (multiple microfluidic bioreactors connected in parallel) systems. The process is optimised cheaply at a small scale, and scaled by parallel replication, without the need to repeat the optimisation process if number of cells to be grown increases.

Advantageously, the use of microfluidic resistive parallel networks guarantees identical flow to each microfluidic bioreactor in a multi-unit processor or stack, although individual stacks in a large scale system may be individually configurable under control of a controller for parallel processing of cells according to protocols required individual patient needs. An unexpected observation during testing was that with cross flow, cells fill consecutive downstream grooves during the growth phase (as well as during cell deposition), and can be continuously harvested at the outlet although they need not be. This advantage does not exist in existing large scale production which is traditionally done using batch processing (bags or stirred bioreactors).

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components or group thereof.

It is to be understood that various modifications, additions and/or alterations may be made to the parts previously described without departing from the ambit of the present invention as defined in the claims appended hereto.

Future patent applications may be filed in various countries on the basis of or claiming priority from the present application. It is to be understood that the following claims are provided by way of example only, and are not intended to limit the scope of what may be claimed in any such future application. Features may be added to or omitted from the claims at a later date so as to further define or re-define the invention or inventions.

The invention claimed is:

1. A multi-layer microfluidic bioreactor for cell culture, comprising a header layer, a base layer and a fluid permeable flow layer between the header layer and the base layer, wherein:
   (a) the flow layer comprises an upper surface and a lower surface, and the upper surface comprises one or more grooves for retention of cells;
   (b) the base layer provides a gas flow path for gas exchange across the flow layer; and (c) the header layer is configured to define a flow channel over the flow layer upper surface, and the header layer comprises:
(i) a first inlet port;
(ii) a first outlet port;
(iii) a second outlet port;
(iv) one or more first fluid inlets providing fluid communication between the first inlet port and the flow channel;
(v) one or more first fluid outlets providing fluid communication between the flow channel and the first outlet port; and
(vi) one or more second fluid outlets providing fluid communication between the flow channel and the second outlet port;
wherein the one or more first fluid inlets and the one or more first fluid outlets are positioned in the header layer such that fluid entering the flow channel from the one or more first fluid inlets moves in a first flow direction toward the one or more first fluid outlets, the first flow direction being across the one or more grooves to minimize disruption of cells received therein, and
wherein the one or more second fluid outlets are positioned in the header layer such that fluid exiting the flow channel through the second outlet port flows in a second flow direction toward the one or more second fluid outlets, the second flow direction being along the one or more grooves.

2. The multi-layer microfluidic bioreactor according to claim 1, wherein the header layer further comprises:
a second inlet port; and
one or more second fluid inlets providing fluid communication between the second inlet port and the flow channel;
wherein the one or more second fluid inlets are positioned along a dimension of the header which is substantially orthogonal to a longitudinal dimension of the one or more grooves so that fluid entering the flow channel from the one or more second fluid inlets flows toward the one or more second fluid outlets in the second flow direction.

3. The multi-layer microfluidic bioreactor according to claim 2, wherein the second inlet port receives fluid from one or more media sources, and the header layer comprises one or more bores for receiving the fluid media into the second inlet port, and optionally, wherein the one or more bores extend through the header layer, the flow layer and the base layer, to form vertical channels through the multilayer microfluidic bioreactor.

4. The multi-layer microfluidic bioreactor according to claim 1, wherein the first flow direction and the second flow direction are substantially orthogonal.

5. The multi-layer microfluidic bioreactor according to claim 1, further comprising a selectively permeable membrane separating the flow channel into a first flow channel and a second flow channel; wherein the selectively permeable membrane provides for exchange of low molecular weight metabolites.

6. The multi-layer microfluidic bioreactor according to claim 5, further comprising a secondary header layer, wherein the selectively permeable membrane is between the header layer and the secondary header layer thereby forming the second flow channel therebetween, wherein the secondary header layer comprises:
(i) a secondary inlet port in fluid communication with the second flow channel; and optionally,
(ii) a secondary outlet port in fluid communication with the second flow channel;
wherein the selectively permeable membrane provides for exchange of low molecular weight fluid metabolites entering the secondary inlet port and optionally, for removal of low molecular weight fluid metabolites through the secondary outlet port.

7. The multi-layer microfluidic bioreactor according to claim 1, wherein the one or more grooves are functionalized to limit non-specific binding of cells in the one or more grooves.

8. The multi-layer microfluidic bioreactor according to claim 1, configured for arrangement in a stack including at least one further multi-layer microfluidic bioreactor, each multi-layer microfluidic bioreactor comprising one or more through ports extending colinearly through each of the header layer, the base layer and the flow layer and providing fluid communication with corresponding through ports of the at least one further multi-layer microfluidic bioreactor, and optionally further comprising one or more alignment features for positioning of at least one further multi-layer microfluidic bioreactor in stacked arrangement.

9. A bioreactor cell culture system comprising:
(a) a plurality of multi-layer microfluidic bioreactors according to claim 1 arranged in at least one stack;
(b) a controller configured to control individually operation of one or more fluid pumps according to a cell culture protocol stored in a memory of the controller, the one or more fluid pumps delivering fluid to one or more through ports provided colinearly through the at least one stack, the delivered fluid entering the flow channel of each microfluidic bioreactor in the at least one stack according to the stored cell culture protocol.

10. The bioreactor cell culture system of claim 9, comprising one or both of:
(a) a substantially rigid base plate beneath the at least one stack; and
(b) a substantially rigid cover plate arranged over the at least one stack;
wherein each of the base plate and the cover plate impart structural support to the at least one stack; and
optionally wherein the substantially rigid cover plate comprises a plurality of openings providing fluid communication between through ports in the one or more stacks and one or more fluid sources and/or waste reservoirs.

11. The bioreactor cell culture system according to claim 9, wherein the controller is operable to cause extraction of cells from the one or more grooves of the individual multi-layer microfluidic bioreactors arranged in a stack through a cell extraction through port extending colinearly through the stack of multi-layer microfluidic bioreactors, and in fluid communication with the second outlet port in the individual multi-layer microfluidic bioreactors, and optionally further comprising a coupling for receiving a receptacle for uncontaminated collection of extracted cells from the one or more stacks of microfluidic bioreactors.

12. A multi-layer bioreactor sheet comprising a plurality of multi-layer microfluidic bioreactors according to claim 1, each of the multi-layer microfluidic bioreactors comprising a culture chamber containing one or more grooves and one or more through ports providing for flow of fluid across the one or more grooves, wherein the one or more through ports are provided colinearly through the layers of the multi-layer bioreactor sheet.

13. A multi-layer bioreactor sheet according to claim 12, wherein each multi-layer bioreactor sheet is configured for arrangement into a sheet stack comprising at least one other multi-layer bioreactor sheet, wherein through ports in each multi-layer bioreactor sheet in the sheet stack extend colinearly providing fluid communication with the culture chambers of individual multi-layer microfluidic bioreactors in each multi-layer bioreactor sheet.

14. A bioreactor cell culture system for use with one or more multi-layer bioreactor sheets arranged in a sheet stack according to claim 13, the system comprising:
(a) a controller to control individually operation of one or more fluid pumps according to a cell culture protocol stored in a memory of the controller;
(b) a sheet stack header providing fluid coupling between at least one fluid or waste reservoir in the bioreactor cell culture system and multiple through ports in the sheet stack requiring flow to or from the at least one fluid or waste reservoir according to the stored cell culture protocol; and
(c) one or more fluid pumps delivering fluid via the through ports to individual culture chambers of the multi-layer microfluidic bioreactors in accordance with the stored cell culture protocol.

15. A method of performing cell culture, cell transfection/transduction, or cell selection comprising growing cells in a multi-layer microfluidic bioreactor according to claim 1.

16. A method of performing cell culture, cell transfection/transduction, or cell selection comprising growing cells in a bioreactor cell culture system according to claim 9.

17. The multi-layer microfluidic bioreactor according to claim 1, wherein the one or more grooves are functionalized with a capture reagent that selectively captures cells.

18. The multi-layer microfluidic bioreactor according to claim 1, wherein the one or more grooves are functionalized with polymers that limit non-specific binding of cells in the one or more grooves.

19. The multi-layer microfluidic bioreactor according to claim 3, wherein the one or more bores extend colinearly through the header layer, the flow layer and the base layer, to form vertical channels through the multilayer microfluidic bioreactor.

* * * * *